United States Patent
Voelker

(10) Patent No.: US 11,278,556 B2
(45) Date of Patent: Mar. 22, 2022

(54) METHODS AND COMPOSITIONS FOR TREATING AND PREVENTING RESPIRATORY RELATED DISEASES AND CONDITIONS WITH XYLITOL-HEADGROUP LIPID ANALOGS

(71) Applicant: National Jewish Health, Denver, CO (US)

(72) Inventor: Dennis R. Voelker, Littleton, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 16/488,865

(22) PCT Filed: Feb. 27, 2018

(86) PCT No.: PCT/US2018/019860
§ 371 (c)(1),
(2) Date: Aug. 26, 2019

(87) PCT Pub. No.: WO2018/157107
PCT Pub. Date: Aug. 30, 2018

(65) Prior Publication Data
US 2020/0009165 A1   Jan. 9, 2020

Related U.S. Application Data

(60) Provisional application No. 62/463,838, filed on Feb. 27, 2017.

(51) Int. Cl.
*A61K 31/683* (2006.01)
*A61P 31/14* (2006.01)
*A61K 9/00* (2006.01)

(52) U.S. Cl.
CPC .......... *A61K 31/683* (2013.01); *A61K 9/0043* (2013.01); *A61P 31/14* (2018.01)

(58) Field of Classification Search
CPC .............................. A61K 31/683; A61P 31/14
See application file for complete search history.

(56) References Cited

U.S. PATENT DOCUMENTS

2008/0242640 A1   10/2008   Voelker

OTHER PUBLICATIONS

Fickes "Innate Immune Activity of Xylitol-Headgroup Lipid Analogs of the Anionic Pulmonary Surfactant Phospholipids," University of Colorado, 2011, Thesis for Doctor of Philosophy degree, 196 pages [retrieved online from: dspace.ibrary.colostate.edu/bitstream/handle/10968/1619/Fickes_ucdenveramc_1639D_10342.pdf?sequence=1].
Fickes et al. "Tandem mass spectrometry of novel ether-linked phospholipid analogs of anionic pulmonary surfactant phospholipids," Rapid Communications in Mass Spectrometry, Dec. 2016, vol. 30, No. 24, pp. 2601-2606.
International Preliminary Report on Patentability for International (PCT) Patent Application No. PCT/US2018/019860, dated Sep. 6, 2019 12 pages.
International Search Report and Written Opinion prepared by the ISA/US dated Apr. 21, 2018, for International Application No. PCT/US2018/019860.

*Primary Examiner* — Samira J Jean-Louis
(74) *Attorney, Agent, or Firm* — Sheridan Ross P.C.

(57) ABSTRACT

The invention generally relates to methods to prevent and/or inhibit viral infection as well as to inhibit inflammation and/or pathogen infection by administering at least one xylitol lipid analog or compositions comprising at least one xylitol lipid analog to an individual. The invention also relates to methods to prevent or inhibit respiratory syncytial virus (RSV) infection by administering at least one xylitol lipid analog or compositions comprising at least one xylitol lipid analog to an individual.

14 Claims, 21 Drawing Sheets
Specification includes a Sequence Listing.

16:1 DPPX

Figure 9B

METHODS AND COMPOSITIONS FOR TREATING AND PREVENTING RESPIRATORY RELATED DISEASES AND CONDITIONS WITH XYLITOL-HEADGROUP LIPID ANALOGS

CROSS-REFERENCE TO RELATED APPLICATIONS

This application is a national stage application under 35 U.S.C. § 371 and claims the benefit of PCT Application No. PCT/US2018/019860 having an international filing date of Feb. 27, 2018, which designated the United States, which PCT application claims the benefit of priority under 35 U.S.C. § 119(e) to U.S. Provisional Patent Application Ser. No. 62/463,838, filed Feb. 27, 2017. The entire disclosures of PCT Application No. PCT/US2018/019860 and U.S. Provisional Patent Application No. 62/463,838 are incorporated herein by reference.

GOVERNMENT SUPPORT

This invention was made with government support under grant number R01 HL094629 received from the National Institutes of Health. The government has certain rights in the invention.

REFERENCE TO A SEQUENCE LISTING

This application contains a Sequence Listing submitted electronically as a text file by EFS-Web. The text file, named "2897-205-PCT_Seq_Listing_ST25", has a size in bytes of 1000 bytes, and was recorded on 27 Feb. 2018. The information contained in the text file is incorporated herein by reference in its entirety pursuant to 37 CFR § 1.52(e)(5).

BACKGROUND OF THE INVENTION

Phospholipids are the major constituents of pulmonary surfactant and play critical roles in regulating immune functions of the lung. Previous studies reported that the minor pulmonary surfactant lipid, palmitoyl-oleoyl-phosphatidylglycerol (POPG), inhibits RSV-induced inflammation and infection in mice, and in vitro viral transmission. POPG, acts as a potent antagonist of the activation of TLRs 1, 2, 3, 4, 6, 7, and 8 and suppresses inflammatory responses in airways and alveoli but has a short half-life in the mouse lung.

The innate immune system is the first line of defense against foreign microorganisms entering the body. Upon detection of a pathogen, the innate immune system launches an inflammatory response, recruits immune cells to the site of infection, and signals for the activation of the adaptive response (A. S. Kenneth Murphy, et al. *Janeway's Immunobiology*, vol. 7, no. 6. 2008). A major component of the innate immune system is pattern recognition receptors (PRRs). The Toll-like receptor (TLR) family comprises a major subset of the PRRs. TLRs detect the presence of invading pathogens by recognizing conserved molecular patterns expressed by Gram-negative and Gram-positive bacteria, viruses and fungi, and selectively identify them as foreign (O. Takeuchi and S. Akira, "Pattern Recognition Receptors and Inflammation," *Cell*, vol. 140, no. 6, pp. 805-820, 2010; S. Akira, et al. "Pathogen Recognition and Innate Immunity," *Cell*, vol. 124, no. 4, pp. 783-801, 2006). Although TLRs play a necessary and critical role in detection of foreign invaders, and downstream activation of the appropriate response genes; several of these receptors also have been implicated in contributing to an overly robust inflammatory response that leads to tissue damage.

Respiratory syncytial virus (RSV) is a leading cause of lower respiratory tract infections in newborns, the elderly, and those with chronic respiratory disease. There is no vaccine for RSV, nonatural development of enduring immunity, and reinfection occurs throughout life. Currently, there is an urgent need for new approaches to prevent and treat RSV infection. RSV, begins as an upper respiratory tract infection but also has the ability to move down into the lower respiratory tract and cause pneumonia and bronchiolitis (B. S. Graham, "Biological challenges and technological opportunities for respiratory syncytial virus vaccine development.," *Immunol. Rev.*, vol. 239, no. 1, pp. 149-66, January 2011). RSV infects humans of all ages and populations but is especially serious in infants, the elderly, people with underlying lung conditions and immunocompromised individuals. Lasting immunity is not developed following RSV infection and severe RSV infection in children has been linked with the development of chronic respiratory problems, such as asthma (T. Saraya, et al, "Epidemiology of virus-induced asthma exacerbations: with special reference to the role of human rhinovirus.," *Front. Microbiol.*, vol. 5, p. 226, 2014).

Acute respiratory distress syndrome (ARDS) is a severe inflammatory disease resulting in a 30% mortality rate (V. M. Ranieri, et al., "Acute respiratory distress syndrome: the Berlin Definition.," *JAMA*, vol. 307, no. 23, pp. 2526-33, June 2012). Although current therapy for ARDS improves lung function in some patients, the death toll of ARDS remains the same. Respiratory viruses are primary causes of acute lung injury (ALI) including the most severe form, acute respiratory distress syndrome (ARDS) (Y. Imai, et al., "Identification of oxidative stress and Toll-like receptor 4 signaling as a key pathway of acute lung injury.," *Cell*, vol. 133, no. 2, pp. 235-49, April 2008; M. A. Matthay, et al., "The acute respiratory distress syndrome.," *J. Clin. Invest.*, vol. 122, no. 8, pp. 2731-40, August 2012). Among the most common respiratory pathogen implicated in pulmonary viral infections is RSV. Severe RSV is the leading cause of bronchiolitis, pneumonia and acute lower respiratory tract infections, and is a leading cause of global child mortality (W. P. Glezen, et al., "Epidemiologic patterns of acute lower respiratory disease of children in a pediatric group practice.," *J. Pediatr.*, vol. 78, no. 3, pp. 397-406, March 1971). Exacerbation of chronic pulmonary diseases as well as ALI/ARDS affects millions of people and in many cases current therapies are inadequate. The development of novel therapeutics to target respiratory viruses can make management and resolution of ALI/ARDS more attainable. Specifically targeting the respiratory pathogen, RSV, as a known factor in development of ALI, could provide significant protection for patients.

There is currently an unmet need for pharmacologic agents that have antagonist activity against specific TLRs. Such antagonists would enable clinicians to tailor immune responses or inhibit harmful over-activation of specific TLRs. Current treatments for RSV infections are lacking and in need of innovative approaches for the development of preventative and therapeutic agents, especially because no vaccines have yet been approved for this virus. The recent discovery that the endogenous surfactant lipid, POPG, possesses anti-inflammatory and antiviral activity, suggests a new pharmacological approach for modulation of innate immunity (P. Kandasamy, et al., "Structural analogs of pulmonary surfactant phosphatidylglycerol inhibit toll-like receptor 2 and 4 signaling," *J. Lipid Res.*, vol. 57, no. 6, pp. 993-1005, 2016; P. Kandasamy, et al., "Pulmonary surfactant phosphatidylglycerol inhibits *Mycoplasma pneumoniae*-stimulated eicosanoid production from human and mouse macrophages," *J. Biol. Chem.*, vol. 286, no. 10, pp. 7841-7853, 2011; K. Kuronuma, et al., "Anionic Pulmonary Surfactant Phospholipids Inhibit Inflammatory Responses from Alveolar Macrophages and U937 Cells by Binding the Lipopolysaccharide-interacting Proteins CD14 and MD-2," *J. Biol. Chem.*, vol. 284, no. 38, pp. 25488-25500, September 2009; M. Numata, et al., "Nanodiscs as a therapeutic delivery agent: Inhibition of respiratory syncytial virus infection in the lung," *Int. J. Nanomedicine*, vol. 8, pp. 1417-1427, 2013).

Phospholipids are the major constituents of pulmonary surfactant and play critical roles in regulating immune functions of the lung. Previous studies reported that the minor pulmonary surfactant lipid, palmitoyl-oleoyl-phosphatidylglycerol (POPG), inhibits RSV-induced inflammation and infection in mice, and in vitro viral transmission. POPG, acts as a potent antagonist of the activation of TLRs 1, 2, 3, 4, 6, 7, and 8 and suppresses inflammatory responses in airways and alveoli but has a short half-life in the mouse lung.

SUMMARY OF THE INVENTION

One embodiment of the invention relates to a method to prevent and/or inhibit viral infection, comprising administering to an individual who has, or is at risk of developing a viral infection, at least one xylitol lipid analog, wherein the amount of the xylitol lipid analog is effective to prevent or inhibit said viral infection, and wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds.

In one aspect, the viral infection activates Toll-like receptors (TLR) selected from the group consisting of: TLR1, TLR2, TLR3, TLR4, TLR6, TLR7, TLR8, TLR9, and TLR10.

In one aspect, the viral infection is a respiratory viral infection selected from the group consisting of respiratory syncytial virus (RSV), influenza A virus, influenza B virus, rhinovirus, metapneumovirus, and parainfluenza virus.

In one aspect, the viral infection is RSV.

In one aspect, the individual is a neonatal infant.

In one aspect, the xylitol lipid analog is administered to the individual prior to any indication of viral infection.

In one aspect, the xylitol lipid analog is administered to the individual subsequent to identification of a symptom of or confirmation of viral infection of the individual.

Another embodiment of the invention relates to a method to inhibit inflammation and/or a pathogen infection, disease or condition, comprising administering to an individual who has, or is at risk of developing said inflammation and/or pathogen infection, disease, or condition, an amount of at least one xylitol lipid analog, wherein the amount of the xylitol lipid analog is effective to inhibit said inflammation or pathogen infection, and wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds.

In one aspect, the inflammation and/or pathogen infection is associated with a toll-like receptor (TLR) selected from the group consisting of: TLR1, TLR2, TLR3, TLR4, TLR6, TLR7, TLR8, TLR9, and TLR10.

In one aspect, the individual has an infection, condition, or disease associated with TLR2 selected from the group consisting of: cytomegalovirus infection, herpes simplex virus infection, measles, a gram positive bacterial infection, a protozoan infection, a fungal infection, and Varicella zoster infection.

In one aspect, the individual has an infection, condition, or disease associated with TLR3 selected from the group consisting of: a viral infection and a cancer.

In one aspect, the individual has an infection, condition, or disease associated with TLR4 selected from the group consisting of: cytomegalovirus infection, herpes simplex virus infection, measles, influenza A, influenza B, RSV, rhinovirus, a gram-negative bacterial infection, a protozoan infection, a fungal infection, and Varicella zoster infection.

In one aspect, the individual has an infection, condition, or disease associated with TLR7 selected from the group consisting of: an autoimmune disease, a cancer, and a viral infection.

In one aspect, the infection is selected from the group consisting of: human immunodeficiency virus infection, rhinovirus infection, parainfluenza virus infection, human parechorvirus infection, influenza infection, papilloma virus infection, and Varicella zoster infection.

In one aspect, the individual has an infection, condition, or disease associated with TLR8 selected from the group consisting of: autoimmune disease, basal cell carcinoma, Bowen's disease, condyloma, genital warts, human immunodeficiency virus (HIV), rhinovirus, influenza virus, respiratory syncytial virus, parainfluenza virus, Human parechovirus, melanoma, and mollusca contagiosa.

In one aspect, the individual has a respiratory disorder.

In one aspect, the respiratory disorder is selected from the group consisting of: adult respiratory distress syndrome (AoplRDS), acute lung injury (ALI), viral infection associated with asthma, chronic obstructive pulmonary disease (COPD), asthma, pneumonia, bronchitis, tuberculosis, reactive airway disease syndrome, interstitial lung disease, rhinitis, and parasitic lung disease.

Another embodiment of the invention relates to a method to inhibit inflammation, comprising administering to an individual who has, or is at risk of developing said inflammation, a composition comprising at least one xylitol lipid analog, wherein the xylitol lipid analog is effective to inhibit said inflammation, and wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds; and wherein the composition is selected from the group consisting of: a homogeneous lipid preparation consisting of the xylitol lipid analog; a composition comprising a homogeneous lipid preparation of the xylitol lipid analog and at least one agent for the treatment of inflammation; a composition comprising a preparation of randomly mixed surfactant lipids combined with a homogeneous lipid preparation of the xylitol lipid analog; and a preparation of randomly mixed surfactant lipids, wherein the xylitol lipid analog comprises at least about 50% of the total lipids in said randomly mixed surfactant lipids.

In one aspect of this embodiment, the composition is a preparation of randomly mixed surfactant lipids combined with a homogeneous lipid preparation of the xylitol lipid analog.

In one aspect of this embodiment, the composition is a homogeneous lipid preparation of the xylitol lipid analog and at least one additional agent for treating inflammation.

In one aspect of any of the embodiments related to method described herein, the xylitol lipid analog is administered as a composition comprising a homogeneous lipid preparation of the anionic lipid or related compound.

In one aspect of any of the embodiments related to method described herein, the xylitol lipid analog is administered as a composition comprising a preparation of randomly mixed surfactant lipids combined with a homogeneous lipid preparation of the xylitol lipid analog.

In one aspect of any of the embodiments related to method described herein, the xylitol lipid analog is administered as a preparation of randomly mixed surfactant lipids, wherein the xylitol lipid analog comprises at least about 50% of the total lipids in said randomly mixed surfactant lipids.

In one aspect of any of the embodiments related to method described herein, the xylitol lipid analog is administered to the respiratory tract of the individual.

In one aspect of any of the embodiments related to method described herein, the xylitol lipid analog is administered to the nasal passages of the individual.

Yet another embodiment of the invention relates to a method to produce a surfactant composition, comprising: (a) providing a substantially homogeneous lipid preparation of at least one xylitol lipid analog, wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds; (b) adding the preparation of (a) to a preparation of randomly mixed surfactant lipids.

In one aspect of this embodiment, the preparation of (a) is in aqueous solution.

In one aspect of this embodiment, the preparation of (b) is in aqueous solution.

In one aspect of this embodiment, the preparation is gently mixed to avoid significant fusion or intermixing of lipids between lipid bilayers or micelles in (a) and (b).

In one aspect of this embodiment, the lipids in the preparation of (a) comprise at least 1% of the total lipids in the composition.

Another aspect of the invention relates to a surfactant composition comprising at least one xylitol lipid analog, wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds.

Another aspect of the invention relates to a lipid composition comprising at least one xylitol lipid analog, wherein the xylitol lipid analog has the following characteristics: has a phospholipid glycerol backbone; has a xylitol polar headgroup; has a phosphodiester bond linking the glycerol backbone to the xylitol polar headgroup; has variable hydrophobic regions comprising two aliphatic chains of 14 to 18 carbons in length, wherein linkage between the aliphatic chains and the phospholipid glycerol backbone is an O-acyl linkage or an O-alkyl linkage; and the aliphatic chains contain 0 to 2 double bonds.

Another aspect of the invention relates to a xylitol lipid analog comprising: a phospholipid glycerol backbone; a xylitol polar headgroup; a phosphodiester bond linking the glycerol backbone to the xylitol polar headgroup; and variable hydrophobic regions comprising two aliphatic chains of 14 to 18 carbons in length, wherein linkage between the aliphatic chains and the phospholipid glycerol backbone is an O-acyl linkage or an O-alkyl linkage; and wherein the aliphatic chains contain 0 to 2 double bonds.

In any of the embodiments of the invention described above or elsewhere herein, in one aspect, the xylitol lipid analog is a phosphatidylglycerol analog.

In any of the embodiments of the invention described above or elsewhere herein, in one aspect, the xylitol lipid analog is a palmitoyl-oleoyl-phosphatidylglycerol (POPG) analog with a xylitol headgroup.

In any of the embodiments of the invention described above or elsewhere herein, in one aspect, the xylitol lipid analog is selected from the group consisting of Dimyristoyl-phosphatidylxylitol (DMPX), 14:0 Diether-phosphatidylxylitol (14:0 DEPX), Dipalmitoyl-phosphatidylxylitol (DPPX), Palmitoyl-oleoyl-phosphatidylxylitol (POPX), 16:1 Dipalmitoleoyl-phosphatidylxylitol (16:1 DPPX), Distearoyl-phosphatidylxylitol (DSPX), Dioleoyl-phosphatidylxylitol (DOPX), 18:1 Diether-phosphatidylxylitol (18:1 DEPX), Dilinoleoyl-phosphatidylxylitol (DLPX).

BRIEF DESCRIPTION OF THE DRAWINGS

Figure 9B:
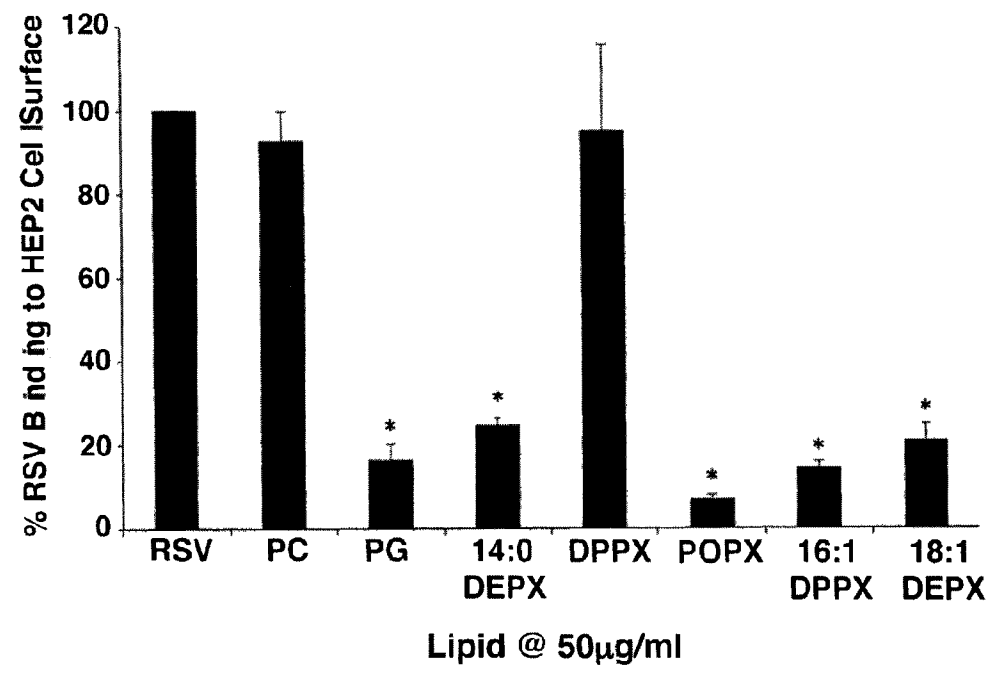

FIGS. 9A and 9B show DOPX and 18:1 DEPX inhibit attachment of RSV to cell surface receptor. Monolayers of HEp2 cells were incubated with RSV (2.5 infectious particles/cell) for 2 hrs at 0° C. in the absence or presence of 50 µg/ml POPC (PC), or POPG (PG) or DOPX, or 18:1 DEPX. Following the incubation the cells were washed 3 times with saline at 0° C., and then harvested in SDS-PAGE loading buffer. After electrophoresis the proteins were transferred to nitrocellulose and immunoblotted with polyclonal anti-RSV and HRP-conjugated secondary antibody. Antibody binding was quantified using enhanced chemi-luminescence. *indicate $p<0.001$.

FIGS. 12A and 12B are data from two separate experiments. Whisker data shown are Means±SE.

DETAILED DESCRIPTION OF THE INVENTION

Figure 1:
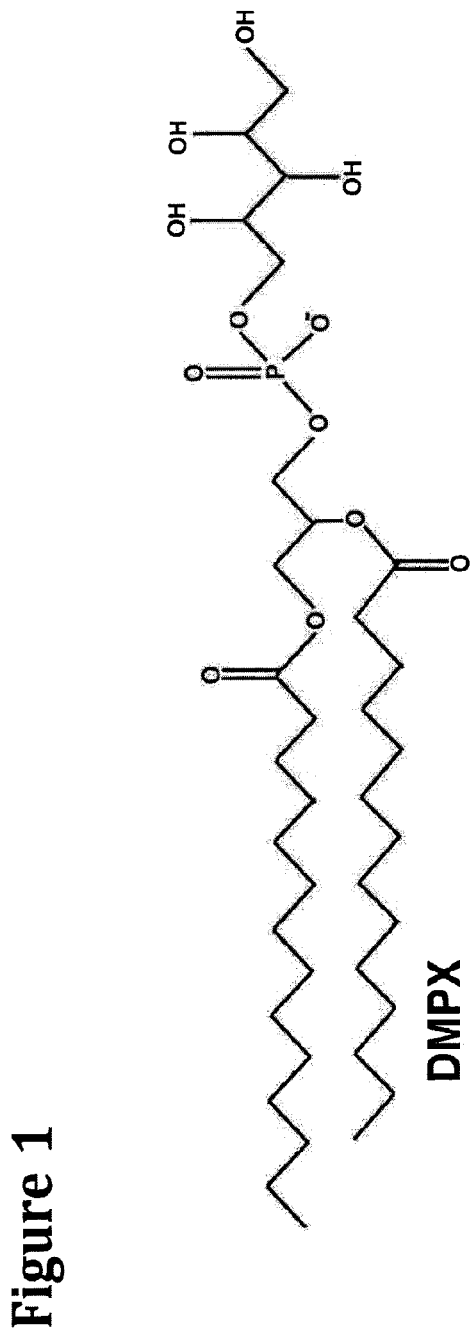
FIG. 1 shows the structures of the novel xylitol headgroup phospholipids (structures of a diacyl- and dialkyl-phosphatidylxylitol compounds). Dimyristoyl-phosphatidylxylitol (DMPX); 14:0 Diether-phosphatidylxylitol (14:0 DEPX); Dipalmitoyl-phosphatidylxylitol (DPPX); Palmitoyl-oleoyl-phosphatidylxylitol (POPX); 16:1 Dipalmitoleoyl-phosphatidylxylitol (16:1 DPPX); Distearoyl-phosphatidylxylitol (DSPX); Dioleoyl-phosphatidylxylitol (DOPX; 18:1 Diether-phosphatidylxylitol (18:1 DEPX); Dilinoleoyl-phosphatidylxylitol (18:2 DLPX, also referred to herein as "DLPX").
Figure 1:
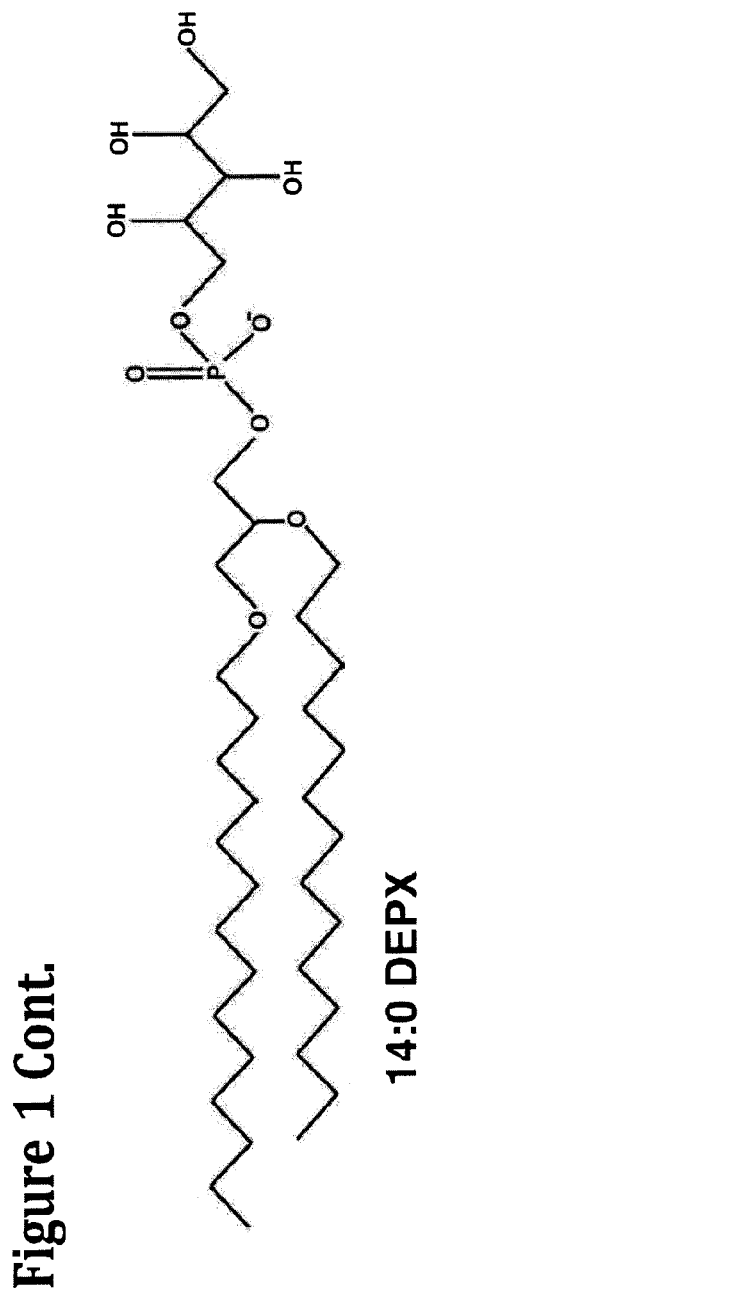
Figure 1:
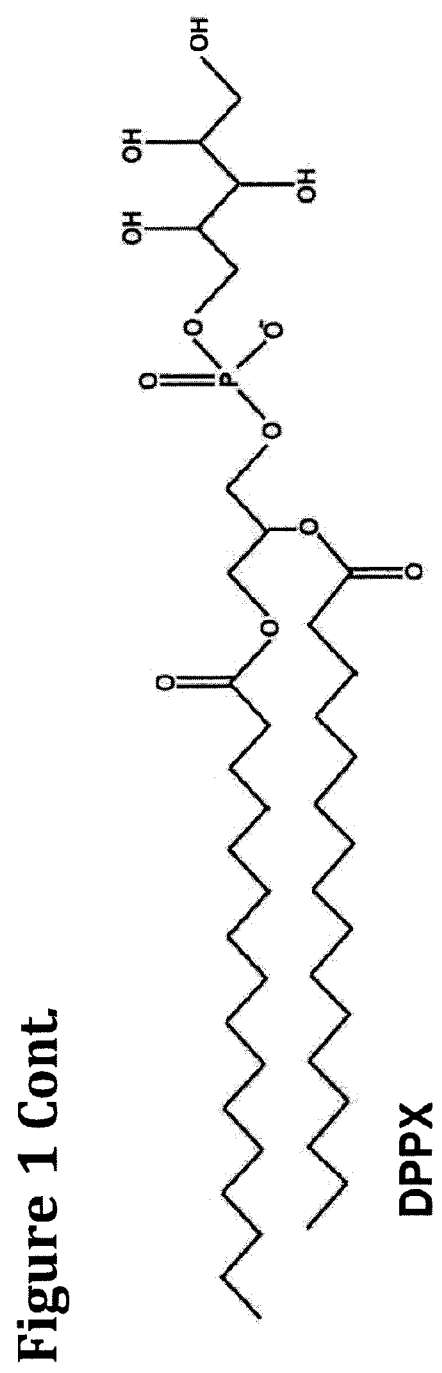
Figure 1:
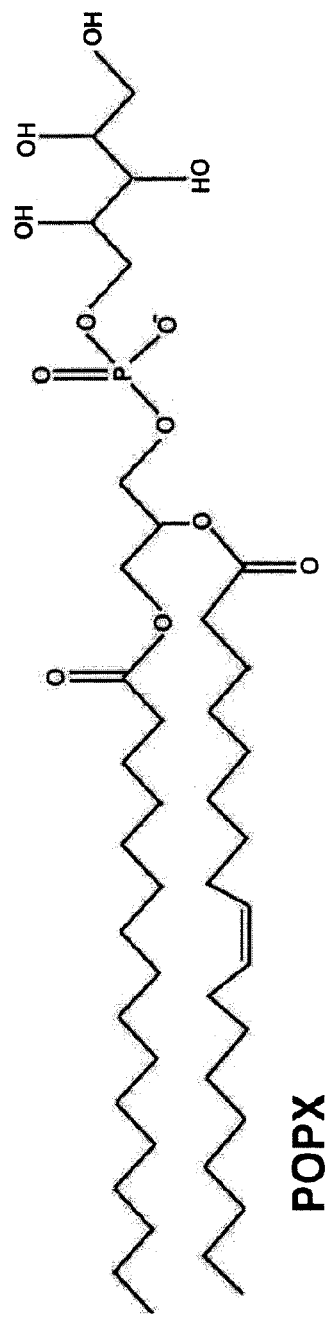
Figure 1:
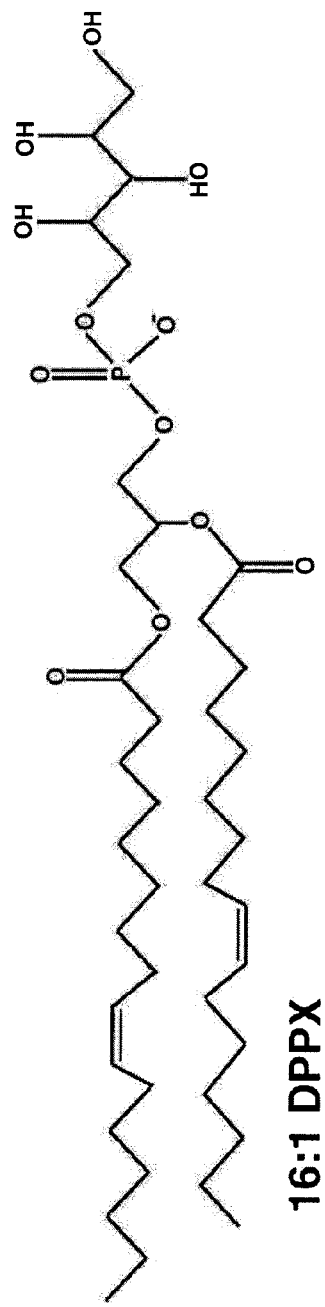
Figure 1:
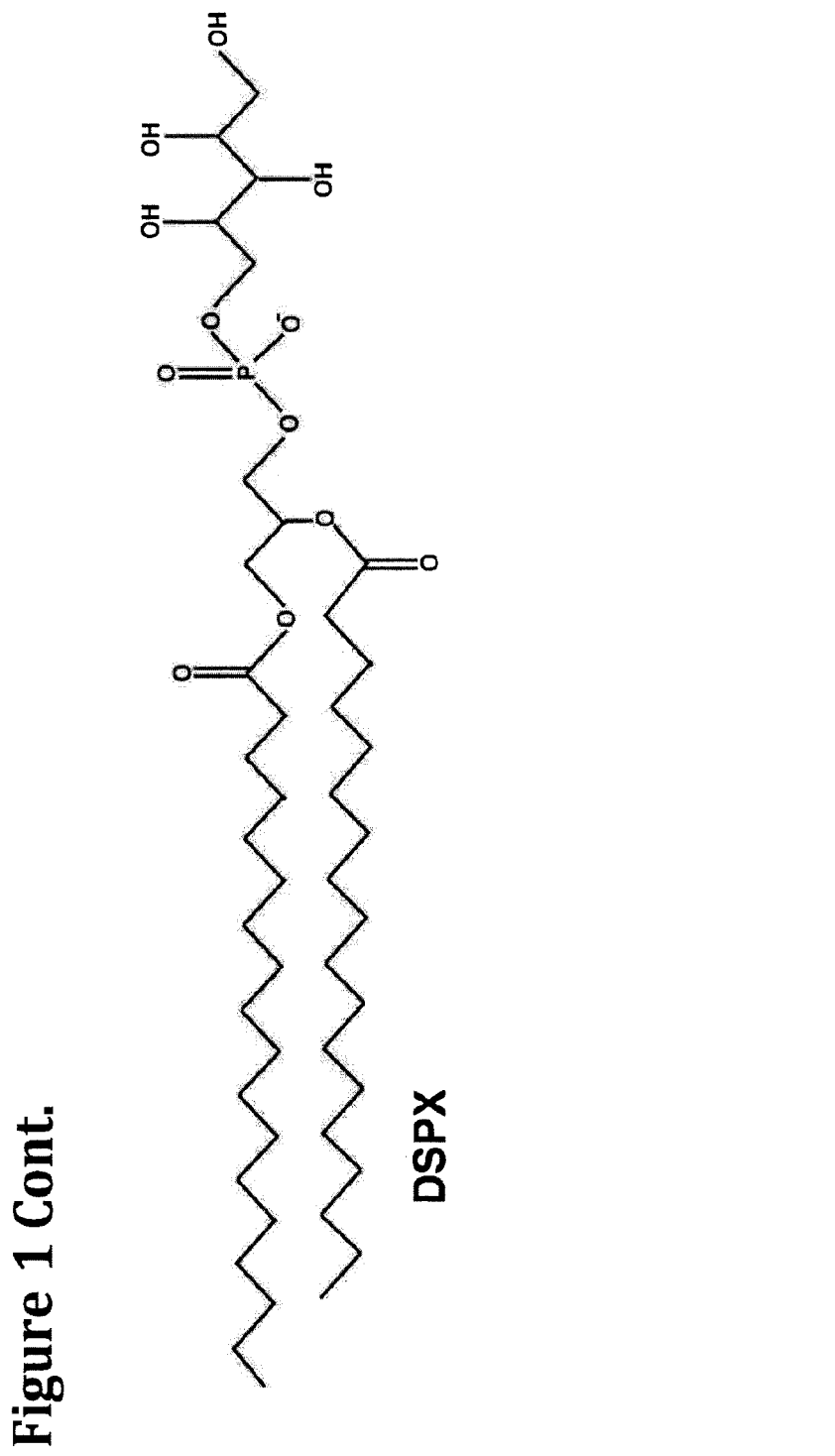
Figure 1:
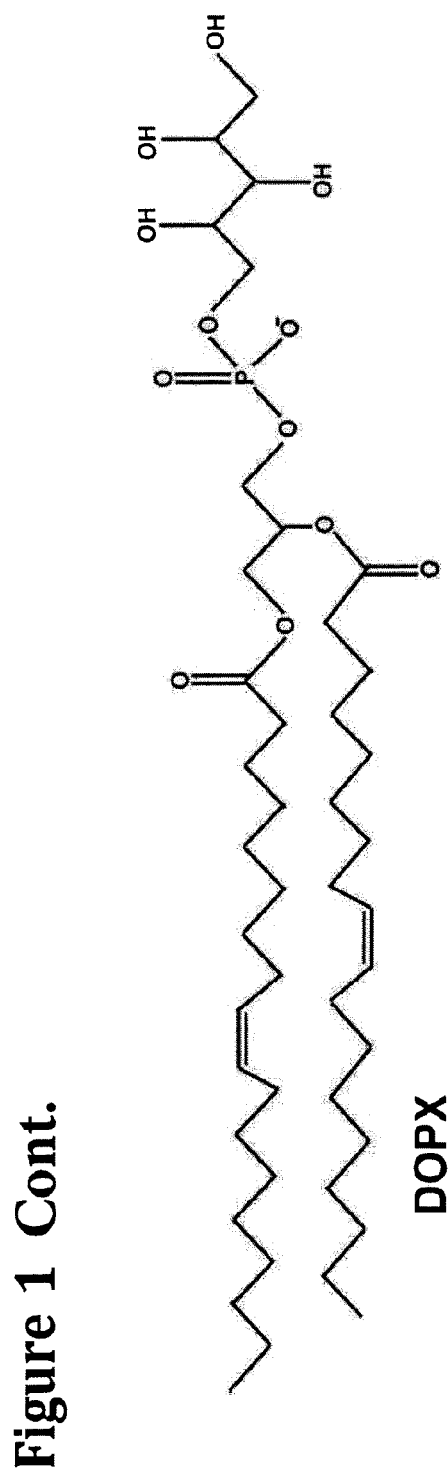
Figure 1:
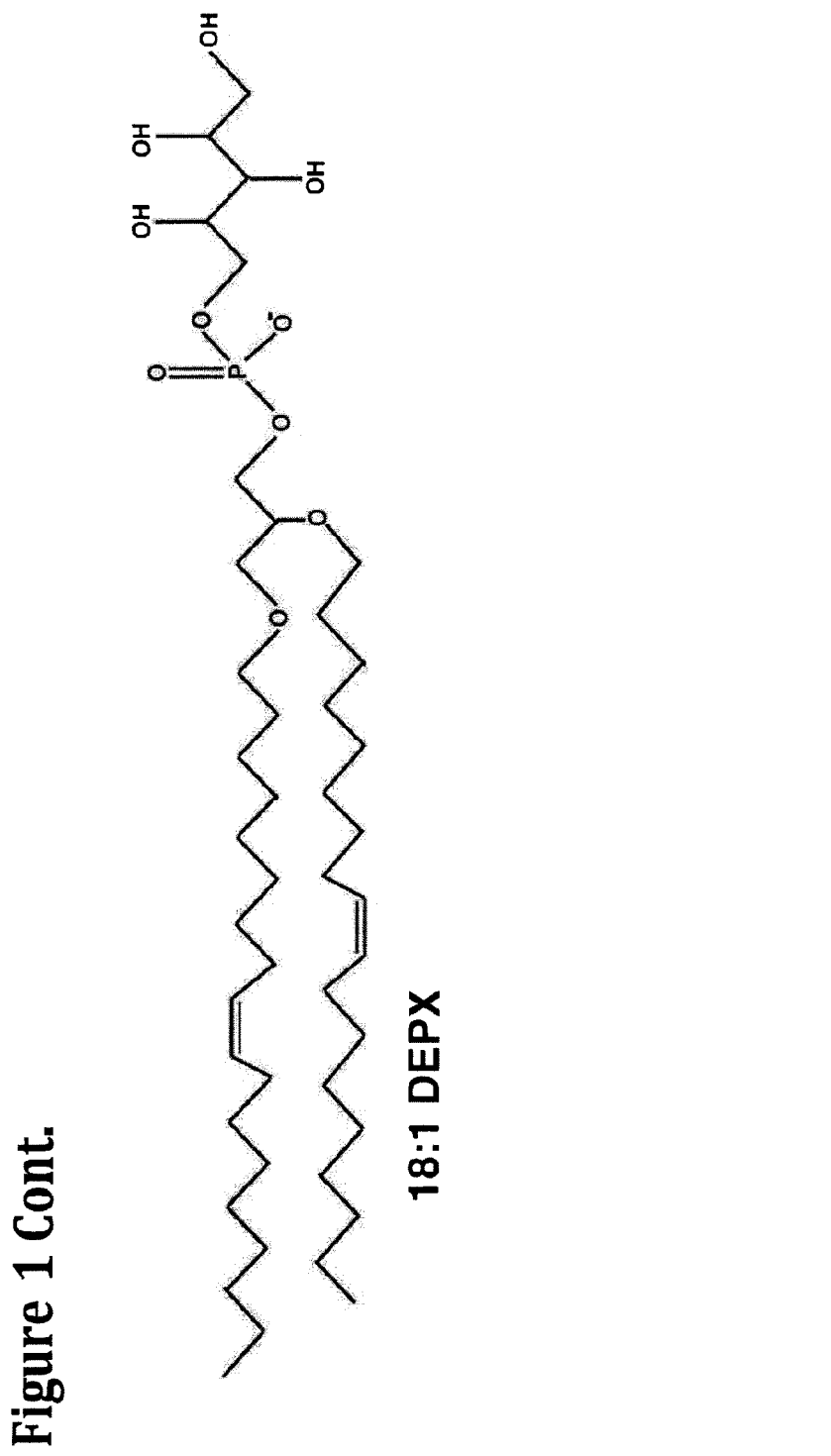
Figure 1:
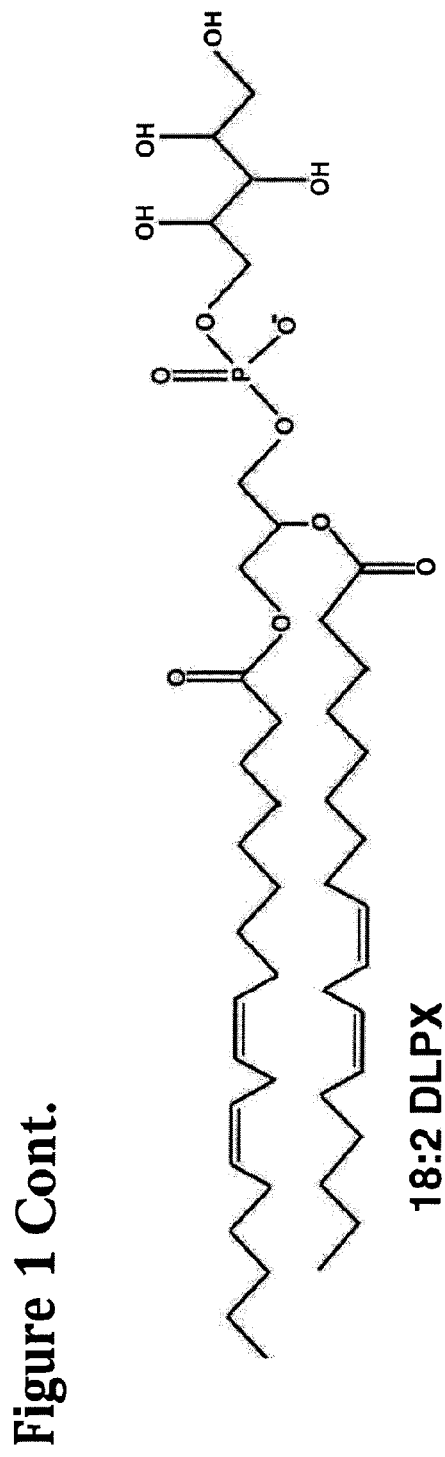

The present invention generally relates to the discovery by the present inventor that novel xylitol-headgroup phospholipids (also referred to herein as "xylitol lipid analogs", and "xylitol-headgroup lipid analogs"), specifically xylitol-headgroup analogs of palmitoyl-oleoyl-phosphatidylglycerol (POPG), have been found to have potent anti-inflammatory and antiviral activity. These novel xylitol-headgroup analogs of POPG were synthesized by the inventor and varied in their hydrophobic chains. The importance of the hydrophobic portion of these bioactive phospholipids for activity is demonstrated in the examples herein. Synthesis of these xylitol lipid analogs was optimized for high chemical yield and efficiency and characterized by tandem mass spectrometry. The xylitol lipid analogs were tested in a variety of in vitro model systems and were determined to have antagonist activity against the activation of all toll-like receptors (TLRs) except for TLR6 and TLR 5. The xylitol lipid analogs were determined to inhibit RSV infection by binding to the virus and preventing viral entry into cells. As disclosed herein, the inventor has determined that the hydrophobic portions of the phospholipids can be modulated to tailor immune responses and can be used to prevent and/or treat inflammatory disease and condition such as RSV and its harmful side effects.

The novel xylitol lipid analogs of the present invention have the following characteristics: a phospholipid glycerol backbone, a xylitol polar headgroup, a phosphodiester bond linking the glycerol backbone to the xylitol polar headgroup, variable hydrophobic regions comprising two aliphatic chains of 14 to 18 carbons in length, wherein linkage between the aliphatic chains and the phospholipid glycerol backbone is an O-acyl linkage or an O-alkyl linkage, and further wherein the aliphatic chains contain 0 to 2 double bonds. The addition of the xylitol to diacylglycerol-phosphate, or the dialkylglycerol-phosphate, creates a chiral center at the 3 position of the xylitol, thus the resulting compounds are more specifically 3'R and 3'S mixtures of the headgroup xylitol. These novel xylitol lipid analogs include:

Dimyristoyl-phosphatidylxylitol (DMPX; also referred to as: sn-1-myristoyl, sn-2-myristoyl sn-3 glycerol phosphoxylitol);

14:0 Diether-phosphatidylxylitol (14:0 DEPX; also referred to as: sn-1-O-myristyl, sn-2-O-myristyl sn-3 glycerol phosphoxylitol);

Dipalmitoyl-phosphatidylxylitol (DPPX; also referred to as: sn-1-palmitoyl, sn-2-palmitoyl sn-3 glycerol phosphoxylitol);

Palmitoyl-oleoyl-phosphatidylxylitol (POPX; also referred to as: sn-1-palmitoyl, sn-2-oleoyly sn-3 glycerol phosphoxylitol);

16:1 Dipalmitoleoyl-phosphatidylxylitol (16:1 DPPX; also referred to as: sn-1-palmitoleoyl, sn-2-palmitoleoyl sn-3 glycerol phosphoxylitol);

Distearoyl-phosphatidylxylitol (DSPX; also referred to as: sn-1-stearoyl, sn-2-stearoyl sn-3 glycerol phosphoxylitol);

Dioleoyl-phosphatidylxylitol (DOPX; also referred to as: sn-1-oleoyl, sn-2-oleoyl sn-3 glycerol phosphoxylitol);

18:1 Diether-phosphatidylxylitol (18:1 DEPX; also referred to as: sn-1-O-octadecenyl, sn-2-O-octadecenyl sn-3 glycerol phosphoxylitol); and Dilinoleoyl-phosphatidylxylitol (DLPX; also referred to as: sn-1-linoleoyl, sn-2-linoleoyl sn-3 glycerol phosphoxylitol; also referred to herein as 18:2 DLPX).

The inhibitory activity of the lipids and compounds of the invention can be attributed to activation of the specific toll receptors, TLR1, TLR2, TLR3, TLR4, TLR6, TLR7, TLR8, TLR9 and TLR10. Accordingly, the present invention relates to a single species as well to homogeneous preparations of these xylitol lipid analogs, as well as various compositions comprising these xylitol lipid analogs, and the use of these xylitol lipid analogs and/or compositions thereof, for the prevention and/or treatment of inflammation, and particularly inflammation associated with the activation of TLR1, TLR2, TLR3, TLR4, TLR6, TLR7, TLR8, TLR9, TLR10, and infections, conditions and diseases related to such activation.

The present invention also relates to the use of these xylitol lipid analogs and/or compositions containing such xylitol lipid analogs, to prevent and/or treat viral infections, and more particularly, certain respiratory infections, including, but not limited to, respiratory syncytial virus (RSV) infection.

Currently, there are two approved clinical therapies for RSV, the antiviral Ribavirin, and a monoclonal antibody (mAb) given prophylactically that is specific to RSV, Palivizumab. Ribavirin is a broad-spectrum antiviral that interferes with viral RNA polymerase activity and inhibits inosine 5'-monophosphate dehydrogenase thereby effectively depleting the available intracellular nucleotides. Ribavirin must be administered as an aerosol over a period of 12-18 hours each day, 3-7 days a week. Ribavirin costs around $30,000 for 6 grams (one adult dose for one day) (Lexicomp, "Ribavirin (oral inhalation): Drug information."). The effect of Ribavirin in children has mixed results, and is more effective in adults (E. De Clercq, "Chemotherapy of respiratory syncytial virus infections: the final breakthrough," *Int. J. Antimicrob. Agents*, vol. 45, pp. 234-237, 2015).

Palivizumab was approved for use by the FDA in 1998 in order to prevent lower respiratory tract infections as a result of RSV infection in high-risk infant populations (E. Ce Clercq, 2015). Palivizumab prophylaxis does not offer complete protection and is only approved for use in premature infants or those born with underlying lung conditions. Although it has overall positive results in decreasing hospitalizations and future respiratory complications that stem from RSV infection in high-risk infants, it also is an expensive therapy. High-risk infants are dosed every 28 days resulting in 5-6 total Palivizumab intramuscular injections. Each dose is 15 mg/kg of body weight. For an average weight of 2.5 kg (5.5 lbs), 37.5 mg of Palivizumab is needed. Over the course of 6 injections (assuming a constant weight) a total of 225 mg of Palivizumab must be administered. At a cost of $1,484.61 per 50 mg the prophylactic alone would cost $6,680 and does not include the cost of hospital visits per dose (K. Neovius, et al. "Cost-effectiveness analysis of palivizumab as respiratory syncytial virus prophylaxis in preterm infants in Sweden," *Acta Paediatr.*, vol. 100, no. 10, pp. 1306-1314, October 2011; P. Manzoni, et al., "Optimal timing and dosing intervals of palivizumab in premature neonates: still some work to do.," *Pediatrics*, vol. 115, no. 5, pp. 1439-40; author reply 1440-1, May 2005).

Both Ribavirin and Palivizumab do not offer complete protection from RSV and come with high price tags. Because the prophylactic and antiviral are expensive and only offered to a select subset of people, they do not offer an ideal or practical way to combat RSV. The prominent respiratory pathogen, RSV, still demands innovative approaches to reduce/treat the harmful effects of this virus.

Pulmonary surfactant of the lung has important biophysical and innate immune functions. Surfactant contains both lipids and proteins which line the alveolar compartment of the lung, with lipids accounting for 90% composition by weight and proteins contributing 10% composition by weight (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009; M. Agassandian and R. K. Mallampalli, "Surfactant phospholipid metabolism," *Biochimica et Biophysica Acta-Molecular and Cell Biology of Lipids*, vol. 1831, no. 3. pp. 612-625, 2013; M. Numata, et al., "Anionic pulmonary surfactant lipid regulation of innate immunity.," *Expert Rev. Respir. Med.*, vol. 6, no. 3, pp. 243-6, 2012). The surfactant-specific proteins, SP-A and SP-D, are known to play a role in innate immunity and the inflammatory response while SP-B and SP-C regulate lipid adsorption to the air-liquid interface, which promotes surfactant film formation (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009; M. Agassandian and R. K. Mallampalli, "Surfactant phospholipid metabolism," *Biochimica et Biophysica Acta-Molecular and Cell Biology of Lipids*, vol. 1831, no. 3. pp. 612-625, 2013). The lipid class, phosphatidylcholine (PC), is the most abundant lipid found in pulmonary surfactant with Dipalmitoyl-phosphatidylcholine (DPPC), accounting for 70% of the PC lipid class which helps reduce surface tension at the air-liquid interface (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009).

The next most abundant lipid class found in pulmonary surfactant is phosphatidylglycerol (PG). PG accounts for between 7% and 18% of surfactant lipids and up until recently, the role of PG in surfactant was unclear (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009; M. Agassandian and R. K. Mallampalli, "Surfactant phospholipid metabolism," *Biochimica etBiophysica Acta-Molecular and Cell Biology of Lipids*, vol. 1831, no. 3. pp. 612-625, 2013). Although PG is a minor lipid in pulmonary surfactant, it can reach levels of up to 3 mg/mL in the lung airways, the only abundant source of PG in mammals (J. F. Lewis and A. H. Jobe, "Surfactant and the adult respiratory distress syndrome.," *Am. Rev. Respir. Dis.*, vol. 147, no. 1, pp. 218-33, 1993).

Recent studies have revealed a new role for palmitoyl-oleoyl-phosphatidylglycerol (POPG), as a novel regulator of inflammation (M. Numata, et al., "Anionic pulmonary surfactant lipid regulation of innate immunity.," *Expert Rev. Respir. Med.*, vol. 6, no. 3, pp. 243-6, 2012). POPG exhibits potent antagonist activity of the activation of TLRs 1, 2, 3, 4, 6, 7 and 8 and suppresses inflammatory responses in airways and alveoli (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009; P. Kandasamy, et al., "Pulmonary surfactant phosphatidylglycerol inhibits *Mycoplasma pneumoniae*-stimulated eicosanoid production from human and mouse macrophages," *J. Biol. Chem.*, vol. 286, no. 10, pp. 7841-7853, 2011; M. Numata, et al., "Anionic pulmonary surfactant lipid regulation of innate immunity.," *Expert Rev. Respir. Med.*, vol. 6, no. 3, pp. 243-6, 2012). The lungs are continuously exposed to the external environment with each breath and must suppress an immune response until one is needed. Suppression of unnecessary inflammation allows for efficient gas exchange and prevents damage to airway epithelium. Because POPG has demonstrated the ability to antagonize TLRs and suppress inflammatory responses, it could have a therapeutic role against damaging inflammation from pulmonary disease.

Not only does POPG regulate inflammatory responses in the lungs, but it also has been shown to have antiviral activity against RSV. POPG acts as a decoy receptor and is able to bind to surface proteins of RSV thereby preventing attachment of RSV to epithelial cells (M. Numata, et al., "Pulmonary surfactant phosphatidylglycerol inhibits respiratory syncytial virus-induced inflammation and infection.," *Proc. Natl. Acad. Sci. U.S.A.*, vol. 107, no. 1, pp. 320-5, 2010; M. Numata, et al., "Phosphatidylglycerol provides short-term prophylaxis against respiratory syncytial virus infection.," *J. Lipid Res.*, vol. 54, no. 8, pp. 2133-43, 2013). As a common viral pathogen with serious and harmful side effects and limited prophylactic options and no current vaccine, RSV needs concentrated study and innovative approaches for development of new reagents for the prevention and treatment of viral infections.

The inventor has discovered that the minor pulmonary surfactant lipid, POPG, is a regulator of inflammation and has potent antiviral properties (K. Kuronuma, et al., "Anionic pulmonary surfactant phospholipids inhibit inflammatory responses from alveolar macrophages and U937 cells by binding the lipopolysaccharide-interacting proteins CD14 and MD-2," *J. Biol. Chem.*, vol. 284, no. 38, pp. 25488-25500, 2009; P. Kandasamy, et al., "Pulmonary surfactant phosphatidylglycerol inhibits *Mycoplasma pneumoniae*-stimulated eicosanoid production from human and mouse macrophages," *J. Biol. Chem.*, vol. 286, no. 10, pp. 7841-7853, 2011; M. Numata, et al., "Pulmonary surfactant phosphatidylglycerol inhibits respiratory syncytial virus-induced inflammation and infection.," *Proc. Natl. Acad. Sci. U.S.A*, vol. 107, no. 1, pp. 320-5, 2010; M. Numata, et al., "Phosphatidylglycerol suppresses influenza A virus infection.," *Am. J. Respir. Cell Mol. Biol.*, vol. 46, no. 4, pp. 479-87, April 2012; M. Numata et al., "Anionic pulmonary surfactant lipid regulation of innate immunity.," *Expert Rev. Respir. Med.*, vol. 6, no. 3, pp. 243-6, 2012; M. Numata, Y, et al., "Phosphatidylglycerol provides short-term prophylaxis against respiratory syncytial virus infection.," *J. Lipid Res.*, vol. 54, no. 8, pp. 2133-43, 2013) and have shown that POPG acts as an antagonist of the activation of TLRs 1, 2, 3, 4, 6, 7 and 8. POPG blocks infection of epithelial cells by RSV and influenza A Virus (IAV) in vitro, and protects the mice against RSV and IAV infection in vivo. However, POPG has a very short half-life in mice, $t^{1/2}$~45 minutes, making therapeutic, in vivo studies challenging.

The inventor has assessed the activity of POPG homologs as TLR2 and TLR4 antagonists (P. Kandasamy, et al., "Structural analogs of pulmonary surfactant phosphatidylglycerol inhibit toll-like receptor 2 and 4 signaling," *J. Lipid Res.*, vol. 57, no. 6, pp. 993-1005, 2016). The glycerol headgroup was replaced with a variety of primary alcohols while the hydrophobic portions (palmitoyl-oleoyl-diacylglycerol) of the molecule remained identical to POPG. These findings demonstrated that the headgroup of the phospholipid can be manipulated to produce differential antagonism of the TLR receptors. However, the study did not address the contribution of the hydrophobic portions of the phospholipid to antiviral specificity and activity.

As provided in the Examples herein, synthesis and analysis of xylitol-headgroup phospholipids for anti-inflammatory and antiviral activity in vitro is demonstrated. Many of the compounds exhibited activity against the activation of TLRs as well as in preventing RSV infection of cells. The compound 18:1 DEPX demonstrated the ability to suppress the activation of TLRs 1, 2, 3, 4 and 7 and exhibited high antiviral activity against RSV infection of cells. This compound was designed specifically to evade cleavage by lipases because its hydrophobic chains are attached to the glycerol backbone through an ether linkage. Because this molecule demonstrated considerable bioactivity, most notable the ability to inhibit RSV infection of cells, and because it is resistant to cleavage by lipases, it was chosen for further exploration in mouse model systems. The diether xylitol lipid compound was evaluated for turnover in the mouse lung, induction of inflammatory cell infiltration into the lungs after intranasal inoculation and its ability to protect the mouse lung from RSV infection.

In vitro immunoregulatory activity of xylitol-headgroup lipid analogs was assessed in multiple ways. Many of the analogs were effective antagonists against multiple TLRs and the effective lipids in each TLR experiment varied. A comprehensive table of xylitol antagonist activity with the cutoff being greater than a 50% reduction in cytokine secretion compared to activating TLR ligand alone is shown in Table 1.

TABLE 1

Summary of xylitol lipid TLR-dependent antagonist activity

|  |  | TLR2 | TLR3 | TLR2/1 | TLR2/6 | TLR7 | TLR9 | TLR5 |
|---|---|---|---|---|---|---|---|---|
| DMPX | PX (14:0/14:0) | + | − | − | − | − | − | − |
| 14:0 DEPX | PX (14:0e/14:0e) | + | + | + | − | + | − | − |
| DPPX | PX (16:0/16:0) | − | + | − | − | − | − | − |
| POPX | PX (16:0/18:1) | + | + | + | − | + | + | − |
| 16:1 DPPX | PX (16:1/16:1) | + | − | + | − | + | − | − |
| DSPX | PX (18:0/18:0) | − | + | − | − | − | − | − |

TABLE 1-continued

Summary of xylitol lipid TLR-dependent antagonist activity

|  |  | TLR2 | TLR3 | TLR2/1 | TLR2/6 | TLR7 | TLR9 | TLR5 |
|---|---|---|---|---|---|---|---|---|
| DOPX | PX (18:1/18:1) | + | + | + | − | + | + | − |
| 18:1 DEPX | PX (18:1e/18:1e) | + | + | + | − | + | − | − |
| 18:2 DLPX | PX (18:2/18:2) | + | − | + | − | + | + | − |

The PX lipids that were effective in suppressing TLR 4 activation in the presence of LPS were unsaturated lipids, or were saturated but did not contain more than 14 carbons in their hydrophobic chains. This result indicated that the length of carbon chains as well as degree of unsaturation played a role inhibiting TLR 4 activation. Assessment of the potency of PX lipids compared to POPG revealed four xylitol analogs with more potent antagonist activity than POPG.

Xylitol-headgroup analogs also were assessed for activity in modulating TLR 3 signaling. All analogs effectively suppressed TLR 3 activation in the presence of poly I:C except for DMPX, 16:1 DPPX and 18:2 DLPX. DMPX is a 14-carbon chain saturated lipid while 16:1 DPPX has 16 carbon chains with one double bond, and 18:2 DLPX has 18 carbon chains with two double bonds. There does not appear to be a pattern for effective antagonists against TLR 3. Notably, the lipids that were effective against TLR 4 were not necessarily effective against TLR 3. This result supports the development of phospholipid antagonists that can be designed to have activity specifically against one TLR and not others. Also, the lipid 16:1 DPPX appeared to be either a super agonist for TLR 3 activation or activated downstream signaling and robust proinflammatory cytokine secretion through another receptor. Because a pattern was not recognized among successful PX antagonist lipids, they were assessed for binding to TLR 3 ectodomain as a means to predict activity. However, all xylitol analogs bound to TLR 3 protein with moderate affinity and there were no meaningful differences between binding of different lipids that conferred activity.

Analogs were tested for antagonism of TLR 2 activation in conjunction with either TLR 1 or TLR 6. Multiple analogs suppressed TLR 2/1 activation including, 14:0 DEPX, POPX, 16:1 DPPX, DOPX, 18:1 DEPX and 18:2 DLPX. In contrast, none of the xylitol analogs were effective against TLR 2/6. TLR 2 is the general detector of pathogens within the heterodimers and binds two lipid hydrophobic chains, whereas TLR 1 has a lipid-binding pocket, but that pocket is not functional in TLR 6. The xylitol headgroup on the phospholipids might be too large to bind in the available pocket within TLR 6, but could bind TLR 1 because the pocket is relatively open and not hindered by large amino acids. Several saturated xylitol phospholipids were inactive against TLR 2/1, but 14:0 DEPX showed significant activity. 14:0 DEPX has two saturated chains that are 14 carbons in length, but they are attached to the glycerol backbone by ether linkage. This result demonstrates that not only is the hydrophobic portion of the molecule important for activity, but the chemical linkage to the glycerol backbone also influences activity and could be another important way to tailor molecules to a desired response against TLRs.

Xylitol analogs that demonstrated activity against TLR 2/1 also demonstrated antagonist activity against the activation of TLR 7. The saturated PX lipids were ineffective at suppressing TLR 7 signaling by polyU. Only three xylitol analogs were effective against TLR 9 activation, POPX, DOPX and 18:2 DLPX. Each of these lipids is unsaturated and contains at least one fatty acid with 18 carbons in length.

In order to determine whether xylitol lipids have adverse effects on cells by disrupting membrane dynamics, PX lipids were tested for antagonism of TLR 5 activation. TLR 5 is the only TLR that recognizes an unmodified protein, and none of the xylitol analogs inhibited TLR 5 activation. This result indicates that cell surface signaling is functional in the presence of PX lipids. Furthermore, the finding that a single xylitol lipid is not an effective antagonist across all TLRs, supports a conclusion that these lipids interact specifically with TLR complexes and inhibit, or in some cases, activate downstream signaling. Xylitol lipid analogs were also tested for their anti-RSV activity in vitro. Multiple PX lipids were highly effective and inhibited RSV infection by a 3-log unit reduction in plaque formation. The saturated PX lipids, DMPX, DPPX and DSPX, were determined to have moderate antiviral activity, whereas the ether-linked saturated lipid, 14:0 DEPX was ineffective at preventing RSV infection. The addition of a double bond in the hydrophobic chains of xylitol phospholipids appears to be important for antiviral activity against RSV. None of the saturated lipids were overly effective as antivirals, and an ether-linkage within the molecule hinders activity. The ester-linked, DMPX, had moderate antiviral activity whereas the ether-linked, 14:0 DEPX, was ineffective. The only difference between the two compounds is the link through which their hydrophobic chains are attached to the glycerol backbone.

A solid phase lipid-binding assay to RSV was used to survey the potential for a large-scale high throughput method to detect potential antiviral agents. However, because binding of solid phase lipid to RSV did not correlate well with antiviral activity, this assay may not be a useful high throughput screen to identify future antivirals. A subset of lipids with differing antiviral effectiveness was tested for inhibition of RSV attachment to cells. This assay was more indicative of antiviral activity, except for the ineffective antiviral, 14:0 DEPX. 14:0 DEPX did not inhibit plaque formation by RSV, but paradoxically appears to prevent viral binding to cells. The plaque assay was performed at 37° C. to assess antiviral activity, whereas viral binding to cells was performed at 18° C. Although the transition temperature of this molecule is unknown, from previous results during synthesis experiments I estimated the transition temperature of this ether lipid to be between 22° C. and 37° C. Synthesis of analogs progressed much better at temperatures above the starting material transition temperature. At 18° C., 14:0 DEPX could be in the rigid gel phase which aided in impeding viral attachment to cells, however at 37° C. the lipid would be in the liquid-crystalline phase changing the dynamic of its activity. This difference in physical state could be one possible explanation of apparent temperature dependence for 14:0 DEPX antiviral activity.

Taken together, the results from these in vitro experiments indicate that xylitol lipids are viable anti-inflammatory agents that have specific activity against TLRs. This activity can be modulated by changing the length and degree of unsaturation of hydrophobic chains of these molecules, as well as the linkage of hydrophobic chains to the glycerol backbone. Xylitol analogs also demonstrate significant antiviral activity against RSV where unsaturated compounds were more effective than saturated compounds. Xylitol-headgroup analogs can be used to develop therapeutics against harmful inflammatory diseases and protect the host against infection from RSV, a virus that demands innovative new approaches to combat its harmful effects.

As further demonstrated in the Examples below, a diether lipids with a xylitol polar headgroups have an increased half-life in the mouse lung compared to POPG. The half-life of 18:1 DEPX in the mouse lung was determined to be around 24 hours. The reason for the extended half-life is believed to be two-fold. First the xylitol headgroup might not be recognized easily by lipases in the lung, delaying metabolism of the headgroup. Second, the diether linkage of the hydrophobic chains to the glycerol backbone is resistant to lipase cleavage. 18:1 DEPX also was demonstrated to persist in the mouse lung when low amounts of lipid were introduced.

When assessing inadvertent toxicity of 18:1 DEPX high amounts of the lipid were not well tolerated. Significant amounts of cellular infiltrates when compared to control mice were found in mice that received ≥300 μg 18:1 DEPX. Also, cell populations among mice that received 18:1 DEPX generally had a greater number of neutrophils within the lung than mice that did not receive xylitol lipid. For the same reasons why this lipid has an extended half-life in the lung, these features could translate into toxicity. Xylitol is a sugar-alcohol that is commercially used as a sweetener. Xylitol itself is not heavily metabolized, but is well tolerated in the body (K. Amo, et al., "Effects of xylitol on metabolic parameters and visceral fat accumulation.," *J. Clin. Biochem. Nutr*., vol. 49, no. 1, pp. 1-7, July 2011). Although diether phospholipids typically are not found in humans, they have been identified in archaea (D. Gmajner, et al., "Structural characterization of liposomes made of diether archaeal lipids and dipalmitoyl-L-α-phosphatidylcholine," *Biophys. Chem*., vol. 158, no. 2, pp. 150-156, 2011). The combination of a xylitol headgroup along with a diether link that is not present in mammals could confer toxicity to the molecule at high concentrations. However, many potent pharmacologic molecules have a narrow therapeutic window before they become toxic (J. Tamargo, et al., "Narrow therapeutic index drugs: a clinical pharmacological consideration to flecainide.," *Eur. J. Clin. Pharmacol*., vol. 71, no. 5, pp. 549-67, May 2015).

Results reveal that 18:1 DEPX has a protective effect on the mouse lung in the presence of RSV infection. After the initial weight loss, mice were healthy enough to consume food and actively move around the cage. 18:1 DEPX also reduced cellular infiltrates and INFγ in the lung compared to RSV alone mice and inhibited RSV infection as assessed by both plaque assay and qRT-PCR. It is possible that 18:1 DEPX can aid in immediate recruitment of a small number of immune cells into the lung before innate immune receptors detect and respond to RSV. The slight toxic effect of the lipid alone resulting in increased neutrophils within the lung can aid in more efficient resolution of the virus in combination with its antiviral properties observed in vitro. This can be tested by comparing pretreatment of mice with 18:1 DEPX followed by infection with RSV, to RSV+18:1 DEPX simultaneous delivery, to post treatment of mice with 18:1 DEPX 6-12 hours following viral infection.

In addition, it is contemplated herein that, 18:1 DEPX can be used in combination with POPG for optimal protection against RSV. A mixture of 18:1 DEPX with POPG has the potential to change the rate at which POPG is turned over and perhaps in turn POPG can dampen the inflammation excited by 18:1 DEPX.

Because of the results from MALDI imaging studies with 18:1 DEPX, it is now known that intranasal inoculation is a viable method for lipid delivery that distributes throughout the lung. 18:1 DEPX was distributed similarly to surfactant lipids within the lung proving that the lipid did not only reside in the large airways. Recently liposome delivery of RNAi therapy against RSV was assessed as a nasal spray in a randomized controlled trial with a positive outcome (J. DeVincenzo, et al., "A randomized, double-blind, placebo-controlled study of an RNAi-based therapy directed against respiratory syncytial virus," *Proc. Natl. Acad. Sci*., vol. 107, no. 19, pp. 8800-8805, May 2010). These results collectively support an intranasal delivery of liposome therapies that need to reach airways as well as alveolar compartments within the lung.

As provided for in Example 1, utilizing PLD purified from Savoy cabbage, a novel class of phospholipid, phosphatidylxylitol (PX), was synthesized. Nine phospholipids with a xylitol polar headgroup and varying hydrophobic chains were synthesized for structure/function analysis in this thesis. The xylitol compounds were successfully purified using normal phase HPLC. Structures of all compounds were confirmed with tandem mass spectrometry and characterized for their unique collision induced decomposition (CID) mass spectra. PX lipids are anionic and therefore, make abundant negative ions [M-H]− within the mass spectrometer in negative ion mode. Xylitol analogs all exhibit two common transitions during CID, neutral loss of 134 corresponding to the xylitol headgroup and an ion with m/z 213. These unique identifiers of xylitol lipids can be used as multiple reaction monitoring (MRM) transitions and can detect xylitol analogs in a complex mixture without prior separation techniques, so that PX lipids can be monitored for tissue uptake and metabolism by unique mass and CID fragmentation.

As provided for in Example 2, expanding on the discovery that the minor surfactant lipid, POPG, possessed anti-inflammatory and antiviral activity, xylitol lipid analogs were synthesized to better understand the structure/function relationship of the phospholipid. Xylitol-headgroup analogs were assessed for toll-like receptor (TLR)-dependent anti-inflammatory activity as well as their antiviral activity against RSV in multiple in vitro models. All analogs except for the saturated PX lipids that had ≥16 carbon chains were effective at antagonizing the activation of TLR 4 in the presence of the agonist, LPS. Four xylitol compounds, POPX, DOPX, 18:1 DEPX and 18:2 DLPX were more potent antagonists of TLR 4 activation than POPG.

There were no consistent, recognizable structural patterns for lipids that were effective at suppressing TLR 3 activation. DMPX, 16:1 DPPX and 18:2 DLPX were ineffective antagonists of TLR 3. A biochemical assay of lipid solid phase binding to TLR 3 ectodomain was determined not to coincide with activity and has poor predictive value for large-scale screening. None of the ester-linked saturated lipids suppressed TLR 2/1 activated by Pam3Cys, potentially highlighting ether-linked hydrophobic chains as an additional way to confer specificity of action and not just extend half-life. Lipids that were effective antagonists against TLR 2/1 were also effective against TLR 7. No xylitol compounds had an effect on TLR 2/6 or TLR 5 signaling. POPX, DOPX and 18:2 DLPX were the only effective antagonists of TLR 9 activation.

Xylitol analogs fell into three groups when tested for antiviral activity against RSV assessed by quantitative plaque assay. POPX, 16:1 DPPX, DOPX, 18:1 DEPX and 18:2 DLPX were all highly effective antivirals, reducing RSV plaque formation by at least a factor of 3 log units. The saturated lipids, DMPX, DPPX and DSPX all exhibited modest anti-RSV activity and reduced plaque formation by a factor of 1 log unit. 14:0 DEPX was ineffective and did not inhibit RSV infection. The activity of solid phase lipids to bind to RSV was tested biochemically. Results indicate that binding to the virus in this assay does not correlate with antiviral activity of the compound. A much more predictive assay for anti-RSV activity was the ability of lipid to interfere with RSV binding to the epithelial cell surface. The highly effective antivirals POPX, 16:1 DPPX and 18:1 DEPX prevented RSV attachment to HEp2 cells, whereas the moderately effective antiviral DPPX did not. Although 14:0 DEPX did not have antiviral activity as determined by plaque assay, it prevented RSV from binding to the cell surface. There may be a temperature-dependent effect allowing 14:0 DEPX to block viral attachment to the cell surface at 18° C.

As provided for in Example 3, the compound 18:1 DEPX was found to be an effective antagonist against the activation of TLRs 1, 2, 3, 4 and 7, and a highly effective antiviral as determined in vitro; and thus was chosen for further study in vivo. 18:1 DEPX is a diether-linked phospholipid that was synthesized to evade cleavage by lipases. 18:1 DEPX has a long half-life in mice, where 50% of the starting material was recovered after 24 hours. 18:1 DEPX was assessed for toxicity within the mouse lung determined by cellular infiltration 24 hours after inoculation. Doses of 18:1 DEPX≥300 µg/mL were accompanied with significant cellular infiltrates compared with a PBS control, and induced influx of high numbers of neutrophils. Because of these results, 100 µg/mL 18:1 DEPX was chosen as the dose to determine if this lipid protects the mouse lung from RSV infection. During viral challenge there was no difference in body weight loss in control mice, 18:1 DEPX mice and 18:1 DEPX+RSV mice. There was a significant difference in percent body weight loss between the control group and RSV group on days 4 and 5, indicating the RSV mice were sick. On day 5 the mice were sacrificed and BALF was collected and assessed for cell infiltration into the lungs and IFNγ levels in BALF. The 18:1 DEPX+RSV group had significantly lower amounts of cellular infiltrates and IFNγ than the mice infected with RSV alone. Also, 18:1 DEPX+RSV mice had a reduced viral load determined by plaque assay as well as by qPCR compared to RSV mice. The compound, 18:1 DEPX was administered to mice, and matrix assisted laser desorption ionization (MALDI) imaging was used to determine distribution of compound and retention within the lungs. Test results confirmed 18:1 DEPX rapidly disperses throughout the lung upon intranasal inoculation, and was retained mainly in the recoverable compartments of the lung with only a small amount retained in the tissue. The rapid dispersion upon inhalation in mice supports the idea that this compound could have preventive and therapeutic utility in humans.

According to the present invention, an compositions containing an "effective amount" of an xylitol lipid analog or related compound of the invention contain an amount of the specific xylitol lipid analog or related compound effective to inhibit an inflammatory process in vitro or in vivo, or to inhibit viral infection in vitro or in vivo, as measured by any suitable technique for measuring such activity, several of which are described herein. Effective amounts of xylitol lipid analogs or related compounds of the invention to be included in a composition are described in more detail below.

In one aspect of the invention, the xylitol lipid analog or related compounds are provided in a homogeneous lipid preparation comprising, consisting essentially of, or consisting of one or more of the xylitol lipid analogs described above, and/or derivatives of any of such xylitol lipid analogs or related compounds. In one embodiment, any of the above-described lipid preparations further comprise any other lipid or lipid derivative that is useful in a surfactant preparation, useful in a therapeutic preparation, and/or useful for stabilizing the bilayer of lipids in a lipid preparation and/or decreasing leakage of encapsulated material. In one embodiment, any of the above-described lipid preparation further comprise antioxidants, which are useful for inhibiting oxidation of the lipids in lipid preparation.

According to the invention, a lipid preparation useful in the invention can include any stabilized form of lipid that would be useful in a method of the invention, and particularly, any lipid that is stabilized by protein or another suitable compound. For example, lipid preparations useful in the invention include, but are not limited to, liposomes, and protein-stabilized lipid forms (e.g., non-liposomal lipids stabilized by the use of a lipoprotein, e.g., see NANODISC™, Nanodisc, Inc.).

According to the present invention, a liposome (also referred to as a liposomal preparation or liposomal composition) is a spherical, microscopic artificial membrane vesicle consisting of an aqueous core enclosed in one or more phospholipid layers. Liposomes can also be generally defined as self closed spherical particles with one or several lipid membranes. Liposomes can be composed of naturally-derived phospholipids with mixed fatty acid chains or prepared from synthetic lipids with well-defined lipid chains. Depending on the number of the membranes and size of the vesicles, liposomes are considered to be large multilamellar vesicles (LMV) with sizes up to 500 nm, small unilamellar vesicles (SUV) with sizes <100 nm, and large unilamellar vesicles (LUV) with sizes >100 nm. Liposomes and liposome preparation methods are well known in the art, and several example of liposomes useful in the present invention, as well as methods of producing such liposomes and compositions comprising such liposomes, is described in the Examples. A stabilized lipid, such as a protein- or lipoprotein-stabilized lipid, can be prepared using any method known in the art.

In one exemplary embodiment, the lipid in the lipid preparation is composed of one xylitol lipid analog disclosed herein. Similarly, lipid preparations can be composed of any of xylitol lipid analog disclosed herein, in combination with one or more different phospholipids and/or other lipid(s) and/or related compounds.

Preferred compositions for use in the invention provide an amount of the xylitol lipid analogs or related compounds described as useful in the present invention to provide a therapeutic or anti-inflammatory or anti-pathogen (e.g., antiviral) effect when administered to an individual. For example, as discussed above, prior to the present invention, the presence of effective xylitol lipid analogs of the invention, in commercial surfactant preparations (including those derived from biological sources, such as porcine or bovine surfactant) has not, to the inventor's knowledge, had any demonstrable effect as an anti-inflammatory or anti-viral agent. This is because surface dilution and randomization of the effective phospholipids of the invention within a single vesicle of lipids significantly diminishes the potency of the lipid. As the Examples illustrate, in order to approximate the activity of the xylitol lipid analog alone, randomized phospholipids of the invention must constitute nearly 50% of the total lipid present in a surfactant lipid-containing vesicle. However, if provided as a separate, homogeneous lipid preparation, even when admixed with other lipids after production of the lipid preparation, the xylitol lipid analog of the invention can be provided in smaller quantities.

Therefore, several different compositions of the xylitol lipid analogs or related compounds described herein are envisioned for use in the invention. In one embodiment, the invention provides a homogeneous lipid preparation consisting of a xylitol lipid analog. As used herein, a "homogeneous" lipid preparation consisting of a specified xylitol lipid analog or related compound or combination of specified xylitol lipid analog, means that the lipid preparation (e.g., the lipid vesicles or smaller portions) contains only the specified xylitol lipid analog or related compound or a combination of specified xylitol lipid analogs or related compounds (e.g., a pure preparation of the specified phospholipid(s)), and is substantially or completely free of other phospholipids or other lipids. A homogeneous preparation of a specified xylitol lipid analog or related compound can contain other non-lipid agents, if desired, such as antioxidants, a targeting moiety (described below), or another therapeutic agent (e.g., a protein, and antibody, a small molecule or drug). A homogeneous lipid preparation of the invention can be provided alone or with a pharmaceutically acceptable carrier, including an excipient or buffer, or in a composition with other agents or lipid preparations.

It is one embodiment of the invention to administer a homogeneous lipid preparation of an xylitol lipid analog of the invention in the absence of any other lipids, although in other embodiments, the additive effects of other lipids, such as other lipids contained in surfactant, may be desirable and useful. In these alternate embodiments, the invention provides compositions that allow for the provision of such additional lipids and/or combinations of lipids, without losing the effectiveness of the particular anionic lipids or related compounds described herein. Such compositions are described below. Accordingly, in one aspect of the invention, the composition comprises other lipid preparations.

In one embodiment, the invention provides a composition comprising a homogeneous lipid preparation of the xylitol lipid analogs of the invention and at least one additional agent. The additional agent can include any pharmaceutical carrier, as discussed above, or an additional agent for the treatment of inflammation or pathogen infection (e.g., an anti-viral agent), for example.

Suitable anti-inflammatory agents include, but are not limited to, cytokine inhibitors, chemokine inhibitors, chemoattractant inhibitors, Cox inhibitors, leukotiene receptor antagonists, leukotriene synthesis inhibitors, inhibitors of the p38 MAP kinase pathway, glucocorticoids. More specifically, anti-inflammatory compounds can include, but are not limited to: any inhibitor of eicosanoid synthesis and release, including any Cox-2 inhibitor; Cox-1 inhibitors; inhibitors of some certain prostaglandins (prostaglandin E(2); PGD(2)), inhibitors of certain leukotrienes (LTB$_4$); classes of antibiotics with known direct or indirect anti-inflammatory effects, including macrolides (e.g. azithromycin) and fluoroquinolones (e.g., levofloxacin; moxifloxacin; gatifloxacin); inhibitors of p38 MAP kinase; inhibitors of the function of pro-inflammatory cytokines and chemokines, including antagonists of tumor necrosis factor (TNF), antagonists of interleukin-8 (IL-8); transforming growth factor beta (TGF-beta), β-agonists (long or short acting), antihistamines, phosphodiesterase inhibitors, corticosteroids, and other agents.

According to the present invention, a "pharmaceutically acceptable carrier" includes pharmaceutically acceptable excipients and/or pharmaceutically acceptable delivery vehicles, which are suitable for use in the administration of a preparation, formulation or composition, including a liposomal composition or preparation, to a suitable in vivo site. A suitable in vivo site is preferably any site wherein inflammation or infection by a pathogen, for example, is occurring or is expected to occur. Preferred pharmaceutically acceptable carriers are capable of maintaining a formulation of the invention in a form that, upon arrival of the formulation at the target site in a patient (e.g., the lung tissue), the formulation is capable of acting at the site, preferably resulting in a beneficial or therapeutic benefit to the patient. A delivery vehicle for a protein or agent can include the lipid preparation itself, if another agent is included, although in most embodiments of the invention, the lipid preparation is also a therapeutic agent as described herein (e.g., the lipid preparation can serve one or both functions).

Suitable excipients of the present invention include excipients or formularies that transport or help transport, but do not specifically target, a composition or formulation to a cell or tissue (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

A lipid preparation useful in the present invention can be modified to target to a particular site in a patient, thereby targeting and making use of the xylitol lipid analogs and any agents carried by the lipid preparation at that site. Suitable modifications include manipulating the chemical formula of the lipid preparation and/or introducing into the lipid preparation a targeting agent capable of specifically targeting the lipid preparation to a preferred site, for example, a preferred cell type. Suitable targeting agents include ligands capable of selectively (i.e., specifically) binding another molecule at a particular site. Examples of such ligands include antibodies, antigens, receptors and receptor ligands.

In one embodiment, a composition suitable for use in the invention comprises a preparation (e.g., a lipid preparation) of randomly mixed surfactant phospholipids or lipids (e.g., any combination of lipids found in surfactant), combined with (added to, mixed gently with, in admixture with) a homogeneous lipid preparation of the anionic lipids or related compounds useful in the present invention. In this embodiment, the combining of the randomly mixed lipids with the homogeneous lipid preparation of the xylitol lipid analogs is performed in a manner that does not result in significant fusion and/or intermixing of lipids between the vesicle bilayers (e.g., between the randomly mixed lipid preparations and the pure or homogeneous lipid preparation of xylitol lipid analogs. By producing a homogeneous preparation of the desired xylitol lipid analogs and then adding it to another preparation of lipids, such as a randomized surfactant preparation, the inventor has discovered that the biological activity of the xylitol lipid analogs described herein (e.g., anti-inflammatory, anti-pathogen, including anti-viral) is maintained. In this embodiment of the invention, it is preferred that the homogeneous lipid preparations of the xylitol lipid analogs of the invention comprise at least 1% of the total lipids in the composition (e.g., the total lipids being those present in the homogeneous preparation and the added randomly mixed surfactant preparation), or at least 5%, or at least 10%, or at least 15%, or at least 20%, or at least 25%, or at least 30%, or at least 35%, or at least 40%, or at least 45%, or at least 50%, of the total lipids in the composition.

In another embodiment of the invention, a preparation of randomly mixed lipids is provided, and preferably a preparation of randomly mixed surfactant lipids and phospholipids, wherein the preparation contains one or more xylitol lipid analogs useful in the present invention as described above. In this embodiment, the xylitol lipid analogs comprises at least about 30% of the total lipids in the randomly mixed surfactant lipids, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, of the total lipids in the randomly mixed surfactant lipids (or any amount between at least 30% and 100%, in whole number increments, e.g., 30%, 31%, 32%, etc.).

Preparations of randomly mixed lipids, including randomly mixed surfactant lipids can be made using techniques known in the art and are also available commercially (e.g., see Exosurf® (Wellcome, USA, an artificial surfactant preparation); Alveofact® (Thomae, Germany, prepared from bovine BAL); Curosurf® (Chiesi, Italy, prepared from minced porcine or bovine lung tissue) or Survanta® (Abbott, USA, prepared from minced porcine or bovine lung tissue)). Lung surfactant is a complex mixture of various phospholipids, neutral lipids and apoproteins (Doles, *Ann Rev Med* 1989; 40: 431-446; Jobe, *N Engl J Med* 1993; 328: 861-868; Tegtmeyer et al., *Eur Respir J,* 1996, 9, 752-757). Surfactant replacement therapy has proven to be beneficial for the treatment of the neonatal respiratory distress syndrome (Jobe, supra), and is also considered as a therapeutic option for term infants and adults with acute respiratory failure (Lewis and Jobe, *Am Rev Respir Dis* 1993; 147:216-233). Accordingly, surfactant lipid preparations are widely available and well known to those of skill in the art. It is believed that the addition of the homogeneous lipid preparations of xylitol lipid analogs described herein to such preparations will significantly enhance the use of such commercial preparations or other surfactant preparations in the prevention and treatment of a variety of conditions, including those described directly above.

The total concentration of lipids to be delivered to an individual (e.g., to the lung) according to the present invention can range from about 5 μmol to about 1 mmol, including any amount between, in increments of 1 μmol. In one aspect, the amount delivered is from about 40 μmol to about 800 μM, although one of skill in the art can readily determine the appropriate amount to be delivered. By way of example, in one embodiment, the lipid preparation comprising a given xylitol lipid analog is delivered in an amount suitable to replace all resident lung PG). The estimated amount of unsaturated PG in the lung is approximately 400 umole in the entire adult lung residing in the alveolar compartment exclusive of the tissue. If the lipid preparation is to replace all resident lung PG, then 40 umol/ml×10 ml would be sufficient. It is an embodiment of the invention to provide the xylitol lipid analogs to the lung in an amount delivered that is equivalent to between about 10% of the total resident amount of the same or similar lipid, to about 200% of the total resident amount. Accordingly, from a lipid preparation that is 40 umol of the lipid or compound of the invention per ml of lipid preparation, the individual would receive between about 1 ml and 20 ml delivered in an aqueous suspension down the trachea, for delivery to the lungs.

In one embodiment, the lipid preparation useful in the present invention is complexed with another agent, such as a protein or a small molecule (drug), wherein the other agent is also useful for inhibiting or preventing inflammation or infection by a pathogen (e.g., a virus) in an individual. Methods of encapsulating or complexing proteins and other agents with lipids such as liposomes and protein-stabilized lipids are known in the art. The encapsulation efficiency of proteins by lipid preparations generally depends on interaction between the protein and the lipid bilayer or micelle. The protein entrapment can be increased by manipulation of the lipid preparation, or by increasing the lipid concentration, in order to favor electrostatic interactions, while monitoring the ionic strength of the protein solution (Colletier et al., *BMC Biotechnology* 2002, 2:9). Preferably, the amount of a protein complexed with lipid preparations will range from about 0.001 mg of protein per 1 ml lipid preparation to about 5 mg of protein per 1 ml lipid preparation.

Another embodiment of the invention relates to a method to produce a surfactant composition. The method includes (a) providing a homogeneous lipid preparation of an xylitol lipid analogs and/or related compound(s) as described herein and (b) adding the preparation of (a) to a preparation of randomly mixed surfactant lipids. The preparation of randomly mixed surfactant lipids can be produced by any suitable method known in the art or obtained commercially, as discussed above. Preferably, the preparation of (a) and/or (b) are in aqueous solution. Most preferably, the preparation is gently mixed to avoid significant fusion or intermixing of lipids between vesicle bilayers in (a) and (b), also as discussed above. In one aspect, the lipids in the preparation of (a) comprise at least 1% of the total lipids in the composition, or any amount from at least 1% to at least 50% or greater, in 1% increments.

One embodiment of the present invention relates to the use of any of the xylitol lipid analog formulations described herein, including combinations thereof, to treat or prevent inflammation or a pathogen infection, and particularly a viral infection (e.g., RSV). The preventative and/or therapeutic methods of the invention generally include the administration to an individual (any individual, including infants, children and adults), any one or more preparations of the xylitol lipid analogs and/or related compounds described herein, alone or in combination with other lipids or agents, and/or as a supplement to conventional surfactant preparations or other therapies.

In one embodiment, the methods of the invention are useful for preventing or inhibiting inflammation or a pathogen infection associated with particular toll-like receptors, and specifically, TLR1, TLR2, TLR3, TLR4, TLR6, TLR7, TLR8, TLR9 and/or TLR10. These TLRs have been associated, for example, with various bacterial infections, protozoan and fungal infections, viral infections e.g., Cytomegalovirus infection, Herpes simplex virus infection, measles, Varicella-zoster virus infection, HIV infection, rhinovirus infection, parainfluenza virus infection, Human parechovirus infection, influenza type A viral infection, Papilloma virus infection), cancer (including, but not limited to, melanoma), and autoimmune diseases. Accordingly, it is an embodiment of the invention to treat or inhibit inflammation associated with any of these conditions or to prevent or inhibit infection by a pathogen associated with any of these conditions.

One particular embodiment of the invention relates to a method to prevent or inhibit or reduce or treat infection by respiratory syncytial virus (RSV), as well as viral inflammation or infection by other viruses. The method includes the administration of any of the xylitol lipid analog and/or related compound formulations described herein, including combinations thereof, to an individual who has or who is at risk of being infected by a virus, and particularly a virus associated with any of the TLRs discussed above, and more particularly, with RSV. With regard to RSV, the preparation can be administered to newborn infants, including to any newborn infant, regardless of whether the viral infection has been detected in the infant (i.e., the invention is useful as a prophylactic and as a therapeutic approach). Preparations of the xylitol lipid analog and related compounds described herein can be used alone or in combination with other lipids or agents, and/or as a supplement to conventional surfactant preparations, to prevent and/or treat RSV infection.

The method of the invention is also useful for the prevention and/or treatment of other pulmonary infections and disorders, including in infants, children and adults, including, but not limited to, adult respiratory distress syndrome (ARDS), acute lung injury (ALI), viral infection associated with asthma, chronic obstructive pulmonary disease (COPD), pneumonia, bronchitis, tuberculosis, reactive airway disease syndrome, interstitial lung disease, rhinitis, and parasitic lung disease.

In accordance with the present invention, determination of acceptable protocols to administer a composition or formulation, including the route of administration and the effective amount of a composition or formulation to be administered to an individual, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, intestinal, intra-luminal, and parenteral routes. Preferred parenteral routes can include, but are not limited to, subcutaneous, intradermal, intravenous, intramuscular, intraarterial, intrathecal and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). Ex vivo refers to performing part of the administration step outside of the patient. Preferred routes of administration for antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, for example, Stribling et al., Proc. Natl. Acad. Sci. USA 189:11277-11281, 1992, which is incorporated herein by reference in its entirety). Carriers suitable for aerosol delivery are described above. Devices for delivery of aerosolized formulations include, but are not limited to, pressurized metered dose inhalers (MDI), dry powder inhalers (DPI), and metered solution devices (MSI), and include devices that are nebulizers and inhalers. Oral delivery can be performed by complexing a therapeutic composition of the present invention to a carrier capable of withstanding degradation by digestive enzymes in the gut of an individual. Examples of such carriers, include plastic capsules or tablets, such as those known in the art. Administration of a composition locally within the area of a target cell refers to injecting the composition centimeters and preferably, millimeters from the target cell or tissue.

In humans, it known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting an animal dosage to a human dosage using alometric scaling. For example, essentially, a scale of dosage from mouse to human is based on the clearance ratio of a compound and the body surface of the mouse. The conversion for mg/kg is $\frac{1}{12}$th of the "no observed adverse event level" (NOEL) to obtain the concentration for human dosage. This calculation assumes that the elimination between mouse and human is the same.

Preferred amounts of lipid preparations to be delivered to an individual have been discussed in detail above.

In one embodiment, an effective amount of a preparation of the invention to administer to an individual is an amount that measurably inhibits (or prevents) inflammation or infection by a pathogen in the individual as compared to in the absence of administration of the formulation. A suitable single dose of a formulation to administer to an individual is a dose that is capable of reducing or preventing at least one symptom, type of injury, or resulting damage, from inflammation or pathogen infection in an individual when administered one or more times over a suitable time period. Preferably, a dose is not toxic to the individual.

One of skill in the art will be able to determine that the number of doses of a preparation to be administered to an individual is dependent upon the extent of the inflammatory condition or infection by a pathogen and/or the anticipated or observed physiological damage associated with such inflammation or infection, as well as the response of an individual patient to the treatment. The clinician will be able to determine the appropriate timing for delivery of the formulation in a manner effective to reduce the symptom(s) associated with inflammation or pathogen infection in the individual. Preferably, the agent is delivered within 48 hours, and more preferably 36 hours, and more preferably 24 hours, and more preferably within 12 hours, and more preferably within 6 hours, 5 hours, 4 hours, 3 hours, 2 hours, or 1 hour, or even minutes after the recognition of a condition to be treated by a formulation of the invention; after an event that causes inflammation in an individual or infection of an individual, or that is predicted to cause inflammation in or infection of an individual, which can include administration prior to the development of any symptoms of inflammation or infection in the individual.

Methods and uses directed to therapeutic compositions of the invention are primarily intended for use in the prevention and/or treatment of a disease or condition. The term "protecting" can be generically used to convey prevention and/or treatment. A therapeutic composition of the present invention, when administered to an individual, can: prevent a disease from occurring; cure the disease; delay the onset of the disease; and/or alleviate (reduce, delay, diminish) disease symptoms, signs or causes (e.g., reduce one or more symptoms of the disease; reduce the occurrence of the disease; increase survival of the individual that has or develops the disease; and/or reduce the severity of the disease). As such, the invention includes both preventing disease occurrence (prophylactic treatment) and treating an animal that has a disease or that is experiencing symptoms of a disease (therapeutic treatment).

According to the present invention, the methods of the present invention are suitable for use in an individual that is a member of the Vertebrate class, Mammalia, including, without limitation, primates, livestock and domestic pets (e.g., a companion animal). Most typically, an individual will be a human individual. The term "individual" can be interchanged with the term "subject" or "patient" and refers to the subject of a method according to the invention. Accordingly, an individual can include a healthy, normal (non-diseased) individual, but is most typically an individual who has or is at risk of developing an inflammatory condition or an infection, including a viral infection, or a symptom or indicator thereof as described herein.

The following experimental results are provided for purposes of illustration and are not intended to limit the scope of the invention.

EXAMPLES

Example 1

This example describes the synthesis and characterization of xylitol-headgroup analogs.
Experimental Procedures:
Materials:
Phospholipids were purchased from Avanti Polar Lipids (Alabaster, Ala.):
1,2-dimyristoyl-sn-glycero-3-phosphocholine (14:0/14:0 PC),
1,2-di-O-tetradecyl-sn-glycero-3-phosphocholine (14:0/14:0 Diether PC),
1,2-dipalmitoyl-sn-glycero-3-phosphocholine (16:0/16:0 PC),
1-palmitoyl-2-oleoyl-sn-glycero-3-phosphocholine (16:0/18:1 PC),
1,2-dipalmitoleoyl-sn-glycero-3-phosphocholine (16:1/16:1 (Δ9-Cis) PC),
1,2-distearoyl-sn-glycero-3-phosphocholine (18:0/18:0 PC),
1,2-dioleoyl-sn-glycero-3-phosphocholine (18:1/18:1 (Δ9-Cis) PC),
1,2-di-O-(9Z-octadecenyl)-sn-glycero-3-phosphocholine (18:1/18:1 Diether PC),
1,2-dilinoleoyl-sn-glycero-3-phosphocholine (18:2/18:2 (Cis) PC),
1-O-octadecyl-2-O-methyl-sn-glycero-3-phosphocholine (Edelfosine).

Xylitol, phospholipase D from cabbage, 8-anilino-1-naphthalenesulfonic acid (ANSA) and diethyl ether were purchased from Sigma-Aldrich (St. Louis, Mo.). All other solvents are HPLC grade and were purchased from Thermo Fisher Scientific (Waltham, Mass.).
Transphosphatidylation Reaction:

A transphosphatidylation reaction with the enzyme phospholipase D (PLD) was utilized to synthesize analogs of POPG as previously described by S. F. Yang et al ("Transphosphatidylation by phospholipase D.," *J. Biol. Chem.*, vol. 242, no. 3, pp. 477-84, February 1967). PLD catalyzes the hydrolytic cleavage of terminal phosphate ester bonds of glycerophospholipids with a choline head group but in the presence of an excess of primary alcohol, catalyzes a transphosphatidylase reaction, which exchanges the choline head group for that of the primary alcohol. This method was used to synthesize analogs that contain a xylitol polar head group that differ in their hydrophobic chains.

Aliquots of 5-10 mg of phosphatidylcholine (PC) species in chloroform were dried under a stream of nitrogen gas. Diethyl ether was added to the dried PC species, and once again dried using nitrogen gas to eliminate all of the chloroform. Dried PC species were resuspended in 3.1 mL of diethyl ether. Xylitol at 40%-50% (w/v) was dissolved in a pH 5.5 sodium acetate buffer that contained 120 mM calcium chloride in a final volume of 500 µL. This aqueous solution was then added to the ether phase of the reaction followed by the addition of PLD at a final concentration of 120 units/mL. The reaction mixture was vortexed 18-24 hours at temperatures ranging from 22° C. to 42.5° C. Reactions were stopped by the addition of 50 µL 0.5 M EDTA. Ether was evaporated under a stream of nitrogen and the lipids were extracted using the Bligh-Dyer method ("A rapid method of total lipid extraction and purification.," *Can. J. Biochem. Physiol.*, vol. 37, no. 8, pp. 911-7, August 1959). Reaction progress was assessed using thin layer chromatography and visualized using 0.1% aqueous ANSA, followed by exposure to UV light.
High Performance Liquid Chromatography (HPLC):

Normal phase HPLC was used to purify xylitol lipids on a 150 mm×30 mm silica column. The HPLC solvents consisted of a stationary phase (solvent A) and a mobile phase (solvent B). Solvent A contained hexane:isopropanol (3:4) and solvent B contained hexane:isopropanol:aqueous 1 mM ammonium acetate (3:4:0.7). The starting HPLC solvent consisted of 55% solvent A and 45% solvent B. From 0 minutes to 20 minutes the % of solvent B was increased incrementally to 60%. After the 20 minute time mark, solvent B was increased to 100% until the end of the chromatography. A photodiode array detector was used to monitor lipid species throughout the procedure at 200 nm. The desired xylitol lipid peak was recovered, dried under nitrogen gas and subjected to Bligh-Dyer extraction.
Thin Layer Chromatography (TLC):

TLC was used to separate lipids according to their head group structure on Merck Silica 60 glass plates. The silica plate was scored vertically according to sample number, and aliquots of 15 µg of lipid were spotted onto each lane. A touchstone solvent system was used to separate lipid classes containing chloroform:2-propanol:methanol:0.2 M aqueous potassium chloride:triethylamine (90:75:30:18:55). After lipids were spotted on the plate, it was placed in solvent for 90 minutes and then the plate was air-dried. After drying the plate, it was sprayed with 0.1% ANSA-water and its contents were visualized under UV light. Lipid spots were cut out from the plate and quantified by phosphorus analysis.
Lipid Phosphorus Analysis:

Phosphorus analysis was used to quantify lipid amounts [G. Rouser, A. N. Siakotos, and S. Fleischer, "Quantitative analysis of phospholipids by thin-layer chromatography and phosphorus analysis of spots.," *Lipids*, vol. 1, no. 1, pp. 85-6, January 1966.]. A standard curve of $KH_2PO_4$ was prepared in glass vials with 0, 5, 10, 20, 40, and 80 nmol in a 320 µL aqueous volume. An aliquot of dried lipid or lipid spots cut out from a silica plate was added to glass vials. 90 µL of 70% Perchloric Acid was added to each vial for both the standards and the lipid samples. Marbles were placed on top of each tube and the lipid-containing vials were then heated at 180° C. for 30 minutes. After cooling, 500 µL of deionized water (dH2O) was added to each standard vial and 820 µL of $dH_2O$ was added to each lipid vial. 100 µL of 2.5% Ammonium Molybdate was added to all vials followed by vortexing to mix contents. Next, 100 μL of 10% Ascorbic Acid was added to all vials followed by vortexing. All samples were heated in a 50° C. water bath for 15 minutes followed by optical absorbance measurement at 820 nm using a spectrophotometer.

Mass Spectrometry:

Characterization of phosphatidylxylitol (PX) lipids was carried out on Applied Biosystems (AB) Sciex QTrap 4000 and Synapt G2-S mass spectrometers. Purified lipids were infused into the AB Sciex QTrap 4000 in a methanol:water (2:1) solution containing 1 mM ammonium acetate. The QTrap conditions for negative ion mode were: declustering potential −90 V, ion spray voltage-4000 V, entrance potential −10 V. The parameters for positive ion mode were identical to that for the negative ions, except the ion spray voltage, which was 4500 V. Collision energy for CID of PX lipids varied with each compound ranging from 10 V to 70 V for positive ions and −10 V to −40 V for negative ions.

Results:

Synthesis and Purification of Xylitol-Headgroup Lipids:

Xylitol is a five-carbon linear sugar alcohol that is widely used as a bulk sweetener and is never fully broken down in the body [K. Amo, H. Arai, T. Uebanso, M. Fukaya, M. Koganei, H. Sasaki, H. Yamamoto, Y. Taketani, and E. Takeda, "Effects of xylitol on metabolic parameters and visceral fat accumulation.," *J. Clin. Biochem. Nutr.*, vol. 49, no. 1, pp. 1-7, July 2011.]. Because xylitol is a natural product that has been safely used, is not extensively metabolized and has a primary alcohol, it was an attractive substrate to use as the head group of a POPG analog. A transphosphatidylation reaction was used to synthesize new PX lipids. In order to vary the hydrophobic chains of xylitol lipids, different lipid molecular species of the choline class, (purchased from Avanti) were used. Because phospholipids are amphipathic, the transphosphatidylation reaction uses a two-phase system. An ether phase and a water phase is used knowing that the lipophilic portion of the phospholipid will be in the ether phase and the hydrophilic head portion will be in the water phase.

A 40%-50% w/v concentration (2.6 M-3.3 M) of xylitol was used and the reaction was vortexed overnight at varying temperatures depending on phase transitions of lipids. Vortexing the ether-water mixture forms an emulsion that aids in the transphophatidylation reaction.

Nine novel compounds were synthesized using the methods described previously. These compounds have a xylitol polar headgroup and variable hydrophobic regions consisting of two aliphatic chains ranging from 14 to 18 carbons in length with differing degrees of unsaturation. An additional variation in structure of these novel lipids is the type of linkage between the aliphatic chains and the glycerol backbone of the phospholipid. The linkages are either ester type (O-acyl) or ether type (O-alkyl). The reaction conditions used for synthesis of each xylitol compound are summarized in Table 2. The table highlights the hydrophobic chains on the PC starting material denoted as the number of carbons: number of double bonds for the sn1 fatty acid/number of carbons:number of double bonds for the sn2 fatty acid. The hydrophobic chains of glycerophospholipids found in lung surfactant are attached to the glycerol backbone via an ester linkage. Two of the P lipids synthesized contain ether-linked hydrophobic chains to the glycerol backbone and are denoted in Table 2 with an "e" following the number of double bonds reported. Ether-linked lipids were synthesized so that the compound would be resistant to cleavage by A1, A2 and B family phospholipases.

TABLE 2

Summary of conditions used in transphosphatidylation reactions

| Starting Material | Alcohol | Molarity | Time (h) | Temp. (° C.) | Recovery (%) | Product [M − H]− m/z (Da) |
|---|---|---|---|---|---|---|
| 14:0/14:0 PC | Xylitol | 2.6-3.3 | 18 | 22-37 | 25.4-40 | 725.5 |
| 14:0e/14:0e PC | Xylitol | 2.6-3.3 | 20 | 37 | 22.5-48 | 697.6 |
| 16:0/16:0 PC | Xylitol | 2.6-3.3 | 24 | 42.5 | 64-80.7 | 781.5 |
| 16:0/18:1 PC | Xylitol | 2.6-3.3 | 18 | 22-37 | 30.5-41.4 | 807.5 |
| 16:1/16:1 PC | Xylitol | 2.6-3.3 | 18 | 22-37 | 32.8-47 | 777.5 |
| 18:0/18:0 PC | Xylitol | 2.6-3.3 | 24 | 42.5 | 40-59 | 837.6 |
| 18:1/18:1 PC | Xylitol | 2.6-3.3 | 18 | 22-37 | 36-54 | 833.6 |
| 18:1e/18:1e PC | Xylitol | 2.6-3.3 | 20 | 37 | 31-72 | 805.6 |
| 18:2/18:2 PC | Xylitol | 2.6-3.3 | 18 | 22-37 | 49.3-78.8 | 829.5 |

POPG has a short half-life in the mouse lung of about 45 minutes. Although POPG has both antiviral and anti-inflammatory properties, prophylactic and therapeutic studies in animal models are of limited value because of the fast turnover rate. The ether-linked analogs help address this problem because the resistance to phospholipases has the potential to extend the lipids' half-life, and thus can have greater efficacy/potency than that of POPG.

Thin layer chromatography (TLC) was used to monitor the progress of transphosphatidylation reactions in a basic solution that separates lipid class by headgroup. The distinction between the unreacted starting material, PC, the hydrolysis product, PA and the desired transphosphatidylation product, PX can be visualized with ANSA and UV light.

When all of the PC starting material was converted to either the xylitol transphosphatidylation product or the PA hydrolysis product, lipids were extracted using the Bligh-Dyer method and the desired PX lipids were purified from the reaction mix using normal phase high performance liquid chromatography (HPLC). PX lipids elute between 9 and 13 minutes and were collected, dried under a stream of nitrogen and extracted by the Bligh-Dyer method.

Purified lipids were resuspended in a known volume of chloroform:methanol (9:1) and quantified by phosphorus analysis. Purity of the entire collection of xylitol lipids was confirmed by TLC using UV visualization. The thin layer chromatogram displays purified PX lipids with no evidence of contamination by PC starting material or the hydrolysis product, PA. Individual structures of each xylitol lipid are shown in FIG. 1.

Each PX lipid has been labeled with an abbreviation according to its structural components, and these designations are utilized herein and are explained in Table 3. It should be noted that the two xylitol compounds whose hydrophobic chains are attached to the glycerol backbone through an ether linkage are shown in bold in Table 3 (14:0 Diether-phosphatidylxylitol and 18:1 Diether-phosphatidylxylitol).

TABLE 3

Summary of PX lipid library and abbreviation reference

| Xylitol Compound | Abbreviation | sn1 | sn2 |
|---|---|---|---|
| Dimyristoyl-phosphatidylxylitol | DMPX | Acyl-14:0 | Acyl-14:0 |
| 14:0 Diether-phosphatidylxylitol | 14:0 DEPX | Alkyl-14:0 | Alkyl-14:0 |
| Dipalmitoyl-phosphatidylxylitol | DPPX | Acyl-16:0 | Acyl-16:0 |
| Palmitoyl-oleoyl-phosphatidylxylitol | POPX | Acyl-16:0 | Acyl-18:1 |

TABLE 3-continued

Summary of PX lipid library and abbreviation reference

| Xylitol Compound | Abbreviation | sn1 | sn2 |
| --- | --- | --- | --- |
| Dipalmitoleoyl-phosphatidylxylitol | 16:1 DPPX | Acyl-16:1 | Acyl-16:1 |
| Distearoyl-phosphatidylxylitol | DSPX | Acyl-18:0 | Acyl-18:0 |
| Dioleoyl-phosphatidylxylitol | DOPX | Acyl-18:1 | Acyl-18:1 |
| 18:1 Diether-phosphatidylxylitol | 18:1 DEPX | Alkyl-18:1 | Alkyl-18:1 |
| Dilinoleoyl-phosphatidylxylitol | 18:2 DLPX | Acyl-18:2 | Acyl-18:2 |

Characterization of Xylitol Lipids by Mass Spectrometry:

Synthesis of the novel xylitol-headgroup analogs disclosed herein have been confirmed utilizing electrospray ionization (ESI) quadrupole tandem mass spectrometry.

The Applied Biosystems (AB) Sciex QTrap 4000 that was used to characterize PX lipids contains three quadrupoles. Quadrupoles are composed of four rods that are independently linked to radio frequency (RF) and direct current (DC) voltages. Upon ionization, PX lipids enter the Q1 cell in a continuous ion beam. This first quadrupole cell is utilized as a mass filter. Through manipulation of RF and DC voltages the resulting time dependent hyperbolic electrical field created selects for ions of a specified m/z. The second cell, Q2 is utilized as a collision cell and contains an inert gas, such as nitrogen gas (N2). Ions entering Q2 will collide with inert gas molecules causing vibrational energy between covalent bonds in the sample molecule. This interaction and vibrational energy eventually exceeds the energy of the covalent bonds keeping different substituents together, leading to bond to breakage and fragmentation of the parent ion. The Q3 cell functions as an additional mass filter to select for specific fragments generated in Q2 (F. Kero, et al., "Quadrupole mass analyzers: theoretical and practical considerations," in *Core Methodologies*, 2005, pp. 1-9). In characterizing novel PX lipids in this thesis, Q3 was used to scan a m/z range for the detection of product ions following fragmentation and ion abundance was determined by an electron multiplier detector.

Following synthesis and purification of xylitol analogs, each compound was analyzed by mass spectrometry product ion scans. The m/z ratio of each lipid was determined by infusing PX lipids in a methanol:H2O (2:1) containing 1 mM ammonium acetate solution and selecting an RF only method. The contents of the injected sample were detected without selecting for a specific mass. Once the parent lipid ion was determined, Q1 was adjusted to filter out all other m/z except the desired ion and then collisionally activated in Q2, followed by detection of the resulting product ions. Each xylitol lipid synthesized corresponded to its predicted mass, and m/z ratios of each compound for negative ions [M-H]− is shown in Table 2. Through product ion scans the fragmentation spectra for the new library of lipid compounds was determined. PX lipids are anionic and form abundant negative ions [M-H]− in negative ion mode within the mass spectrometer. Neutral loss of the xylitol head (−134) is observed in the spectra of each PX lipid along with an ion at m/z 213 pertaining to the xylitol head group with the phosphate attached. These two transitions unique to PX lipids serve as multiple reaction monitoring (MRM) transitions that can be utilized to identify xylitol compounds in a complex mixture by mass spectrometry.

Nine novel xylitol-headgroug analogs of POPG were synthesized by transphosphatidylation reaction utilizing phospholipase D isolated from cabbage as the active enzyme. The reactions were carried out at temperatures ranging from 22° C. to 42.5° C. (Table 2) and reaction progress was monitored by TLC. The reactions forming DMPX, POPX, 16:1 DPPX, DOPX, and 18:2 DLPX progressed at temperatures from 22° C. to 37° C. The reactions synthesizing 14:0 DEPX and 18:1 DEPX ran at 37° C. and reactions for DPPX and DSPX ran at 42.5° C. The temperatures in which the reactions successfully ran are a reflection of the different transition temperatures of the PC starting material. The transition temperature is the point at which lipids go from a more rigid gel phase to a liquid crystalline phase. The transition temperature is lower for PC species with shorter chained fatty acids and those that have at least one double bond. Saturated PC species have a higher transition temperature and, although information was not available reflecting the phase transition temperature of the diether PC species, my results indicate the ether-linked hydrophobic chains increase the phase transition temperature of the lipid because their reactions did not proceed at room temperature when their identical ester-linked counterparts did.

Reaction conditions for xylitol lipid synthesis included a 40-50 weight percent of xylitol. The optimized condition for PX synthesis was 40% xylitol and resulted in the upper limit yields in Table 2. All xylitol lipids readily solubilized in a chloroform:methanol (9:1) solution for storage at −20° C. However, during HPL purification of the saturated PX lipids, a precipitate formed while resuspending these lipids in the starting solvent. This problem was alleviated by purifying only small amounts of saturated PX reaction mix at one time. However, in the future, purification of saturated PX lipids by TLC followed by lipid extraction from the silica might prove to be a more efficient method.

This example demonstrates that phospholipids of the xylitol lipid class are synthesized in high yields by a transphosphatidylation reaction, including the synthesis of ether-linked PX lipids. The unique fingerprint of each of these novel compounds was determined by mass spectrometry and MRM transitions were identified.

Example 2

This example shows the assessment of the innate immune function of xylitol-headgroup phospholipids in vitro as well as the in vitro assessment of xylitol lipid analogs as inhibitors of RSV infection:

Experimental Procedures:

Materials:

Lipopolysaccharide (LPS) from *Escherichia coli* serotype 0111:B4, PolyU, and poly I:C were all purchased from Sigma. CpG was purchased from InvivoGen. Macrophage-activating lipopeptide-2 (MALP-2), Pam3Cys and Flagellin were obtained from Enzo Life Sciences. The ectodomain of TLR3 protein was purchased from R&D system. The mouse TNF-α Cytoset™ ELISA kit was obtained from Biosource, Camarillo, Calif. The Human IL-8 ELISA kit was purchased from Novex. An RSV-HRP antibody was purchased from AbD Serotec. The antibody Beta-Actin was obtained from Cell Signaling Technology. HEp2 cells, BEAS2B cells, RAW264.7 cells and human RSV A2 strain (VR-1540) were obtained from the American Tissue Culture Collection (ATCC). Bovine growth serum was obtained from Hyclone, and heat inactivated at 56° C. for 30 minutes. DMEM, RPMI-1640 and BEGM were purchased from Lonza. Agarose for plaque assays was obtained from MP Biomedicals, LLC. 96-well, 48-well and 6-well plates were purchased from Corning.

RAW264.7 Macrophage Cell Tissue Culture and Treatment with Toll-Like Receptor Agonists in the Presence or Absence of Xylitol Analogs:

The mouse macrophage cell line, RAW264.7, was obtained from ATCC and maintained in DMEM, supplemented with 10% bovine growth serum and 1× penicillin streptomycin. Cells were maintained at 37° C. with 5% carbon dioxide: 95% air atmosphere within the incubator. Experiments were completed in a 96-well plate where cells were seated at a density of $1\times10^5$ cells per well, 24 prior to stimulation with TLR agonists and antagonists. Lipids were dried under a stream of nitrogen, hydrated with phosphate-buffered saline (PBS) at 37° C. for one hour, followed by water bath sonication to create liposomes. Each condition for cell stimulation and antagonism was prepared in DMEM in a separate tube and consisted of: control, TLR agonist, TLR agonist+lipid, and lipid alone. 100 μL aliquots of medium+agonists+antagonists were added to each well and incubated at 37° C. for 4 hours. Subsequently, the media were collected, diluted and an enzyme-linked immunosorbent assay (ELISA) was performed to quantify TNFα release by cells.

Bronchial Epithelial Cell (BEAS2B) Tissue Culture and Treatment with Toll-Like Receptor Agonists+/−Xylitol Analogs:

Human bronchial epithelial cells, BEAS2B, were obtained from ATCC and maintained in bronchial epithelial cell growth medium (BEGM), supplemented with the Bulle-Kit from Lonza in accordance with protocol (M. H. Hudy, S. et al., "Cigarette smoke modulates rhinovirus-induced airway epithelial cell chemokine production.," *Eur. Respir. J.*, vol. 35, no. 6, pp. 1256-63, June 2010). Cells were cultured at 37 C with 5% carbon dioxide:95% air atmosphere maintained within the incubator. Experiments were conducted in 48-well plates and cells were seated at a density of $5\times10^4$ per well. After 24 hours, the BEGM medium was replaced with RPMI-1640 medium and incubated for an additional 24 hours. Liposomes were prepared as described above. Each condition for cell stimulation and antagonism was prepared in RPMI medium in a separate tube and consisted of: control (medium alone), TLR agonist, TLR agonist+lipid, and lipid alone. The cells were incubated in 250 mL medium either with or without agonists and antagonists at 37° C. for 48 hours. Subsequently, media were collected, diluted and an enzyme-linked immunosorbent assay (ELISA) was performed to quantify IL-8 release by cells.

Binding of TLR 3 Ectodomain to Solid Phase Phospholipid:

Lipids were dried under a stream of nitrogen and resuspended i 100% ethanol, and 0.625 nmol was added in a 40 μL volume to each well of a half-area, 96-well plate. The solvent was evaporated under warm air for 90 minutes. 120 μL of blocking solution (150 mM NaCl, 20 mM sodium acetate pH 5.5 containing 3% BSA w/v) was added to each well and incubated for 1 hour at room temperature. Wells were then washed with (150 mM NaCl, 20 mM sodium acetate pH 5.5) followed by the addition of 40 μL of 6 μg/mL TLR 3 ectodomain in blocking solution to each well and the plate was incubated at 37° C. for 1 hour. The wells were washed 3 times and 40 μL of human TLR 3 primary antibody, diluted 1:500, was added and incubated overnight at 4° C. After washing out the primary antibody with (150 mM NaCl, 20 mM Tris pH 7.4), a secondary (rabbit anti-goat) antibody conjugated to horseradish peroxidase (HRP), diluted 1:1000, was added in 40 μL aliquots to each well and incubated at 37° C. for 1 hour. After washing, the peroxidase activity was detected with the substrate o-phenylenediamine and the absorbance read at 490 nm to detect degree of binding.

Quantitative RSV Plaque Assays and Inhibition by Phospholipids in HEp2 Cells:

Viral stocks were propagated in HEp2 cell monolayers using DMEM/Ham's F12 Medium (GIBCO), plus 5% bovine growth serum (Hyclone) with 1× penicillin streptomycin, and virus was purified using methods previously described [M. Numata, H. W. Chu, A. Dakhama, and D. R. Voelker, "Pulmonary surfactant phosphatidylglycerol inhibits respiratory syncytial virus-induced inflammation and infection.," *Proc. Natl. Acad. Sci. U.S.A.*, vol. 107, no. 1, pp. 320-5, 2010.]. Viral titers and growth were measured by plaque assays [J. L. McKimm-Breschkin, "A simplified plaque assay for respiratory syncytial virus-direct visualization of plaques without immunostaining," 2004.]. The antiviral activity of xylitol-headgroup lipids was determined by in vitro RSV infection in the presence or absence of lipid and infectious particles were quantified by viral plaque assay. HEp2 cells were plated at a density of $1.8\times10^6$ per well in a 6 well plate 24 hours prior to infection in order to create a uniform monolayer. Cell monolayers were infected for 2 hours at 37° C. with serial dilutions of RSV alone and RSV in combination with 50 μg/mL of phospholipid. Following the 2-hour period of infection, the inoculum was removed and 3 mL of medium containing 0.3% agarose was added, allowed to solidify and placed in a 37° C. incubator for 6 days. On day 6 the cells were fixed overnight with formalin and then stained with a neutral red stain and viral plaques were quantified visually.

Binding of RSV to Solid Phase Phospholipid:

Lipids were dried under a stream of nitrogen and resuspended in 100% ethanol, and 0.625 nmol was added in a 40 μL volume to each well of a half-area, 96-well plate. The solvent was evaporated under warm air for 90 minutes. 120 μL of blocking solution (150 mM NaCl, 20 mM Tris pH 7, 5 mM $CaCl_2$) containing 3% BSA w/v) was added to each well and incubated for 1 hour at room temperature. Wells were washed 3 times with (150 mM NaCl, 20 mM Tris pH 7, 5 mM $CaCl_2$)) followed by the addition of 40 μL of serial dilutions of RSV ($2.5\times10^7$, $1.25\times10^7$, $0.625\times10^7$, $0.3125\times10^7$, $0.15625\times10^7$ pfu/mL) in blocking solution to each well and the plate was incubated at 37° C. for 1 hour. The wells were washed 3 times and 40 μL of α-RSV:HRP antibody diluted 1:500 was added and incubated at 37° C. for 1 hour. After washing out the primary antibody, the peroxidase activity was detected with the substrate o-phenylenediamine and the absorbance read at 490 nm to detect degree of binding.

Western Blot Analysis of Phospholipid Interference with RSV Binding to HEp2 Cells:

HEp2 cells were plated in a 48-well plate at a density of $1\times10^5$ per well, 48-hours prior to performing binding studies. A multiplicity of infection (MOI) of 2.5 was used and conditions of a control with no RSV, RSV alone and RSV plus 50 μg/mL of selected lipids were added to cells for a 2-hour incubation at 18° C. This lower temperature was used so that RSV would adsorb to the cell surface with minimal endocytosis. After binding, cells were washed 4 times with cold PBS to remove any unattached virus. 80 μL of SDS-PAGE loading buffer (sample buffer+protease inhibitor+DTT) was added to each well and the plate was set in boiling water for 1 minute to lyse cells and solubilize proteins. Cell lysates were recovered by scraping and pipteing and stored at −20° C. Subsequently, thawed lysates were boiled for 5 min, and proteins were resolved on 8-16% gradient Tris- SDS-polyacrylamide gels. The separated proteins were transferred to nitrocellulose membranes and subsequently incubated in blocking buffer containing 20 mM Tris-HCl buffer (pH 7.6), 137 mM NaCl, 0.1% Tween 20, and 5% nonfat milk for 1 hour. After blocking, primary RSV antibody conjugated to HRP was diluted 1:500 in blocking solution, added to the membrane and incubated overnight at 4° C. The membranes were washed with TBS containing 0.1% Tween for 30 min, replacing the buffer every 10 min. The immunoreactive protein was detected using coumaric acid and luminol reagents and exposed to film. Developed films were scanned and Image J software was used for protein quantification. Beta-Actin was used a control for amount of protein loaded.

Assessing TLR Antagonism by Xylitol-Headgroup Phospholipids:

Toll-like receptors (TLRs) are the major microbial sensing detectors in the human body. They regulate acute inflammatory responses upon detection of molecular constituents of foreign microbes, and engage innate immune function and processes that facilitate containment and destruction of the pathogens. Although these receptors have been studied in great detail, there is much about them that is still unknown, including methods to either harness or block TLR activation for the ultimate purpose of enhancing adaptive immunity, or suppressing deleterious inflammatory processes. TLRs are integral membrane proteins that reside on the plasma membrane and endosomal membranes.

Upon detection of pathogen-derived molecules in the exoplasmic milieu, the TLRs transduce signals across the cell membranes and engage signaling cascades. Each TLR recognizes families of molecules that are conserved among microorganisms, but not found in the host. One method to identify new agonists/antagonists of TLRs is to stimulate their activation with a known agonist in the presence of a new compound, and determine the amount of proinflammatory cytokine output into the culture medium. This example describes the activity of novel phosphatidylxylitol (PX) lipids as antagonists of TLR-dependent inflammatory responses by cultured cells; and antagonists of RSV infection. In this work, considerable emphasis is also placed upon the hydrophobic moieties of PX lipids and the effects such structural variations have upon the antagonistic actions of the molecules.

Double Bonds and Saturated Aliphatic Chain Length of PX Lipids are Important Determinants of Antagonism of TLR 4:

TLR 4 complexed with CD14 and MD2 initiate a signaling cascade in response to LPS. LPS historically is known for inducing sepsis and selective suppression of TLR 4 has the potential to reduce the excess inflammation that occurs in sepsis. TLR 4 is also activated during RSV infection that is known to play a role in uncontrolled inflammatory responses that lead to acute lung injury (ALI) (L. M. Haynes, et al., "Involvement of toll-like receptor 4 in innate immunity to respiratory syncytial virus.," *J. Virol.*, vol. 75, no. 22, pp. 10730-7, November 2001; Y. Imai, et al., "Identification of oxidative stress and Toll-like receptor 4 signaling as a key pathway of acute lung injury.," *Cell*, vol. 133, no. 2, pp. 235-49, April 2008; K. A. Shirey, et al., "The TLR4 antagonist Eritoran protects mice from lethal influenza infection," *Nature*, vol. 497, no. 7450, pp. 498-502, May 2013).

Work by the inventor has demonstrated POPG inhibits TLR signaling by preventing ligand binding to CD14 and MD2 (K. Kuronuma, et al., "Anionic Pulmonary Surfactant Phospholipids Inhibit Inflammatory Responses from Alveolar Macrophages and U937 Cells by Binding the Lipopolysaccharide-interacting Proteins CD14 and MD-2," *J. Biol. Chem.*, vol. 284, no. 38, pp. 25488-25500, September 2009). The additional experiments disclosed herein, tested the initial activity of multiple POPG analogs. Among them, a novel phospholipid harboring a xylitol head group demonstrated a strong ability to antagonize TLR 4 activation. However, it was unknown how the combination of a xylitol head group along with varying hydrophobic chains affects this activity and mechanism of suppression. Varying the hydrophobic chains provides an approach for optimization of a PX lipid for maximum efficacy and uncovers important structure/function relationships. To test antagonist activity of PX lipids for preventing the activation of TLR 4, LPS was added to RAW264.7 cells at 10 ng/mL in the absence or presence of 50 μg/mL of lipid and incubated for 4 hours. After incubation, media were collected and secretion of the proinflammatory cytokine, TNFα, was quantified by ELISA as a downstream consequence of TLR 4 activation. Eight xylitol lipid analogs suppressed the activation of TLR 4 in the presence of LPS stimulus. DPPX, which contains hydrophobic chains with 16 carbons in length and is saturated was ineffective as an antagonist. Although inhibition of TLR 4 by DSPX was statistically different from LPS alone, its antagonism was marginal. DSPX is also a saturated lipid and the hydrophobic chains are 18 carbons in length. In contrast, the saturated lipid, DMPX, with chains 14 carbons in length demonstrated strong antagonistic activity. Notably, both ether-linked lipids, 14:0 DEPX and 18:1 DEPX, were effective antagonists. In these studies none of the lipids alone elicited significant amounts of proinflammatory cytokine release.

Figure 3:
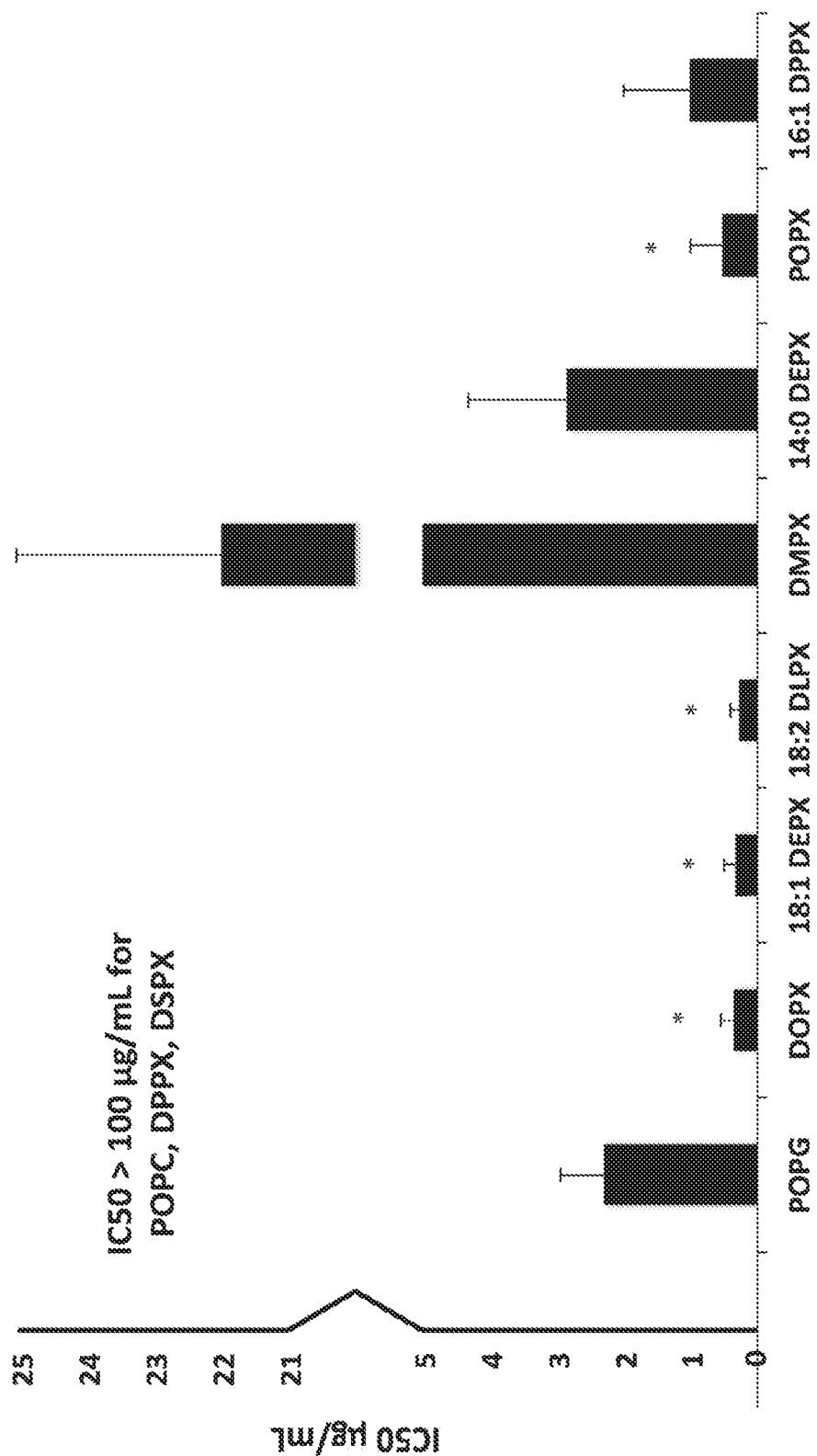
FIG. 3 shows four xylitol phospholipids are more effective at antagonizing TLR4 activation than POPG. Cultures of RAW 264.7 cells were challenged with 10 ng/ml LPS and 0-50 µg/ml of lipids, and the IC50 values for inhibition of TNF-α production were calculated from dose response curves. * indicate $p<0.05$.
Figures 4A, 4B:
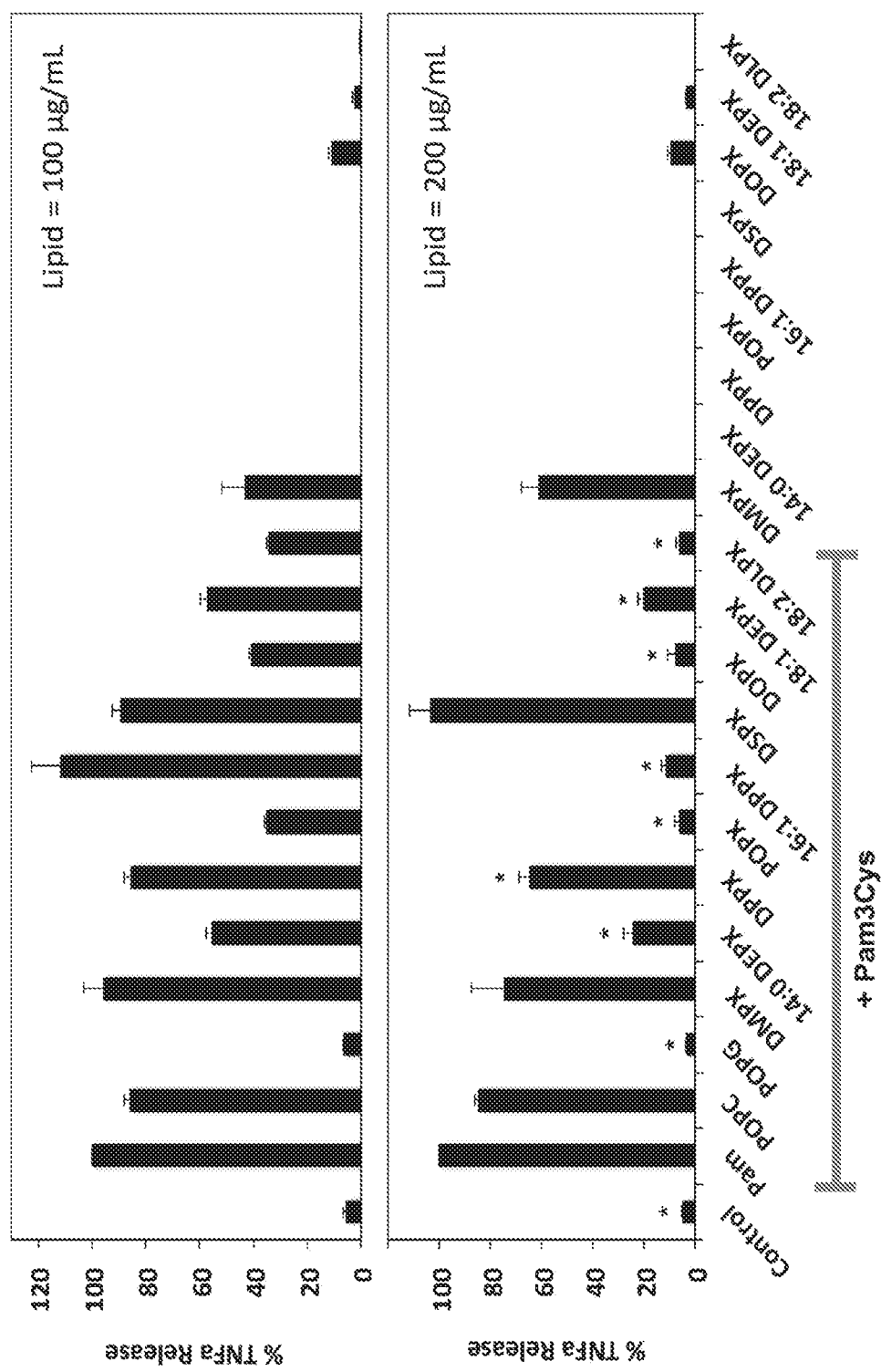
FIGS. 4A and 4B show multiple xylitol phospholipids inhibit TLR 2/1 activation by Pam3Cys. Cultures of RAW264.7 cells were challenged with 1 µg/ml of the TLR 2 agonist Pam3Cys (+Pam3Cys) in the absence or presence of either 100, or 200 µg/ml phospholipids as shown in the panels, and TNF-α (also referred to as TNF-α) secretion into the medium was quantified after 4 hrs by ELISA. * indicate $p<0.001$ when compared with Pam3Cys alone.

For quantitative comparisons between POPG analogs and POPG, concentration-dependent inhibition studies were performed and IC50 values were determined. RAW264.7 cells were stimulated with 10 ng/mL of LPS in combination with concentrations of lipid from 100 μg/mL to 0.008 μg/mL. Cells were stimulated for 4 hours followed by collection of media and quantification of TNFα released into the medium. The IC50 values for analogs compared with POPG are shown in FIG. 3. As shown in FIG. 3, the inhibitory concentration reducing TNF-α production by 50% (IC50), is ~2 μg/ml for POPG, but is ~0.3-0.5 μg/ml for DOPX, 18:1 DEPX, 18:2 DLPX and POPX.

Figure 2:
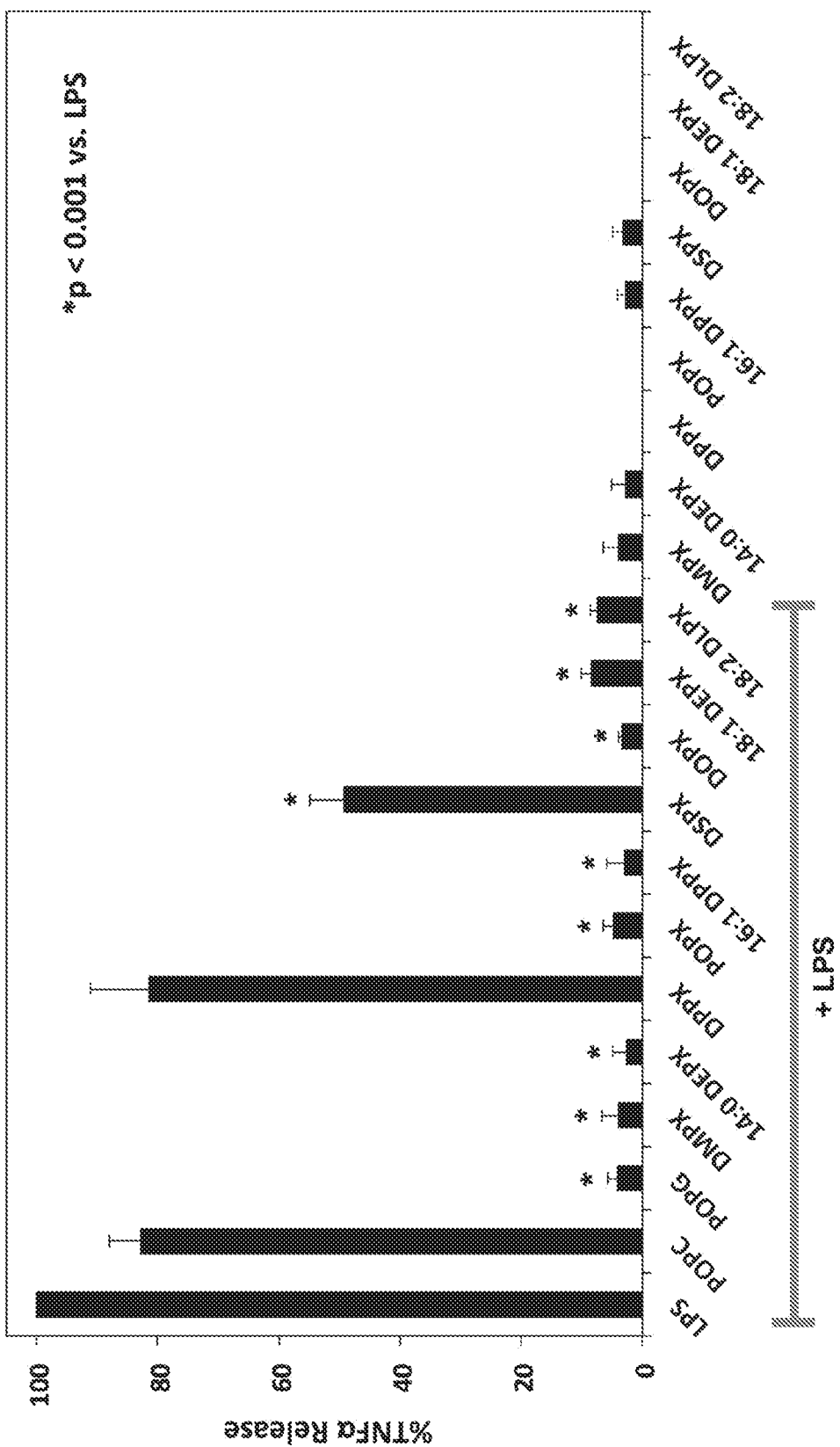
FIG. 2 shows that DOPX and 18:1 DEPX inhibit LPS-induced release of TNF-α. Cultures of RAW 264.7 cells were challenged with 10 ng/ml of LPS, and the secretion of TNF-α into the culture medium was quantified after 4 hrs, by ELISA. All of the xylitol lipids at 50 µg/ml, except DPPX and DSPX, are nearly as potent as POPG. * indicate $p<0.001$.

The IC50 values determined for POPG, DOPX, 18:1 DEPX, 18:2 DLPX, DMPX, 14:0 DEPX, POPX and 16:1 DPPX were 3.33 μg/mL, 0.36 μg/mL, 0.33 μg/mL, 0.28 μg/mL, 24 μg/mL, 2.85 μg/mL 0.52 μg/mL and 1 μg/mL respectively. IC50 values could not be determined between 0.008 μg/mL and 100 μg/mL for POPC, DPPX and DSPX. The results indicate that xylitol lipid analogs antagonize activation of TLR 4 and that structural alteration of their hydrophobic chains significantly influence activation. A summary of antagonist activity of xylitol-headgroup lipids is shown in FIG. 2. As shown in FIG. 2, LPS induces the secretion of the inflammatory mediator TNF-α from RAW264.7 cells. The control phospholipid, POPC, does not significantly alter the activation of TLR4, whereas the bioactive phospholipid POPG inhibits activation of TLR4. With the exception of DPPX and DSPX, all of the other xylitol phospholipids show inhibitory activity comparable to POPG. Through analysis of PX analogs of POPG, seven new, highly effective TLR 4 antagonists were discovered, including four analogs that are more potent than POPG.

Select Xylitol-Headgroup Analogs Antagonize the Activation of TLR 3 in the Presence of Poly I:C:

TLR 3 is an intracellular receptor found on endosomes within cells. Signaling through TLR 3 is activated when dsRNA of viral origin is recognized and binds to the exoplasmic domain of the receptor (L. Alexopoulou, et al., "Recognition of double-stranded RNA and activation of NF-kappaB by Toll-like receptor 3.," *Nature*, vol. 413, no. 6857, pp. 732-8, October 2001; M. Tatematsu, et al., "Beyond dsRNA: Toll-like receptor 3 signalling in RNA-induced immune responses.," *Biochem. J.*, vol. 458, no. 2, pp. 195-201, March 2014). A synthetic analog of dsRNA, polyriboinosinic:polyribocytidylic acid (poly I:C) is routinely used to study TLR 3 activation (W. A. et al., "Viral infection and host defense.," *Science*, vol. 186, no. 4170, pp. 1172-8, December 1974). TLR 3 has been demonstrated as an important sensor of double stranded RNA viruses and replication intermediates from single stranded RNA viruses (T. Kawai and S. Akira, "Toll-like receptor and RIG-I-like receptor signaling.," *Ann. N. Y. Acad. Sci.*, vol. 1143, pp. 1-20, November 2008). Whether TLR 3 is protective or detrimental during viral infection in vivo, appears to be dependent on the virus (Y. Dou, et al., "Respiratory syncytial virus infection induces higher Toll-like receptor-3 expression and TNF-α production than human metapneumovirus infection.," *PLoS One*, vol. 8, no. 9, p. e73488, 2013; J. M. Thompson and A. Iwasaki, "Toll-like receptors regulation of viral infection and disease," 2007).

Figure 5:
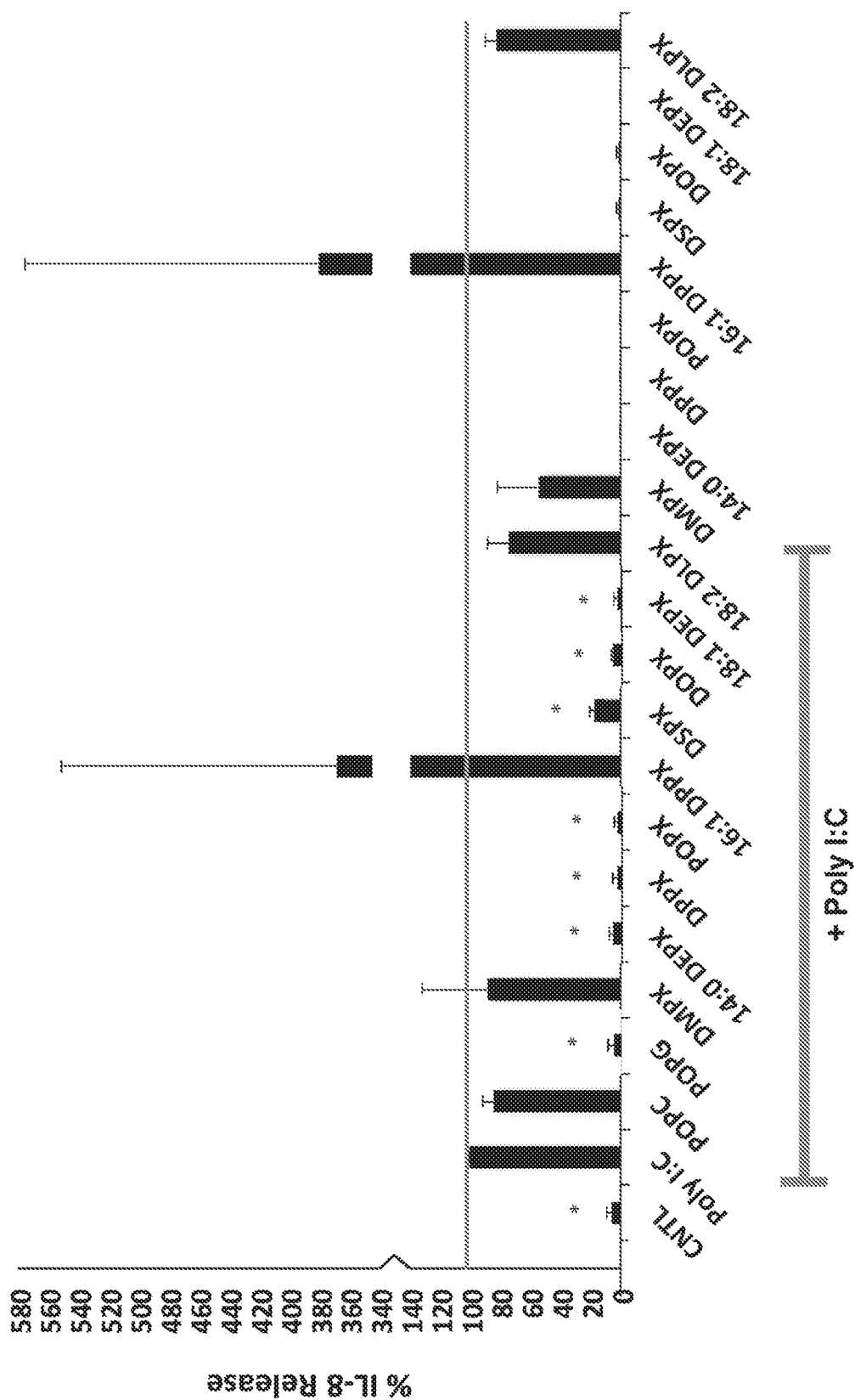
FIG. 5 shows multiple xylitol phospholipids inhibit poly I:C activation of TLR3. Cultures of BEAS2B cells were sham treated (CNTL) or challenged with 10 µg/ml of the TLR3 agonist poly I:C in either the absence, or presence of 200 µg/ml of phospholipid (POPC, POPG, and xylitol phospholipids) as indicated in the FIG. 5. After 48 hrs the medium was harvested and secreted IL-8 was quantified by ELISA. * indicates $p<0.001$.

Phosphatidylxylitol (PX) analogs demonstrated bioactivity at the surface of cells by suppressing TLR 4 activation in the presence of stimulus. The ability of PX lipids to enter the endosomal compartment and modulate immune signaling was next assessed. The human bronchial epithelial cell line, BEAS2B, expresses TLR 3 in its endosomal compartments and is susceptible to infection by respiratory syncytial virus, making this cell line ideal cell line for this study. BEAS2B cells were stimulated with the TLR 3 agonist, poly I:C, in the presence or absence of phospholipid for 48 hours. After incubation, media was collected and IL-8 was quantified as a consequence of TLR 3 activation, and results are summarized in FIG. 5. FIG. 5 demonstrates that the TLR3 agonist poly I:C induces release of the proinflammatory cytokine IL8 from BEAS2B cells, and this is unaffected by 200 μg/ml of control lipid, POPC, but markedly inhibited by 200 μg/ml POPG. Results from these experiments indicate that xylitol analogs were able to gain entry into BEAS2B cells and inhibit TLR 3 signaling. Six xylitol analogs, applied at 200 μg/ml, 14:0 DEPX, DPPX, POPX, DSPX, DOPX, and 18:1 DEPX, suppressed/inhibited activation of TLR3 in the presence of poly I:C. almost to the same extent as the bioactive lipid POPG. Interestingly, the two compounds that were ineffective antagonists for TLR 4, DPPX and DSPX, did inhibit activation of TLR 3. DMPX and 18:2 DLPX were ineffective antagonists against TLR 3 activation and also elicited an inflammatory response from BEAS2B cells in the absence of poly I:C. The compound 16:1 DPPX stimulated a robust release of IL-8 from BEAS2B cells both in the presence and absence of poly I:C. Thus, DMPX, 16:1 DPPX and 18:2 DLPX act as TLR3 agonists Xylitol Analogs Bind to TLR 3 Ectodomain:

PX analogs demonstrated differences in their ability to antagonize the activation of TLR 3. Solid phase lipid binding to fluid phase TLR 3 ectodomain was examined as a potential explanation for the differences in activity. Lipids were dried under a stream of nitrogen and resuspended in 100% ethanol. 0.625 nmol of lipid was plated per well in a 96-well plate and dried for 90 minutes. BSA was used to block non-specific binding and then TLR 3 protein was added to each well at 6 μg/mL and incubated at 37° C. for one hour. After washing out unbound protein, primary antibody was added for detection of TLR 3 and incubated overnight at 4° C. The following day secondary antibody conjugated to HRP was added to the wells and the peroxidase reaction activated by o-phenylenediamine. The absorbance was read at 490 nm to detect binding.

POPG and all xylitol analogs except 14:0 DEPX demonstrated specific binding to TLR 3 ectodomain, significantly different from the nonspecific binding to the control lipid, POPC. The two analogs that bound TLR 3 to a level most similar to POPG were 18:1 DEPX and 18:2 DLPX and are not statistically different from POPG. More detailed concentration-dependent binding was performed for POPG, 16:1 DPPX, 18:1 DEPX, and PC. TLR 3 binding to POPG, 16:1 DPPX and 18:1 DEPX was significantly different from POPC. There was no statistical difference among the binding curves of POPG, 16:1 DPPX and 18:1 DEPX when assessed by T Test.

Xylitol-Headgroup Analogs Suppress TLR 2/1 Signaling but not TLR 2/6 Activation:

TLR 2 is expressed on the cell surface and forms heterodimers with either TLR 1 or TLR 6. TLR 2 has the ability to sense a variety of microorganisms including bacteria, fungi, parasites and viral glycoproteins (A. Xagorari and K. Chlichlia, "Toll-like receptors and viruses: induction of innate antiviral immune responses.," *Open Microbiol. J.*, vol. 2, pp. 49-59, 2008). TLR 2 is the general detector of PAMPs, while TLRs 1 and 6 confer specificity of detection. The heterodimer TLR 2/1 detects triacylated lipopeptides while TLR 2/6 recognizes diacylated lipopeptides from Gram-positive bacteria and *mycoplasma*.

The ability of xylitol lipid analogs to suppress the activation of TLR 2 heterodimers was assessed. Pam3Cys was used to selectively stimulate TLR 2/1 signaling in RAW264.7 cells and MALP-2 was used as a TLR 2/6 selective agonist also in RAW264.7 cells. RAW264.7 cells were stimulated with Pam3Cys in the absence, or presence of PX lipids for 4 hours. Following incubation, media were collected, diluted and analyzed for TNFα release as a consequence of TLR activation. Results for analog activity against TLR 2/1 activation was assessed at two concentrations of phospholipid and are summarized in FIGS. 4A and 4B. The data in FIGS. 4A and 4B show that the TLR2/1 agonist Pam3CysK4 induces TNF-α production by RAW264.7 cells, and this is unaffected by 100 or 200 μg/ml of control lipid, POPC, but markedly inhibited by 100 or 200 μg/ml POPG. The xylitol lipids 14:0 DEPX, POPX, 16:1 DPPX DOPX, 18:1 DEPX and 18:2 DEPX applied at 200 μg/ml, inhibit TLR2/1 activation to almost the same extent as the bioactive lipid POPG.

Initially, activity of xylitol lipid analogs was assessed at 100 μg/mL and it was unclear whether there was a real antagonist effect especially when compared to POPG. Experiments were repeated with a 200 μg/mL concentration of lipid to determine the ability of PX lipids to suppress TLR 2/1 activation in the presence of Pam3Cys. 14:0 DEPX, POPX, 16:1 DPPX, DOPX, 18:1 DEPX and 18:2 DLPX strongly suppressed the activation of TLR 2/1 in the presence of agonist at the 200 μg/mL concentration. DMPX and DSPX were not effective antagonists of TLR 2/1 in the presence of Pam3Cys and DPPX was weakly effective. At lower concentrations, 14:0 DEPX, POPX, DOPX, 18:1 DEPX and 18:2 DLPX were modest antagonists of TLR 2/1 activation, but their antagonistic effects were amplified at higher concentrations. 16:1 DPPX did not appear to suppress activation of TLR 2/1 in the presence of Pam3Cys at 100 μg/mL but was highly effective at 200 μg/mL. DMPX and DSPX were ineffective at both concentrations. DPPX could have an effect on TLR 2/1 signaling at high concentrations.

After testing bioactivity of xylitol lipid analogs in the setting of TLR 2/1 activation, their ability to suppress TLR 2/6 activation was assessed. A RAW264.7 cell line was used with the TLR 2/6 agonist, MALP-2. Cells were stimulated for 4 hours with MALP-2 in the absence or presence of lipid at 100 μg/mL followed by collection of media and assessment of TNFα secretion. Two experiments were performed one with MALP-2 at 10 ng/mL and one with MALP-2 at 1 ng/mL. TNFα secretion was expressed as a percent of maximum release obtained with MALP-2 challenge in the absence of phospholipid antagonists. The two experiments then were averaged. PX lipids did not have a significant effect on TLR 2/6 signaling in the presence of MALP-2.

Figure 6:
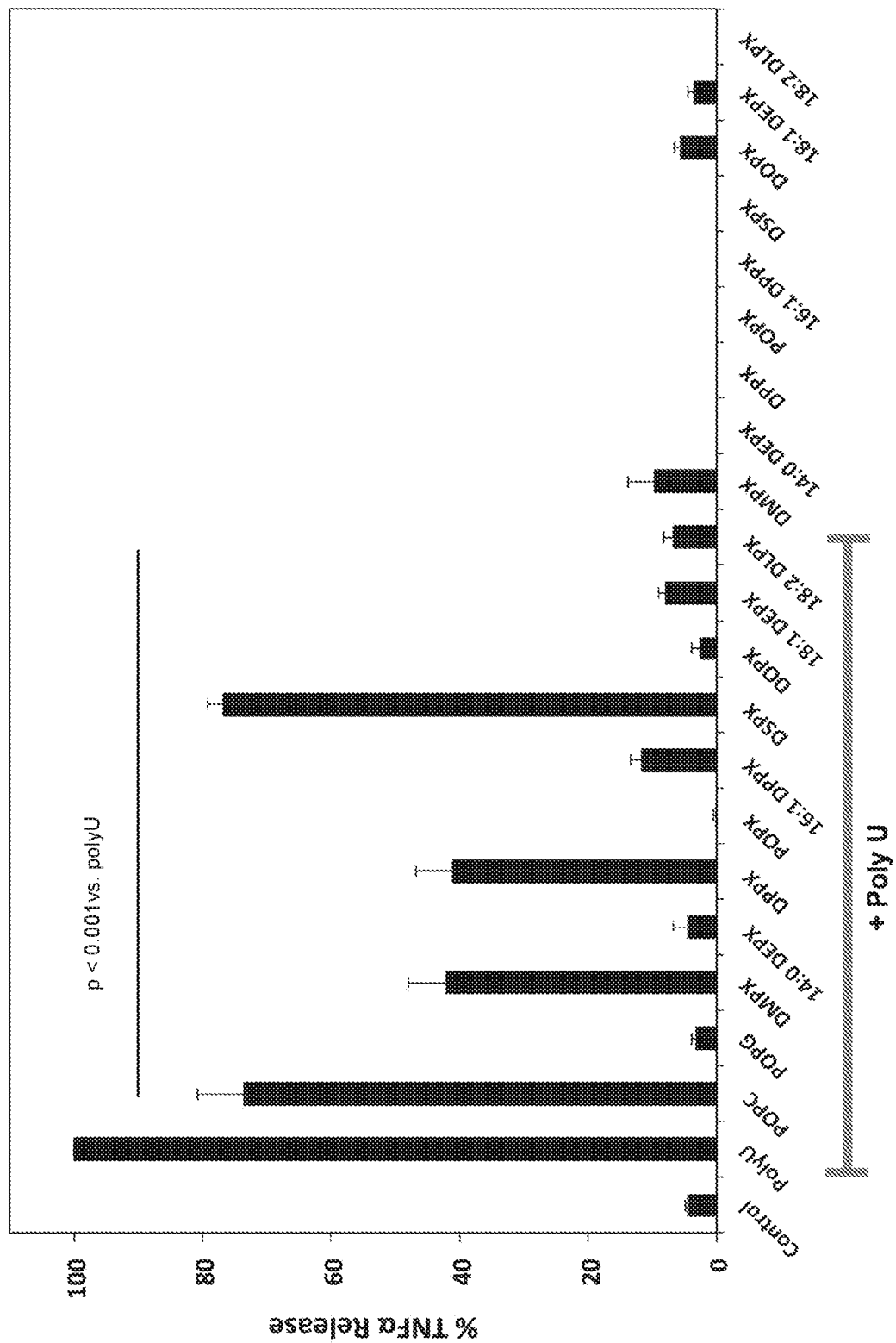
FIG. 6 shows DOPX and 18:1 DEPX inhibit poly U activation of TLR7/8. Cultures of RAW264.7 cells were challenged with 20 µg/ml of the TLR7/8 agonist poly U. After 48 hrs the medium was harvested and secreted TNF-α was quantified by ELISA. * indicates $p<0.001$.

Xylitol Lipid Analogs with Unsaturated Hydrophobic Chains or Ether-Linked Hydrophobic Chains Suppress TLR 7 Activation by the Agonist polyU:

TLR 7 is an intracellular receptor of the endosomal compartment. TLR 7 was the first innate immune receptor reported druggable with small molecules, however no breakthrough treatments have been discovered with TLR 7 agonists/antagonists yet (T. Y.-H. Wu, "Strategies for Designing Synthetic Immune Agonists," Immunology, 2016). TLR 7 detects single-stranded RNA (ssRNA) within endosomal compartments. Xylitol lipids were assessed for antagonism of TLR 7 activation in the presence of the synthetic ssRNA analog, polyuridylic acid (polyU). The macrophage cell line, RAW264.7, was used to assess antagonist activity of PX analogs in a TLR 7-dependent manner. Cells were stimulated with 20 μg/mL polyU for 4 hours in the absence or presence of 20 μg/mL phospholipid. After a 4-hour stimulation media were collected and TNFα secretion was quantified by ELISA. Results are summarized in FIG. 6. The data in FIG. 6 demonstrate that the TLR7/8 agonist poly U induces release of the proinflammatory cytokine TNF-α from RAW264.7 cells. The TNF-α release is not affected by the control lipid, POPC, but is markedly inhibited by 20 μg/ml of the bioactive lipid POPG, and 14:0 DEPX, 16:1 DPPX, DOPX, 18:1 DEPX and 18:2 DLPX. This study considered analogs that suppress TNFα release by more than 50% as effective antagonists. Saturated, ester-linked phospholipids appear to be ineffective at antagonizing TLR 7 activation where as their unsaturated ester-linked and saturated ether-linked counterparts were effective.

Figure 7:
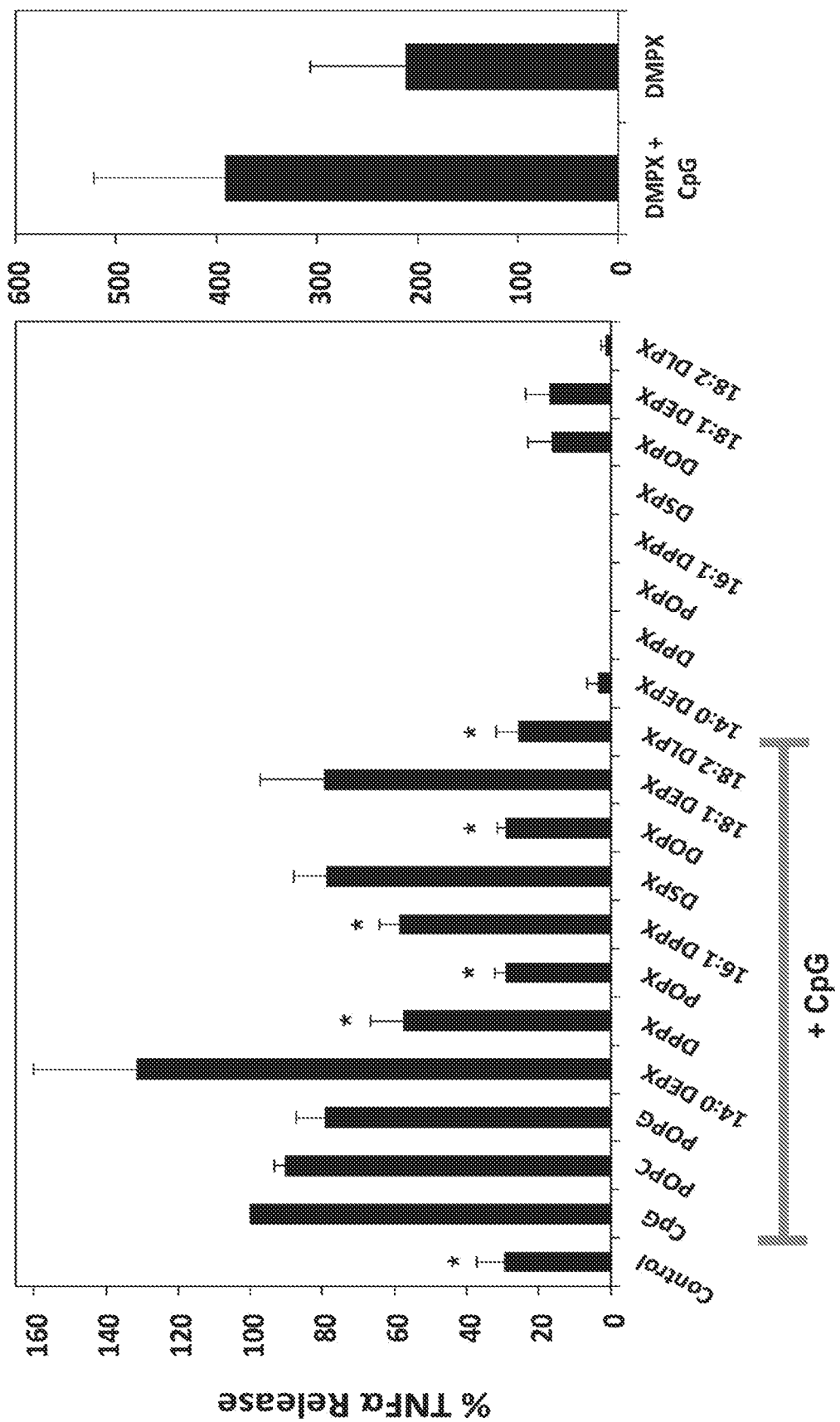
FIG. 7 shows POPX and DOPX inhibits CpG activation of TLR9. Cultures of RAW264.7 cells were challenged with 5 µg/ml of the TLR9 agonist CpG, in either the absence or presence of 200 µg/ml phospholipid (POPC, or POPG, or the indicated xylitol phospholipids). After 48 hrs the medium was harvested and secreted TNF-α was quantified by ELISA. * indicates $p<0.001$ compared with CpG treatment alone.

POPX, DOPX and 18:2 DLPX Antagonize the Activation of TLR 9 in the Presence of Stimulus:

TLR 9 is another member of the intracellular TLRs found in the endosomal compartment. It detects unmethylated CpG sequences in DNA molecules commonly found among bacteria and DNA viruses (H. Hemmi, et al., "A Toll-like receptor recognizes bacterial DNA.," Nature, vol. 408, no. 6813, pp. 740-5, December 2000; J. Lund, et al, "Toll-like receptor 9-mediated recognition of Herpes simplex virus-2 by plasmacytoid dendritic cells.," J. Exp. Med., vol. 198, no. 3, pp. 513-20, August 2003). To test antagonism activity of PX lipids against TLR 9, RAW264.7 cells were stimulated for 5.5 hours with 5 μg/mL CpG in the absence or presence of 100 μg/mL phospholipid. TNFα secreted into the media in response to stimulus was quantified and results are summarized in FIG. 7. The data in FIG. 7 demonstrate that RAW264.7 cells secrete TNF-α in response to the TLR9 agonist CpG. The action of CpG is not affected by POPC, POPG, or many of the xylitol phospholipids, such as 14:0 DEPX, DSPX and 18:1 DEPX. However, the xylitol lipids POPX and DOPX added at 100 μg/ml reduce the TNF-α secretion to control levels. DMPX acts as an agonist for TLR9 activation.

Membrane Signaling is not Disrupted Nonspecifically Following the Addition of PX Lipids TLR 5 is an extracellular member of the TLR family. It is the only TLR that detects flagellin, a ligand comprised of only protein (T. Kawai and S. Akira, "The role of pattern-recognition receptors in innate immunity: update on Toll-like receptors," Nat. Publ. Gr., vol. 11, 2010). To address whether xylitol analogs antagonize TLR activation due to disruption or destruction of all membrane signaling, PX lipids were assessed at the highest concentration used in experiments reported in this example in human bronchial epithelial cells, BEAS2B, for antagonism of flagellin activation of TLR 5. The cytokine, IL-8, was quantified as an output of TLR 5 activation.

At the highest concentration of PX lipids used throughout in vitro experiments in this thesis, none of them had an effect on TLR 5 signaling at the cell membrane. Also, 16:1 DPPX and 18:2 DLPX stimulate IL-8 secretion over that of the control in the absence of Flagellin stimulus. These experiments demonstrate that the inhibition of TLR signaling by PX lipids is specific. The results from these TLR studies in vitro indicate xylitol-headgroup lipid analogs are bioactive and that the hydrophobic portions of the molecules can be tailored to elicit specific responses among different TLRs.

Figure 8:
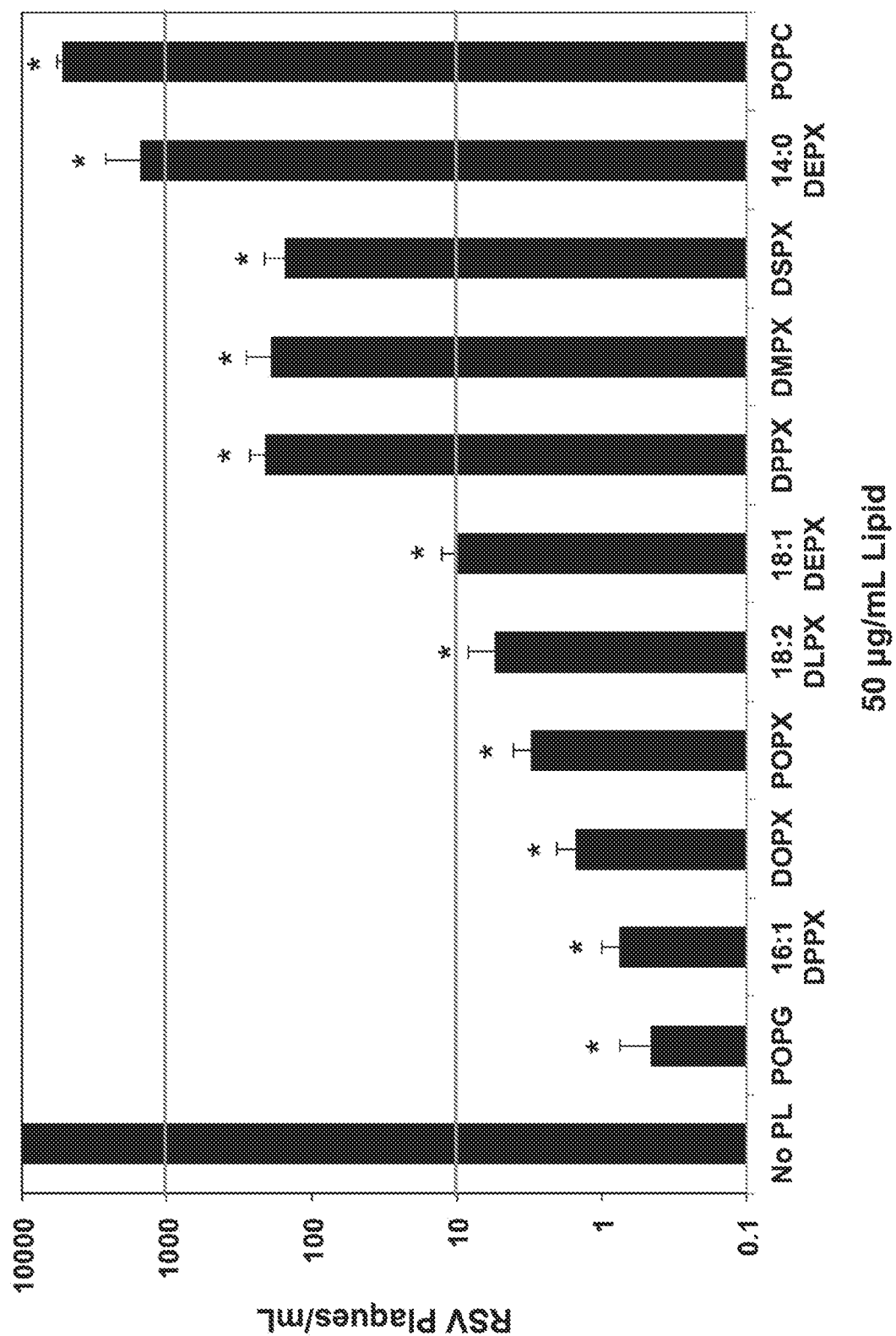
FIG. 8 shows DOPX and 18:1 DEPX inhibit infection and propagation of RSV. Cultures of HEp2 cells were infected with $10^4$ plaque forming units of RSV in either the absence (No PL) or presence of 50 µg/ml of lipids (either POPG, or POPC, or the indicated xylitol phospholipids). After 2 hrs of viral adsorption the cultures were washed three times with PBS and then overlayed with agar. After 5 days the plates were stained with neutral red and the viral plaques were quantified. Data are plotted on a log scale. * indicates $p<0.001$.

Five Xylitol Analogs Possess Highly Effective Antiviral Activity Against RSV Assessed by Quantitative Plaque Assay:

An optimized quantitative plaque assay (described for RSV by J. L. McKimm-Breschkin, "A simplified plaque assay for respiratory syncytial virus-direct visualization of plaques without immunostaining," 2004) was applied to survey the ability of PX lipids to inhibit RSV infection. The human epithelial cell line, HEp2, was seeded at a density of $1.8 \times 10^6$ per well in a 6-well plate 24 hours in advance of infection. Reaction conditions for infection took place in serum-free medium and were combined before addition to cells. A standard dilution of virus alone was prepared and 50 μg/mL phospholipid in combination with RSV was also prepared. Cells were washed with PBS to remove any serum prior to infection and then 500 μL of virus in various combinations with lipids was added to each well and incubated at 37° C. for 2 hours. Plates were rotated every 20 minutes for even distribution of viral infection. After infection, the viral inoculum was removed and medium containing 0.3% agarose was added to each well and allowed to solidify then placed back into the incubator at 37° C. for 6 days. On day 6, cells were fixed overnight then the agarose layer was removed and wells were stained with neutral red and viral plaques counted. Results from the viral plaque assay are summarized in FIG. 8. POPG is a known inhibitor of RSV infection in vitro and in vivo. The data in FIG. 8 demonstrate that 50 μg/ml POPG added to cultures challenged with $10^4$ infectious virus/ml reduces the infection by a factor of $>10^4$. Addition of 50 μg/ml 16:1 DPPX, DOPX, POPX, 18:2 DLPX, or 18:1 DEPX reduces RSV viral infection by a factor of $\sim 10^3$-$10^4$ making them highly effective at preventing RSV viral infection. In the presence of these lipids, RSV plaque formation was reduced by at least 3 log units demonstrating the ability to prevent and contain infection. Other xylitol phospholipids are much less effective. Three PX lipids, DMPX, DPPX and DSPX, moderately reduced plaque formation by at least one log unit. The lipid used as a negative control, POPC, and 14:0 DEPX was ineffective as an antiviral, defined by not reducing plaque formation by at least one log unit. Each of the highly effective antivirals have at least one double bond in their hydrophobic chains. Ester-linked saturated xylitol lipids composed the moderately effective antivirals. The sole xylitol analog that was determined ineffective was saturated and ether-linked.

Solid Phase Xylitol Lipid Analogs Bind to RSV:

A quantitative plaque assay takes a week to develop without accounting for maintenance of cells. In order to determine the mechanism of antiviral action of PX analogs and explore a faster assay that could easily be mass-produced, lipids were assessed for their ability to bind RSV. A solid phase of 0.625 nmol of lipid was dried onto a 96-well plate. Binding of fluid-phase RSV to the lipids was assessed at viral concentrations of $8 \times 10^5$ to $2.5 \times 10^7$ pfu/mL, at 37° C. for 1 hour. Viral binding was detected with a primary anti-RSV antibody conjugated to HRP. The peroxidase reaction was developed with o-phenylenediamine and absorbance measurement at 490 nm.

These experiments were conducted to determine the relationship between RSV binding to lipid and the antiviral activity of different lipids. Although the highly effective antivirals POPX and 18:1 DEPX bind to RSV with affinity comparable to that of POPG, 16:1 DPPX, DOPX, and 18:2 DLPX only bind weakly to RSV, yet were highly effective at inhibiting RSV plaque formation. The moderately effective antivirals, DPPX, DMPX and DSPX, bound strongly to RSV, and the ineffective antiviral 14:0 DEPX also bound to the RSV virus strongly. These findings demonstrate that in vitro RSV binding to lipids is not a good predictor of compound inhibition of RSV propagation.

Figure 9A:
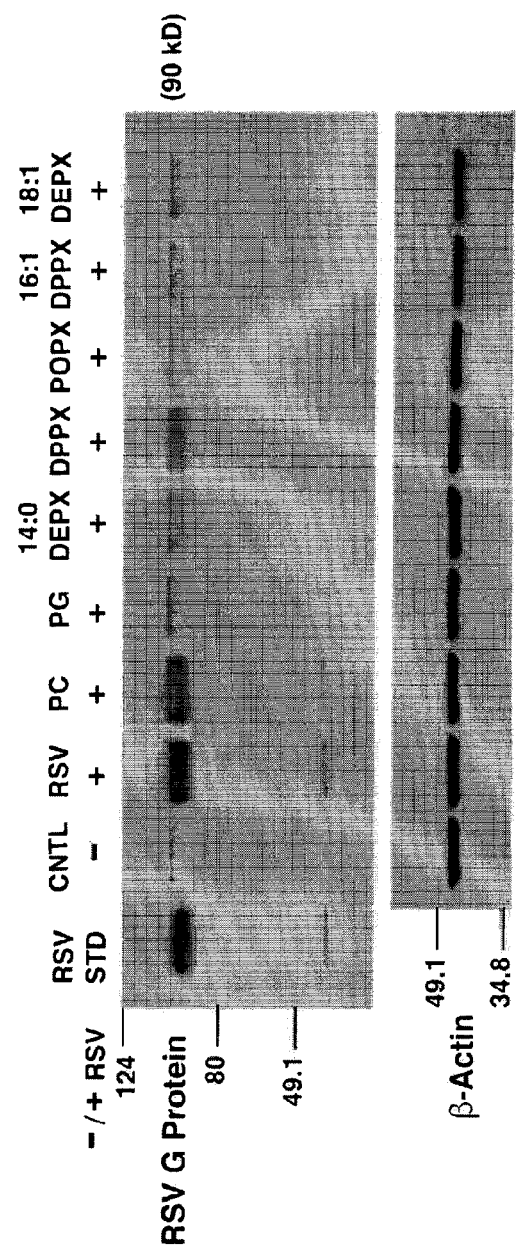

Xylitol Lipids Bind RSV and Prevent Viral Attachment to Cells:

Because binding of lipid to RSV in a biochemical assay was not a good predictor of antiviral activity, PX lipids were tested for activity preventing viral attachment to the surface of cells. HEp2 cells were plated in a 48-well plate at a density of $1 \times 10^5$ per well, 48 hours prior to viral adsorption. RSV was added to cells at multiplicity of infection (MOI) 2.5 in the absence or presence of 50 µg/mL of select xylitol lipids. The highly effective antiviral lipids POPX and 18:1 DEPX that demonstrated strong binding to RSV were selected along with 16:1 DPPX which demonstrated strong inhibition of plaque formation, yet poorly bound virus in the previous biochemical assay. The moderately effective antiviral, DPPX was selected and the ineffective antiviral, 14:0 DEPX was selected. Viral adsorption to cells was performed at 18° C. to minimize endocytosis. RSV was incubated with HEp2 cells for 2 hours, rotating the plate every 30 minutes. Cells were washed with cold PBS to remove unbound virus and cells were lysed and collected. Cell lysates were electrophoresed on an SDS-PAGE gel, and transferred to nitrocellulose membrane. The RSV G protein was detected with antibody and Beta-actin was used as a protein loading control. The results are summarized and quantified in FIGS. 9A and 9B. In more detail, monolayers of HEp2 cells were incubated with RSV at a stoichiometry of 2.5 infectious particles/cell, at 0° C., to prevent endocytosis of virions. Following a 2 hr incubation the monolayers were washed three times with cold saline to remove unbound virus, and then the cells were harvested in a denaturing solution. The cell extracts were subjected to electrophoresis under reducing and denaturing conditions and the separated proteins were transferred to nitrocellulose. Viral proteins were detected by immunoblotting with polyclonal anti-RSV antibody and enhanced chemiluminescence. The immunoreactive bands were normalized using actin immunoblots. The immunoreactive viral proteins were quantified using Image J software. The data in FIGS. 9A and 9B show that RSV binds to HEp2 cells and this binding is not inhibited by the control lipid POPC or the lipid DPPX. In contrast, POPG (PG) inhibits viral attachment by ~85%, and the xylitol phospholipids 14:0 DEPX, POPX, 16:1 DPPX AND 18:1 DEPX inhibit viral attachment in the range of 80-90%.

Example 3

This example shows the in vivo examination of 18:1 DEPX turnover, toxicity and anti-RSV activity Experimental Procedures Materials:

The human RSV A2 strain (VR-1540) and HEp2 cells were obtained from the ATCC. The virus was propagated in HEp2 cells with Dulbecco's Modified Eagle Medium/Ham's F12 Medium obtained from GIBCO and supplemented with 5% BGS from Hyclone. Viral preparations were purified using methods described previously and quantified by plaque assay [M. Numata, H. W. Chu, A. Dakhama, and D. R. Voelker, "Pulmonary surfactant phosphatidylglycerol inhibits respiratory syncytial virus-induced inflammation and infection.," *Proc. Natl. Acad. Sci. U.S.A*, vol. 107, no. 1, pp. 320-5, 2010.]. Female BALB/c mice at 6 weeks of age were obtained from Jackson Laboratory. Isoflurane was used to anesthetize mice for intranasal inoculation. Chemical reagents for thin layer chromatographic separation of lipids were all HPLC grade purchased from Fisher Scientific. A kit to quantify IFNγ by ELISA was purchased from BD Biosciences. A RNA extraction kit was obtained from Omega Bio-tek. The RSV F-protein was quantified by qRT-PCR. The primers for F protein were 5' GGAGGAAGTCTTAG-CATATGTAG 3' (SEQ ID NO:1) and 5' CCATCCTCTGTCGGTTC 3' (SEQ ID NO:2). RNase inhibitor, dNTP's and Reverse Transcriptase was purchased from Invitrogen and SYBR Green was obtained from Applied Biosystems.

Determination of 18:1 DEPX Turnover in the Mouse Lung:

18:1 DEPX was prepared as liposomes so that 500 µg of lipid was delivered in a 50 µL volume. 6-week old female BALB/C mice were purchased from Jackson laboratories and divided into groups of 5. Each group was inoculated with 500 µg of 18:1 DEPX by intranasal inoculation. Groups of 5 mice were sacrificed and lavaged at the following time points: 0 hours, 3 hours, 6 hours, 18 hours and 24 hours. Lipids were extracted from mice BALF by Bligh-Dyer ("A rapid method of total lipid extraction and purification.," *Can. J. Biochem. Physiol.*, vol. 37, no. 8, pp. 911-7, August 1959), and quantified by phosphorus analysis. 150 nmol of lipid extracted from each mouse was separated by lipid class utilizing the Touchstone solvent system (refer to methods) and thin layer chromatography. 0.1% ANSA and UV light was used to visualize lipids from the thin layer chromatogram. Individual xylitol lipid bands were cut out from the silica and quantified by phosphorus analysis.

Inflammatory Burden Caused by Intranasal Inoculation of 18:1 DEPX:

Doses of 18:1 DEPX ranging from 35 µg to 1 mg were administered to mice by intranasal inoculation. The inflammatory burden caused by delivery of the synthetic lipid to the mouse lung was assessed 24 hours following inoculation. At 24 hours, mice were sacrificed and BALF was collected. The cells in BALF were quantified and cell populations within the lavage fluid were assessed by staining and cytospin analysis.

18:1 DEPX Interference with RSV Infection In Vivo:

Six-week-old female BALB/c mice were obtained from Jackson Laboratory. Mice were anesthetized with isoflurane and through intranasal inoculation a 50 μL volume of PBS control, 18:1 DEPX lipid alone, 18:1 DEPX+RSV or RSV only was delivered to mice. Mice were infected with 1×10$^7$ pfu/mL RSV. 18:1 DEPX liposomes were delivered to mice at a final amount of 100 μg. For lipid antagonism, RSV and 18:1 DEPX were mixed together in PBS prior to inoculation. Five days following initial infection, mice were euthanized by asphyxiation with carbon dioxide following prescribed guidelines by the IACUC. Next, mice were dissected to expose the trachea where a small cut was made to insert a luer stub. The lungs were then lavaged with 1 mL of saline. The chest cavity was opened and the lungs perfused with PBS and then removed. The left lung was homogenized in 1 mL of serum-free DMEM, the homogenates were centrifuged at 3800 rcf for 15 minutes at 4° C. and supernatant was used for quantitative plaque assay analysis. Lower right lungs were fixed overnight in 10% buffered formalin, then dehydrated and paraffin-embedded. Lungs were then sliced and stained with Hematoxylin-Eosin (H&E) for microscopy pictures and histopathological scoring. Total cell counts were determined from BALF and cell types were assessed by cytospin. IFN-γ was quantified by ELISA from the cell-free supernatants of BALF. The upper right lung was homogenized, RNA was extracted, converted to cDNA and RSV replication was determined by quantitative PCR of the F protein.

Determination of 18:1 DEPX Distribution by MALDI Imaging:

500 μg 18:1 DEPX was delivered to mice by intranasal inoculation. Mice were sacrificed at 0 hours following inoculation (immediately after gaining consciousness from anesthesia) and 24 hours following lipid delivery. Lungs were embedded in a modified optimal cutting temperature (mOCT) medium and placed at −21° C. overnight. Frozen lungs were sliced by a microtome with sections between 15 μm and 20 μm thick, placed on a glass cover slip and adhered to a matrix-assisted laser desorption ionization (MALDI) plate with conductive tape. Sublimation was used to coat the lung slices with a matrix for ionization by MALDI, 2'6'-Dihydroxyacetophenone for negative ion analysis. The matrix-coated lung slices were then placed in a MALDI-qTOF mass spectrometer. Spatial location of lipids were determined by laser ionization of spots in a stepwise fashion across the tissue where mass spectra is recorded in each location with note to its x-y coordinates. The intensity of a given ion was converted to a color-coded pixel localized where the spectra for it was gathered in the x-y plane. Over time the pixels of ion intensity make up the relative location of an ion within the tissue and form a map of distribution. The MS/MS capabilities of the qTOF was utilized to determine CID of the desired 18:1 DEPX ion to confirm its identification.

Results

Turnover of 18:1 DEPX in the Mouse Lung:

Bioactive lipid compounds delivered to the lung that have extended half-lives would offer protection from pathogens for longer periods. The idea behind synthesis of diether xylitol analogs was to create compounds that would have a longer lifetime than exogenous POPG in the mouse lung. To determine how quickly 18:1 DEPX turns over in the mouse lung, female BALB/C mice that were 6-8 weeks old were inoculated with 500 μg of lipid by intranasal delivery in a 50 μL volume. Mice were sacrificed at time periods of, 0 hours, 3 hours, 6 hours, 18 hours and 24 hours following lipid delivery and bronchoalveolar lavage fluid (BALF) was collected. Lipids were extracted from BALF by the Bligh-Dyer method and total lipid extracts were quantified by phosphorus analysis (G. Rouser, et al., "Quantitative analysis of phospholipids by thin-layer chromatography and phosphorus analysis of spots.," *Lipids*, vol. 1, no. 1, pp. 85-6, January 1966). To separate the various lipid classes present in BALF, thin layer chromatography on a Merck Silica 60 glass plate with a touchstone solvent system was utilized. The silica plate was scored in lanes according to number of samples, 150 nmol of total lipid was spotted onto each lane and solvent was developed for 90 minutes. The plate was air dried and sprayed with 0.1% ANSA-water then exposed to UV light to reveal migration of lipids on the plate. The spots corresponding to xylitol lipids were cut out and quantified by phosphorous analysis.

18:1 DEPX was detected in all mice across all time points and migrates in the touchstone solvent system below PG lipids and well above the prominent PC lipids that are easily distinguished. Xylitol lipids do not naturally exist in the mouse lung and are not seen in lipid extracts from control mice that did not receive PX lipid. Phosphorous analysis demonstrated that at time zero approximately 42 nmol of the 150 nmol of total lipid loaded was 18:1 DEPX. At each time point following immediate recovery of lipid from the 0 hour time point, the amount of 18:1 DEPX decreases. This decrease over time could be a result of cellular uptake of lipid, metabolism of the xylitol head group by phospholipase D or incorporation of PX lipid into the tissue. At 24 hours following intranasal delivery of lipid, about 20 nmol of 18:1 DEPX was detected in recovered lavage. Approximately half of the recovered xylitol lipid is still present in the mouse lung after 24 hours. This provides evidence that the half-life of 18:1 DEPX within the recoverable compartment by lavage greatly exceeds that of exogenous POPG, which was determined to be around 45 minutes.

Because toxicity of the synthetic phospholipid, 18:1 DEPX, is unknown lower levels of lipid were delivered to mice to determine if the diether lipid persists in the mouse lung after 24 hours. The previous experiment was repeated with 250 μg, 150 μg and 75 μg 18:1 DEPX delivered to mice. 250 μg was used as a starting point for mice sacrificed at 0 hours following lipid delivery. Subsequently groups of mice given 250 μg, 150 μg and 75 μg of 18:1 DEPX were sacrificed 24 hours following intranasal delivery of lipid. Mouse lungs were lavaged 2 times with 1 mL PBS. Total lipids were extracted by the Bligh-Dyer method from BALF and separated on a Merck Silica 60 glass plate using a touchstone solvent system for separation of lipids by headgroup. Xylitol lipid spots were excised from the silica and quantified by phosphorus assay.

18:1 DEPX was detectable visually by TLC as well as quantitatively by phosphorus analysis in all mice. Around 40 μg of xylitol lipid was recovered from mice that received 250 μg 18:1 DEPX and were sacrificed immediately upon gaining consciousness from anesthesia. Mice that received 250 μg 18:1 DEPX that were sacrificed 24 hours following lipid delivery had around 20 μg of PX lipid recovered. This finding is consistent with the previous experiment that at 24 hours following lipid instillation, about half of the xylitol lipid that was recovered at time 0 hours was recovered at 24 hours. Lower levels of 18:1 DEPX were recovered from the 150 μg and 75 μg lipid instillation groups amounting to 15 μg and 10 μg respectively. This study confirms the relatively long half-life of 18:1 DEPX when compared with POPG in the mouse lung.

Assessing Inflammatory Burden of 18:1 DEPX In Vivo:

In order to determine the dose of 18:1 DEPX that is used in RSV challenge experiments, the toxic effects of the lipid were studied by the inflammatory response it elicits following delivery. A range of doses of 18:1 DEPX, from 35 µg to 1 mg, was instilled intranasally to 6-8 week old female BALB/C mice. Mice were sacrificed 24 hours following lipid delivery to best assess immediate inflammatory response. Mouse lungs were lavaged with 1 mL PBS and BALF was assessed for total inflammatory cellular infiltrates quantitatively and further characterized for cell populations by cytospin.

Mice in the PBS control group had around 104 cells/mL of BALF. Mice in the 35 µg, 75 µg, 150 µg, and 250 µg 18:1 DEPX groups did not have cell counts distinguishable from the control when analysis of variance was performed. Mice that received 300 µg, 500 µg and 1 mg of 18:1 DEPX had significantly higher cell counts in their lavage fluid compared to the PBS control. One mouse in the group that received 1 mg of 18:1 DEPX died.

Following quantification of cells in 1 mL BALF, cells were subjected to cytospin and fixed and stained on microscope slides. 500 cells were counted from each slide and the numbers of macrophages, neutrophils and lymphocytes recorded. Delivery of 18:1 DEPX to mice elicits an inflammatory response determined by the influx of neutrophils found in lavage. 18:1 DEPX could have toxic effects at higher doses and even though cell numbers in BALF was not significantly different from the control mice until 300 µg of lipid, significant numbers of neutrophils are seen at 75 µg 18:1 DEPX. Therefore, a dose of 100 µg 18:1 DEPX was chosen to perform RSV challenge experiments.

Evaluation of the Protective Effects of 18:1 DEPX in Mice Challenged with RSV:

The use of liposomes in medicine is not a new concept, however the approach where the liposome itself possesses bioactivity and has the ability to modulate immune responses and inhibit viral infection is a new area of research. The synthetic diether phospholipid, 18:1 DEPX, was tested for its ability to protect the mouse lung during RSV viral infection.

Female BALB/C mice were obtained from Jackson Laboratories at 6 weeks of age. The experiment consisted of four groups, a PBS control, 18:1 DEPX liposomes alone, 18:1 DEPX liposomes+RSV and RSV alone. Mice were inoculated with RSV at $1\times10^7$ pfu/mL. 100 µg 18:1 DEPX was the dose tested for protective effects in the mouse lung. Each mouse group underwent intranasal inoculation for delivery of experimental conditions in a final volume of 50 µL. Mice were monitored daily and body weight was recorded. At the height of RSV infection on day 5, the mice were euthanized. Bronchoalveolar lavage fluid (BALF) was collected, the chest cavity was opened and the lungs removed. The left lobe of the lungs was homogenized in serum-free DMEM, centrifuged at 3800 rcf for 15 minutes at 0° C. and the supernatant collected for quantitative plaque assay described in the previous chapter. The lower right lobe of the lung was fixed overnight in 10% buffered formalin and then processed by paraffin embedding, slicing and fixing of the lung to a microscope slide and H&E staining. The upper right lobe of the lung was homogenized, RNA was extracted and converted to cDNA and then quantitative real-time PCR was used to determine RSV replication by quantification of the F protein. Cells within BALF were quantified and assessed for cell populations by cytospin. BALF supernatant was stored and subsequently used for IFNγ quantification.

Figure 10:
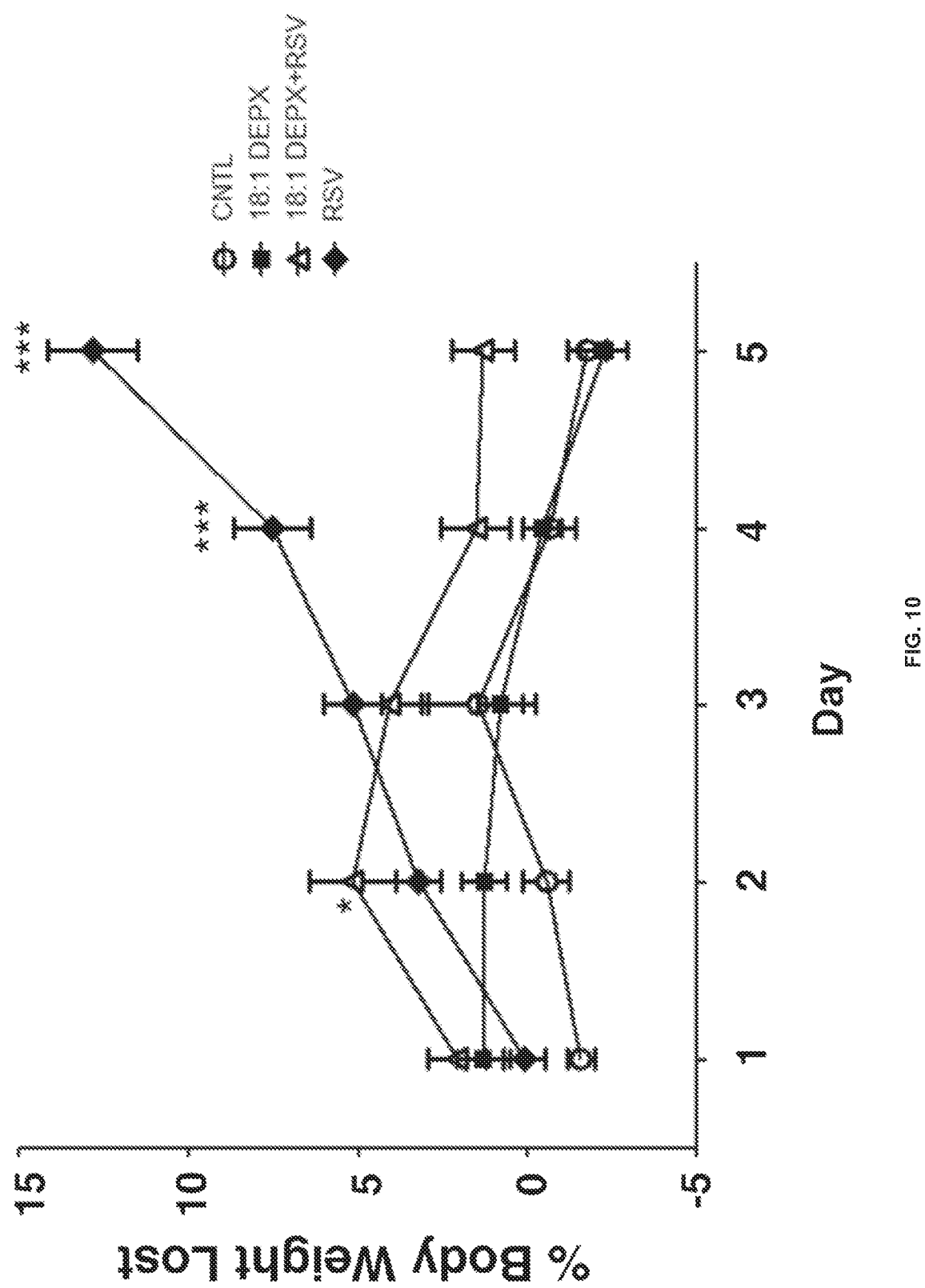
FIG. 10 shows 18:1 DEPX suppresses RSV infection-induced weight loss in mice. Mice were either sham infected (CNTRL), or virus infected (RSV), or treated with lipid and virus (18:1 DEPX+RSV), or treated with lipid alone (18:1 DEPX). The mice were weighed daily. *** indicates $p<0.0001$.

Overall the control mice and mice that received 18:1 DEPX alone showed no difference in daily body weight expressed as percent of starting body weight lost. Mice that received 18:1 DEPX in combination with RSV appeared to be affected early on by the virus, but were able to gain weight normally after day 2 indicating they were feeling better and eating. Mice in the RSV alone group were visibly sick and continued to worsen over the 5-day experiment as indicated by continual loss of body weight. A summary of percent body weight lost for all groups of mice are summarized in FIG. 10. In studies shown in FIG. 10, mice were challenged with either saline (CNTL), or $10^7$ virus (RSV), or virus plus 18:1 DEPX (18:1 DEPX+RSV), or lipid alone (18:1 DEPX). The mice were weighed each day. The results demonstrate that RSV induces weight loss over the time course of the experiment and 18:1 DEPX prevents the weight loss caused by viral infection.

Figure 11:
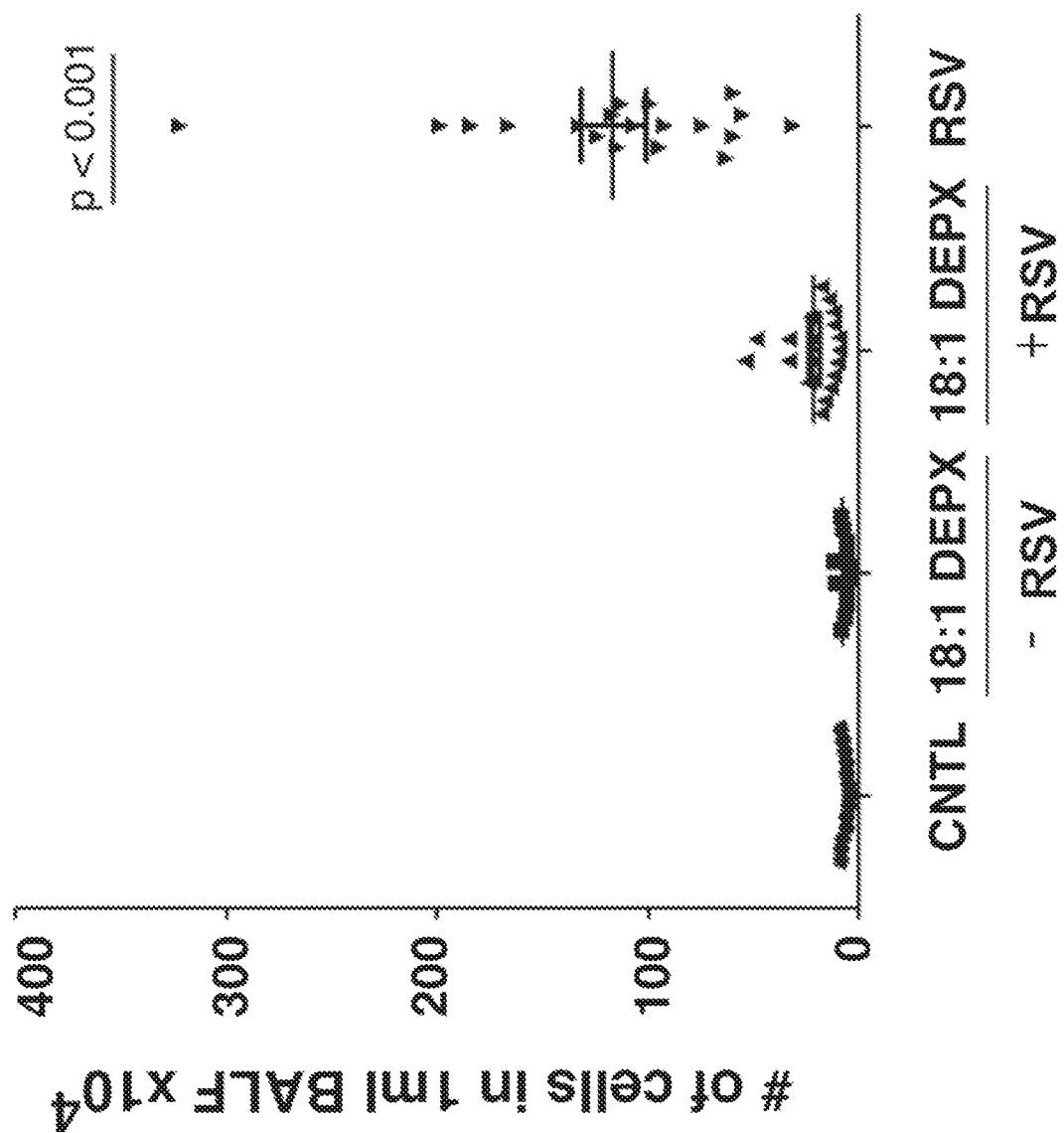
FIG. 11 shows 18:1 DEPX suppresses influx of inflammatory cells into the lungs induced by RSV infection. Mice were either sham treated (CNTL) or infected with $10^7$ RSV in either the absence (RSV), or presence of 18:1 DEPX (18:1 DEPX+RSV), or treated with lipid alone (18:1 DEPX– RSV). After 6 days animals were euthanized and lavaged with 1 ml of saline. Total cells present in the lavage were quantified by cell counting using a hemocytometer.

On day 5 following RSV infection mice were sacrificed by carbon dioxide asphyxiation according to IACUC protocol. Mice were dissected to expose the trachea where a small cut was made for the insertion of a leur stub and the lungs were lavaged with 1 mL of saline. A 20 µL aliquot was obtained from BALF collected and cellular infiltration into the lungs was quantified using a hemocytometer. The remaining lavage fluid was centrifuged at 500×g for 5 minutes, supernatant was collected and cells were resuspended in PBS for cytospin. Quantification of cells in 1 mL of BALF is reported in FIG. 11. In studies shown in FIG. 11, mice were challenged with either saline (CNTL), or $10^7$ virus (RSV), or virus plus 18:1 DEPX (18:1 DEPX+RSV), or lipid alone (18:1 DEPX). The mice received all agents in a volume of 50 µl applied intranasally. On day 6 the mice were euthanized and the lungs were lavaged with saline. The cells in the lavage were recovered by centrifugation and quantified by counting using a hemocytometer. In RSV infected mice cell numbers were ~$120\times10^4$. In contrast, animals infected with RSV and receiving 18:1 DEPX intranasally, had cell numbers of ~$20\times10^4$ that were not significantly different from saline treated or 18:1 DEPX treatment alone.

There was no difference in number of cells quantified in lavage between the control and 18:1 DEPX mice. There appears to be an increase in the number of cells found in the mice that received 18:1 DEPX+RSV but it was determined not to be statistically significant by ANOVA followed by Tukey's post-hoc test. However, during a more direct comparison T Test, the 18:1 DEPX+RSV group was determined to be significantly different from the control where p=0.0003. The RSV mice had significantly higher amounts of cells within the lung when compared to all other groups. Although protection appears less than complete, 18:1 DEPX suppresses an overabundance of cellular infiltration in the mouse lung during RSV infection.

Cytospin analyses revealed that the control mice and 18:1 DEPX mice possessed mainly macrophages within the lung and that there was no difference between populations of these two groups. Mice treated with 18:1 DEPX+RSV and RSV alone had increased numbers of macrophages, lymphocytes and neutrophils within the lung compared to the PBS control. However, the RSV alone mice had significantly increased numbers of all cell types assessed compared with the 18:1 DEPX+RSV mice. This indicates that 18:1 DEPX protects the mouse lung from RSV infection as seen by the decreased number of inflammatory cellular infiltrates found in BALF.

The supernatant from mouse BALF was used to quantify interferon gamma (IFNγ) in the mouse lung among the four different experimental groups. IFNγ is a type II interferon secreted by T lymphocytes and natural killer cells (J. R. Schoenborn and C. B. Wilson, "Regulation of Interferon—During Innate and Adaptive Immune Responses," *Adv. Immunol.*, vol. 96, pp. 41-101, 2007). It is important for both innate and adaptive immune functions in response to viral infections by activating macrophages and inducing MHC II expression among other roles. RSV strongly induces IFNγ secretion and was quantified in BALF as one measure of degree of RSV infection. An ELISA kit specific for mouse IFNγ was purchased from BD Biosciences and the protocol followed.

Control mice and 18:1 DEPX mice had relatively low levels of IFNγ within their lungs. Around 1 ng/mL of IFNγ was quantified in 18:1 DEPX+RSV mice whereas RSV alone mice had upwards of 6 ng/mL IFNγ. These results indicate that an infection is present in the 18:1 DEPX+RSV mice but the infection is reduced compared to the RSV alone mice that did not receive lipid treatment.

The left lobe of the mouse lung was homogenized to assess viral load by quantitative plaque assay. HEp2 cells were plated at a density of 1.8 million cells per well in a 6 well plate, 24 in advance of infection to insure a competent cell monolayer. Following homogenization of lungs, samples were centrifuged at 3800 rcf for 15 minutes at 0° C. and the supernatant was collected. Dilutions of lung homogenate supernatant were made and applied to HEp2 cells for a 2-hour infection at 37° C. where plates were rotated every 30 minutes. Following viral infection, the inoculum was removed and overlayed with serum free medium containing 0.3% agarose and placed at 37° C. for 6 days. On day 6, cells were fixed overnight with formalin and stained with neutral red and viral plaque numbers were counted (J. L. McKimm-Breschkin, "A simplified plaque assay for respiratory syncytial virus-direct visualization of plaques without immunostaining," 2004).

Viral plaques were not observed in the control and 18:1 DEPX mice. Between 100 and 200 pfu/mL were observed for mice infected with RSV that received 18:1 DEPX lipid treatment. RSV alone mice had an average viral load of 400 pfu/mL. These results indicate that the presence of 18:1 DEPX inhibits RSV infection resulting in a 50% reduction of viral plaque number.

RNA was isolated from each mouse and quantitative PCR was used to determine viral replication. The upper right lobe of the mouse lung was homogenized and RNA was extracted according to protocol using a kit purchased from Omega Bio-tek. The extracted RNA was then converted to cDNA, and then subjected to qRT-PCR. Relative expression of RSV for 3 independent experiments is summarized in FIGS. 12A and 12B.

Figure 12B:
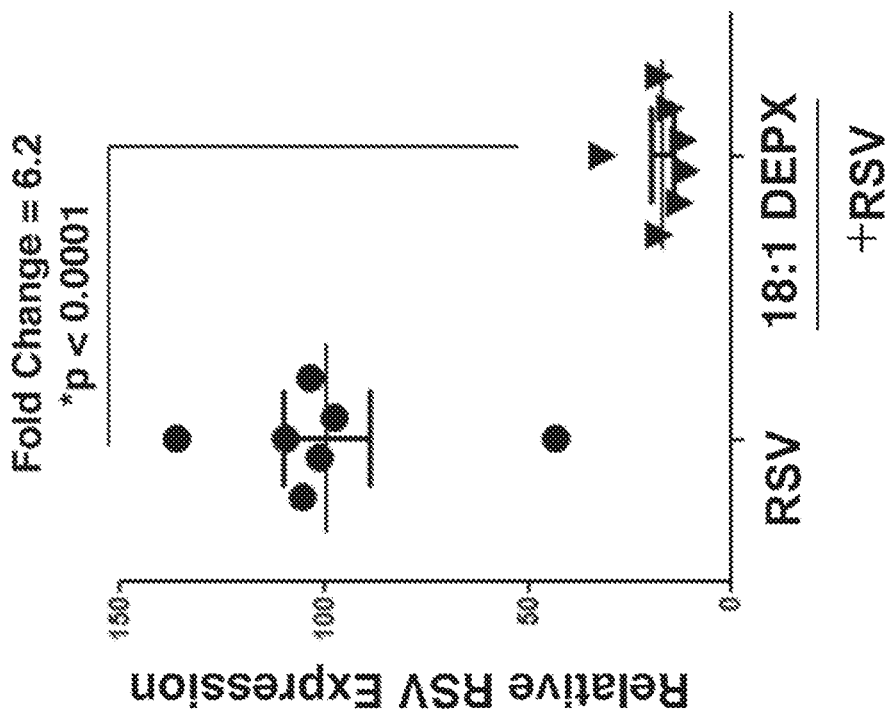
FIGS. 12A and 12B show 18:1 DEPX reduces viral copy number recovered from lung tissue. Mice were infected with $10^7$ RSV in either the absence (RSV), or presence of 18:1 DEPX (18:1 DEPX+RSV). After 6 days lungs were harvested and RNA was isolated. Genomic viral RNA was quantified by qRT-PCR.
Figure 12A:
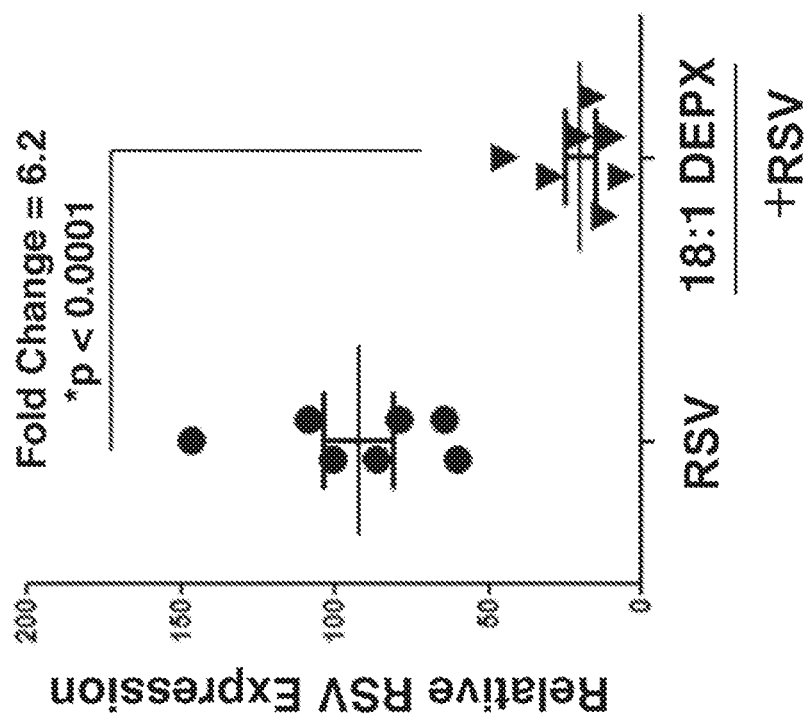

In each of the three viral challenge experiments performed, 18:1 DEPX inhibits RSV infection and is reflected in the lower levels of RSV expression in the qPCR data. RSV infection in two in vivo viral experiments is shown in FIGS. 12A and 12B. A 2.6-fold reduction in RSV expression is observed in the 18:1 DEPX treated viral group. In the two subsequent experiments higher levels of RSV were observed among the virus alone group. Mice that received 18:1 DEPX+RSV in the latter two experiments, however, reduced RSV expression by a factor of 6.2. The synthetic diether xylitol lipid has a clear protective effect on the mouse lung during RSV infection. The lower right lobe of the mouse lung was processed for histopathology. In studies shown in FIGS. 12A and 12B, mice were challenged with either saline (CNTL), or $10^7$ virus (RSV), or virus plus 250 µg 18:1 DEPX (18:1 DEPX+RSV), or 250 µg of lipid alone (18:1 DEPX). The mice received all agents in a volume of 50 µl applied intranasally. On day 6 the mice were euthanized and the lungs were harvested and processed for RNA isolation and the purified RNA was subjected to qRT-PCR to quantify viral genomes in the tissue. The data demonstrate that the 18:1 DEPX treatment reduces the viral burden by a factor of 6.2.

Control mice and 18:1 DEPX mice appeared similar in micrographs of lung sections. There was not much cellular infiltration into the lungs, nor was thickening of the airways observed in these populations. Lung tissue from mice that were infected with RSV but treated with 18:1 DEPX appeared less affected by the virus than the RSV lone group. Cellular infiltrates and some airway thickening was observed in the 18:1 DEPX group as well as the RSV group when compared with the control and lipid alone mice. Complete protection from RSV infection was not observed with treatment, however mice that received the lipid were overall healthier than those that did not receive lipid treatment.

18:1 DEPX Localization in the Mouse Lung:

From previous experiments discussed above, 18:1 DEPX delivered to the mouse by intranasal inoculation is retained within the lung for long periods of time and has a protective effect in the presence of RSV infection. To determine localization of 18:1 DEPX in the mouse lung following intranasal inoculation, matrix-assisted laser desorption ionization (MALDI) imaging mass spectrometry was used. MALDI imaging mass spectrometry is able to determine spatial location of lipids in tissues without additional labeling of the desired molecules. To determine 18:1 DEPX distribution in the mouse lung, mice were inoculated intranasally with 500 µg of the lipid in a final volume of 50 µL. Mice were sacrificed at 0 hours and 24 hours following lipid delivery by carbon dioxide asphyxiation. Mice were dissected and the trachea exposed, cut and a modified optimal cutting tissue (mOCT) medium was used to inflate the lungs. The left lung was tied off and excised from the mouse and embedded in additional mOCT in a cryo mold and placed at −21° C. for a minimum of 24 hours. After freezing, lungs were sliced with a microtome to obtain sections between 15 µm and 20 µm thick. The slices were adhered to glass cover slips, attached to a MALDI metal plate and sublimation was used to coat the tissue with matrix so that ionization will occur (K. A. Z. Berry, et al., "MALDI imaging of lipid biochemistry in tissues by mass spectrometry.," *Chem. Rev.*, vol. 111, no. 10, pp. 6491-512, October 2011). After coating the tissue, the plate was placed in a MALDI qTOF mass spectrometer. The laser-ionizing source is set to raster across the tissue in a step-wise fashion collecting mass spectra as it goes and assigns a relative intensity to each individual ion within a spectra at each given point in the x-y plane. Each ion at every point in the x-y plane is then converted to a pixel and assigned a relative pixel intensity. The collective visualization of all of the pixel intensities at a given m/z illustrates the distribution and relative amount within the tissue. The MALDI qTOF also has MS/MS capability which was used to confirm the presence of 18:1 DEPX within the tissue by determining if the CID of the tissue ion matched that previously described above for 18:1 DEPX.

18:1 DEPX is not an endogenous lipid and has a unique m/z, 805.5, as a negative ion. This corresponds to a PBS control mouse at the m/z of the xylitol lipid. This demonstrates that there is no endogenous lipid that corresponds to m/z 805.5 so that the signal visualized at this mass is the 18:1 DEPX lipid. An abundant signal of m/z 805.5 is observed in both the time 0-hour mouse as well as the 24-hour mouse and demonstrates distribution throughout the peripheral lung tissue. The distribution of 18:1 DEPX appears to correlate with the location of the other surfactant lipids, PG and PC, and is not observed highly concentrated in airways like the PE lipid.

18:1 DEPX was determined to rapidly disperse throughout the mouse lung with similar distribution to the surfactant lipids POPG and DPPC. Next the localization of the PX lipid was assessed. MALDI imaging was used to determine if PX lipid was in the recoverable portion of the lungs or whether it was embedded in the tissue. The previously described experiment was repeated with 250 µg of 18:1 DEPX delivered to mice by intranasal inoculation. This time before mOCT was injected into the mouse lung following euthanization, the lungs were washed 5 times with 1 mL aliquots of PBS to remove 18:1 DEPX.

18:1 DEPX was still observed in the mouse lung following five 1-mL lavages. Although lavaging the lung 5 times does not completely remove all of the recoverable surfactant and cells from airways it removes the majority of them. These results indicate that 18:1 DEPX is distributed throughout the mouse lung following intranasal inoculation and is mainly confined to the recoverable portions of the lung similar to the surfactant lipids POPG and DPPC. However, there is some residual amount of the PX retained in the tissue, and this experiment was not performed in conjunction with a non-lavaged control.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

viral infection, and wherein the xylitol lipid analog is Diether-phosphatidylxylitol (DEPX) or an analog thereof.

2. The method of claim 1, wherein the RSV infection activates at least one Toll-like receptor (TLR) selected from the group consisting of TLR1, TLR2, TLR3, TLR4, TLR6, TLR7, TLR8, TLR9, and TLR10.

3. The method of claim 1, wherein the DEPX lipid analog is selected from the group consisting of 14:0 Diether-phosphatidylxylitol (14:0 DEPX) and 18:1 Diether-phosphatidylxylitol (18:1 DEPX).

4. The method of claim 1, wherein the individual is a neonatal infant.

5. The method of claim 1, wherein the xylitol lipid analog is administered to the individual prior to any indication of viral infection.

6. The method of claim 1, wherein the xylitol lipid analog is administered to the individual subsequent to identification of a symptom of, or confirmation of, viral infection of the individual.

7. The method of claim 1, wherein the xylitol lipid analog is administered as a homogeneous lipid preparation.

8. The method of claim 1, wherein the xylitol lipid analog is administered as a composition comprising a homogeneous lipid preparation of the xylitol lipid analog.

9. The method of claim 1, wherein the xylitol lipid analog is administered as a composition comprising a preparation of randomly mixed surfactant lipids combined with a homogeneous lipid preparation of the xylitol lipid analog.

10. The method of claim 1, wherein the xylitol lipid analog is administered as a preparation of randomly mixed

What is claimed:

1. A method to inhibit respiratory syncytial virus (RSV) infection in an individual who has, or is at risk of developing, RSV infection, the method comprising administering to the individual at least one xylitol lipid analog, wherein an amount of the xylitol lipid analog is effective to inhibit said surfactant lipids, wherein the xylitol lipid analog comprises at least about 50% of the total lipids in said randomly mixed surfactant lipids.

11. The method of claim 1, wherein the xylitol lipid analog is administered via respiratory tract of the individual.

12. The method of claim 1, wherein the xylitol lipid analog is administered via nasal passages of the individual.

13. The method of claim 1, wherein the xylitol lipid analog suppresses activation of at least one TLR selected from the group consisting of TLR1, TLR2, TLR3, TLR4, and TLR7.

14. The method of claim 1, wherein the xylitol lipid analog is administered in combination with at least one material selected from the group consisting of POPG, SP-A and SP-D.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: F protein primer 1

<400> SEQUENCE: 1
ggaggaagtc ttagcatatg tag                                           23

<210> SEQ ID NO 2
<211> LENGTH: 17
<212> TYPE: DNA
<213> ORGANISM: Artificial Sequence
<220> FEATURE:
<223> OTHER INFORMATION: F protein primer 2

<400> SEQUENCE: 2
ccatcctctg tcggttc                                                  17
```